(12) United States Patent
Griffiths et al.

(10) Patent No.: US 9,857,303 B2
(45) Date of Patent: Jan. 2, 2018

(54) SELECTION BY COMPARTMENTALISED SCREENING

(75) Inventors: Andrew David Griffiths, Cambridge (GB); Chris Abell, Cambridge (GB); Florian Hollfelder, Cambridge (GB); Enrico Mastrobattista, Cambridge (GB)

(73) Assignee: Medical Research Council, London (GB)

(*) Notice: Subject to any disclaimer, the term of this patent is extended or adjusted under 35 U.S.C. 154(b) by 0 days.

(21) Appl. No.: 13/208,614

(22) Filed: Aug. 12, 2011

(65) Prior Publication Data

US 2012/0010107 A1 Jan. 12, 2012

Related U.S. Application Data

(63) Continuation of application No. 11/238,258, filed on Sep. 29, 2005, now Pat. No. 9,448,172, which is a continuation of application No. PCT/GB2004/001362, filed on Mar. 31, 2004.

(30) Foreign Application Priority Data

Mar. 31, 2003 (GB) .................................. 0307403.6

(51) Int. Cl.
| | |
|---|---|
| *C40B 40/00* | (2006.01) |
| *C40B 40/06* | (2006.01) |
| *G01N 21/64* | (2006.01) |
| *G01N 33/543* | (2006.01) |
| *C40B 50/08* | (2006.01) |

(52) U.S. Cl.
CPC ..... *G01N 21/6428* (2013.01); *G01N 33/5432* (2013.01); *B01J 2219/00596* (2013.01); *B01J 2219/00599* (2013.01); *B01J 2219/00702* (2013.01); *C40B 50/08* (2013.01); *G01N 21/6458* (2013.01)

(58) Field of Classification Search
CPC ... A61K 9/50; A61K 9/16; C12Q 1/68; C40B 40/00; C40B 40/06
USPC .......................... 424/490; 435/6.1; 506/9, 16
See application file for complete search history.

(56) References Cited

U.S. PATENT DOCUMENTS

| | | | |
|---|---|---|---|
| 2,097,692 A | 11/1937 | Fiegel | |
| 2,164,172 A | 6/1939 | Dalton | |
| 2,656,508 A | 10/1953 | Coulter | |
| 2,692,800 A | 10/1954 | Nichols et al. | |
| 2,797,149 A | 6/1957 | Skeggs | |
| 2,879,141 A | 3/1959 | Skeggs | |
| 2,971,700 A | 2/1961 | Peeps | |
| 3,479,141 A | 11/1969 | Smythe et al. | |
| 3,608,821 A | 9/1971 | Simm et al. | |
| 3,698,635 A | 10/1972 | Sickles | |
| 3,816,331 A | 6/1974 | Brown, Jr. et al. | |
| 3,930,061 A | 12/1975 | Scharfenberger | |
| 3,960,187 A | 6/1976 | Stock et al. | |
| 3,980,541 A | 9/1976 | Aine | |
| 3,982,541 A | 9/1976 | L'Esperance, Jr. | |
| 4,014,469 A | 3/1977 | Sato | |
| 4,022,575 A | 5/1977 | Hansen et al. | |
| 4,034,966 A | 7/1977 | Suh et al. | |
| 4,059,552 A | 11/1977 | Zweigle et al. | |
| 4,091,042 A | 5/1978 | Alexanderson et al. | |
| 4,117,550 A | 9/1978 | Folland et al. | |
| 4,130,394 A | 12/1978 | Negersmith | |
| 4,210,809 A | 7/1980 | Pelavin | |
| 4,253,846 A | 3/1981 | Smythe et al. | |
| 4,266,721 A | 5/1981 | Sickles | |
| 4,279,345 A | 7/1981 | Allred | |
| 4,297,345 A | 10/1981 | Howarth | |
| 4,315,754 A | 2/1982 | Ruzicka et al. | |
| 4,378,957 A | 4/1983 | Malkin et al. | |
| 4,383,767 A | 5/1983 | Jido | |
| 4,439,980 A | 4/1984 | Biblarz et al. | |
| 4,508,265 A | 4/1985 | Jido | |
| 4,533,634 A | 8/1985 | Maldonado et al. | |
| 4,585,209 A | 4/1986 | Aine et al. | |
| 4,618,476 A | 10/1986 | Columbus | |
| 4,675,285 A | 6/1987 | Clark et al. | |

(Continued)

FOREIGN PATENT DOCUMENTS

| | | |
|---|---|---|
| AU | 2004225691 B2 | 6/2010 |
| CA | 2520548 A1 | 10/2004 |

(Continued)

OTHER PUBLICATIONS

Bagwe et al., 2001, Improved Drug Delivery Using Microemulsions: Rationale, Recent Progress, and New Horizons, Critical Reviews in Therapeutic Drug Carrier Systems, 18(1): 77-140.*
Krafft, 2001, Fluorocarbons and fluorinated amphiphiles in drug delivery and biomedical research, Advanced Drug Delivery Reviews, 47: 209-228.*
Tawfik et al., 1998, Man-made cell-like compartments for molecular evolution, Nature Biotechnology, 16: 652-656.*
Lodish et al., Structure of Nucleic Acids, Section 4.1, Molecular Cell Biology, 4th edition, New York, 2000, 1-3.*

(Continued)

*Primary Examiner* — Amy M Bunker
(74) *Attorney, Agent, or Firm* — Thomas C. Meyers; Brown Rudnick LLP

(57) ABSTRACT

The invention describes a method for the identification of compounds which bind to a target component of a biochemical system or modulate the activity of the target, by compartmentalizing the compounds into microcapsules together with the target, such that only a subset of the repertoire is represented in multiple copies in any one microcapsules; and identifying the compound which binds to or modulates the activity of the target. The invention enables the screening of large repertoires of molecules which can serve as leads for drug development.

9 Claims, 2 Drawing Sheets

(56) References Cited

U.S. PATENT DOCUMENTS

| | | |
|---|---|---|
| 4,676,274 A | 6/1987 | Brown |
| 4,683,195 A | 7/1987 | Mullis et al. |
| 4,683,202 A | 7/1987 | Mullis |
| 4,739,044 A | 4/1988 | Stabinsky |
| 4,757,141 A | 7/1988 | Fung et al. |
| 4,767,515 A | 8/1988 | Scott et al. |
| 4,767,929 A | 8/1988 | Valentine |
| 4,779,805 A | 10/1988 | Jackson et al. |
| 4,801,086 A | 1/1989 | Noakes |
| 4,801,529 A | 1/1989 | Perlman |
| 4,829,996 A | 5/1989 | Noakes et al. |
| 4,853,336 A | 8/1989 | Saros et al. |
| 4,865,444 A | 9/1989 | Green et al. |
| 4,883,750 A | 11/1989 | Whiteley et al. |
| 4,908,112 A | 3/1990 | Pace |
| 4,931,225 A | 6/1990 | Cheng |
| 4,941,959 A | 7/1990 | Scott |
| 4,962,885 A | 10/1990 | Coffee |
| 4,963,498 A | 10/1990 | Hillman et al. |
| 4,981,580 A | 1/1991 | Auer |
| 4,996,004 A | 2/1991 | Bucheler et al. |
| 5,091,652 A | 2/1992 | Mathies et al. |
| 5,096,615 A | 3/1992 | Prescott et al. |
| 5,122,360 A | 6/1992 | Harris et al. |
| 5,180,662 A | 1/1993 | Sitkovsky |
| 5,185,099 A | 2/1993 | Delpuech et al. |
| 5,188,290 A | 2/1993 | Gebauer et al. |
| 5,188,291 A | 2/1993 | Cross |
| 5,204,112 A | 4/1993 | Hope et al. |
| 5,207,973 A | 5/1993 | Harris et al. |
| 5,241,159 A | 8/1993 | Chatteriee et al. |
| 5,260,466 A | 11/1993 | McGibbon |
| 5,262,027 A | 11/1993 | Scott |
| 5,270,163 A | 12/1993 | Gold et al. |
| 5,296,375 A | 3/1994 | Kricka et al. |
| 5,304,487 A | 4/1994 | Wilding et al. |
| 5,310,653 A | 5/1994 | Hanausek-Walaszek et al. |
| 5,313,009 A | 5/1994 | Guenkel et al. |
| 5,344,594 A | 9/1994 | Sheridon |
| 5,378,957 A | 1/1995 | Kelly |
| 5,397,605 A | 3/1995 | Barbieri et al. |
| 5,399,461 A | 3/1995 | Van et al. |
| 5,399,491 A | 3/1995 | Kacian et al. |
| 5,401,634 A * | 3/1995 | Milbrath ............... 435/6.15 |
| 5,403,617 A | 4/1995 | Haaland |
| 5,413,924 A | 5/1995 | Kosak et al. |
| 5,417,235 A | 5/1995 | Wise et al. |
| 5,427,946 A | 6/1995 | Kricka et al. |
| 5,445,934 A | 8/1995 | Fodor et al. |
| 5,452,878 A | 9/1995 | Gravesen et al. |
| 5,452,955 A | 9/1995 | Lundstrom |
| 5,454,472 A | 10/1995 | Benecke et al. |
| 5,460,945 A | 10/1995 | Springer et al. |
| 5,475,096 A | 12/1995 | Gold et al. |
| 5,480,614 A | 1/1996 | Kamahori |
| 5,486,335 A | 1/1996 | Wilding et al. |
| 5,498,392 A | 3/1996 | Wilding et al. |
| 5,500,415 A | 3/1996 | Dollat et al. |
| 5,503,851 A | 4/1996 | Mank et al. |
| 5,512,131 A | 4/1996 | Kumar et al. |
| 5,516,635 A | 5/1996 | Ekins et al. |
| 5,518,709 A | 5/1996 | Sutton et al. |
| 5,523,162 A | 6/1996 | Franz et al. |
| 5,587,128 A | 12/1996 | Wilding et al. |
| 5,604,097 A | 2/1997 | Brenner |
| 5,612,188 A | 3/1997 | Shuler et al. |
| 5,616,478 A | 4/1997 | Chetverin et al. |
| 5,617,997 A | 4/1997 | Kobayashi et al. |
| 5,635,358 A | 6/1997 | Wilding et al. |
| 5,636,400 A | 6/1997 | Young |
| 5,641,658 A | 6/1997 | Adams et al. |
| 5,643,729 A | 7/1997 | Taniguchi et al. |
| 5,655,517 A | 8/1997 | Coffee |
| 5,656,155 A | 8/1997 | Norcross et al. |
| 5,661,222 A | 8/1997 | Hare |
| 5,662,874 A | 9/1997 | David |
| 5,670,325 A | 9/1997 | Lapidus et al. |
| 5,681,600 A | 10/1997 | Antinone et al. |
| 5,695,934 A | 12/1997 | Brenner |
| 5,726,026 A | 3/1998 | Wilding et al. |
| 5,726,404 A | 3/1998 | Brody |
| 5,733,526 A * | 3/1998 | Trevino et al. ............... 424/9.52 |
| 5,739,036 A | 4/1998 | Parris |
| 5,744,366 A | 4/1998 | Kricka et al. |
| 5,750,988 A | 5/1998 | Apffel et al. |
| 5,762,775 A | 6/1998 | DePaoli et al. |
| 5,779,868 A | 7/1998 | Parce et al. |
| 5,783,431 A | 7/1998 | Peterson et al. |
| 5,840,506 A | 11/1998 | Giordano |
| 5,846,719 A | 12/1998 | Brenner et al. |
| 5,849,491 A | 12/1998 | Radomski et al. |
| 5,858,187 A | 1/1999 | Ramsey et al. |
| 5,858,655 A | 1/1999 | Arnold |
| 5,858,670 A | 1/1999 | Lam et al. |
| 5,863,722 A | 1/1999 | Brenner |
| 5,868,322 A | 2/1999 | Loucks, Jr. et al. |
| 5,872,010 A | 2/1999 | Karger et al. |
| 5,876,771 A | 3/1999 | Sizer et al. |
| 5,880,071 A | 3/1999 | Parce et al. |
| 5,882,680 A | 3/1999 | Suzuki et al. |
| 5,884,846 A | 3/1999 | Tan |
| 5,887,755 A | 3/1999 | Hood, III |
| 5,888,746 A | 3/1999 | Tabiti et al. |
| 5,888,778 A | 3/1999 | Shuber |
| 5,904,933 A * | 5/1999 | Riess et al. ................... 424/450 |
| 5,921,678 A | 7/1999 | Desai et al. |
| 5,927,852 A | 7/1999 | Serafin |
| 5,928,870 A | 7/1999 | Lapidus et al. |
| 5,932,100 A | 8/1999 | Yager et al. |
| 5,935,331 A | 8/1999 | Naka et al. |
| 5,942,056 A | 8/1999 | Singh |
| 5,942,443 A | 8/1999 | Parce et al. |
| 5,958,203 A | 9/1999 | Parce et al. |
| 5,972,187 A | 10/1999 | Parce et al. |
| 5,980,936 A | 11/1999 | Krafft et al. |
| 5,989,815 A | 11/1999 | Skolnick et al. |
| 5,989,892 A | 11/1999 | Nishimaki et al. |
| 5,995,341 A | 11/1999 | Tanaka et al. |
| 5,997,636 A | 12/1999 | Gamarnik et al. |
| 6,008,003 A | 12/1999 | Haak-Frendscho et al. |
| 6,023,540 A | 2/2000 | Walt et al. |
| 6,028,066 A | 2/2000 | Unger |
| 6,042,709 A | 3/2000 | Parce et al. |
| 6,045,755 A | 4/2000 | Lebl et al. |
| 6,046,056 A | 4/2000 | Parce et al. |
| 6,048,551 A | 4/2000 | Hilfinger et al. |
| 6,068,199 A | 5/2000 | Coffee |
| 6,080,295 A | 6/2000 | Parce et al. |
| 6,086,740 A | 7/2000 | Kennedy |
| 6,096,495 A | 8/2000 | Kasai et al. |
| 6,103,537 A | 8/2000 | Ullman et al. |
| 6,105,571 A | 8/2000 | Coffee |
| 6,105,877 A | 8/2000 | Coffee |
| 6,116,516 A | 9/2000 | Ganan-Calvo |
| 6,118,849 A | 9/2000 | Tanimori et al. |
| 6,119,953 A | 9/2000 | Ganan-Calvo et al. |
| 6,120,666 A | 9/2000 | Jacobson et al. |
| 6,124,388 A | 9/2000 | Takai et al. |
| 6,124,439 A | 9/2000 | Friedman et al. |
| 6,130,052 A | 10/2000 | Van Baren et al. |
| 6,130,098 A | 10/2000 | Handique et al. |
| 6,137,214 A | 10/2000 | Raina |
| 6,138,077 A | 10/2000 | Brenner |
| 6,139,303 A | 10/2000 | Reed et al. |
| 6,140,053 A | 10/2000 | Koster |
| 6,143,496 A | 11/2000 | Brown et al. |
| 6,149,789 A | 11/2000 | Benecke et al. |
| 6,150,180 A | 11/2000 | Parce et al. |
| 6,150,516 A | 11/2000 | Brenner et al. |
| 6,165,778 A | 12/2000 | Kedar |
| 6,171,796 B1 | 1/2001 | An et al. |
| 6,171,850 B1 | 1/2001 | Nagle et al. |
| 6,172,214 B1 | 1/2001 | Brenner |
| 6,172,218 B1 | 1/2001 | Brenner |

(56) References Cited

U.S. PATENT DOCUMENTS

| | | |
|---|---|---|
| 6,174,160 B1 | 1/2001 | Lee et al. |
| 6,174,469 B1 | 1/2001 | Ganan-Calvo |
| 6,180,372 B1 | 1/2001 | Franzen |
| 6,184,012 B1 | 2/2001 | Neri et al. |
| 6,187,214 B1 | 2/2001 | Ganan-Calvo |
| 6,189,803 B1 | 2/2001 | Ganan-Calvo |
| 6,196,525 B1 | 3/2001 | Ganan-Calvo |
| 6,197,335 B1 | 3/2001 | Sherman |
| 6,197,835 B1 | 3/2001 | Ganan-Calvo |
| 6,203,993 B1 | 3/2001 | Shuber et al. |
| 6,210,396 B1 | 4/2001 | MacDonald et al. |
| 6,210,891 B1 | 4/2001 | Nyren et al. |
| 6,210,896 B1 | 4/2001 | Chan |
| 6,214,558 B1 | 4/2001 | Shuber et al. |
| 6,221,654 B1 | 4/2001 | Quake et al. |
| 6,227,466 B1 | 5/2001 | Hartman et al. |
| 6,234,402 B1 | 5/2001 | Ganan-Calvo |
| 6,235,383 B1 | 5/2001 | Hong et al. |
| 6,235,475 B1 | 5/2001 | Brenner et al. |
| 6,241,159 B1 | 6/2001 | Ganan-Calvo et al. |
| 6,243,373 B1 | 6/2001 | Turock |
| 6,248,378 B1 | 6/2001 | Ganan-Calvo |
| 6,251,661 B1 | 6/2001 | Urabe et al. |
| 6,252,129 B1 | 6/2001 | Coffee |
| 6,258,568 B1 | 7/2001 | Nyren |
| 6,258,858 B1 | 7/2001 | Nakajima et al. |
| 6,263,222 B1 | 7/2001 | Diab et al. |
| 6,266,459 B1 | 7/2001 | Walt et al. |
| 6,267,353 B1 | 7/2001 | Friedline et al. |
| 6,267,858 B1 | 7/2001 | Parce et al. |
| 6,268,165 B1 | 7/2001 | O'Brien |
| 6,268,222 B1 | 7/2001 | Chandler et al. |
| 6,274,320 B1 | 8/2001 | Rothberg et al. |
| 6,274,337 B1 | 8/2001 | Parce et al. |
| 6,294,344 B1 | 9/2001 | O'Brien |
| 6,296,673 B1 | 10/2001 | Santarsiero et al. |
| 6,299,145 B1 | 10/2001 | Ganan-Calvo |
| 6,301,055 B1 | 10/2001 | Legrand et al. |
| 6,306,659 B1 | 10/2001 | Parce et al. |
| 6,310,354 B1 | 10/2001 | Hanninen et al. |
| 6,310,653 B1 | 10/2001 | Malcolm, Jr. et al. |
| 6,316,208 B1 | 11/2001 | Roberts et al. |
| 6,316,213 B1 | 11/2001 | O'Brien |
| 6,318,640 B1 | 11/2001 | Coffee |
| 6,336,463 B1 | 1/2002 | Ohta |
| 6,344,325 B1 | 2/2002 | Quake et al. |
| 6,352,828 B1 | 3/2002 | Brenner |
| 6,355,193 B1 | 3/2002 | Stott |
| 6,355,198 B1 | 3/2002 | Kim et al. |
| 6,357,670 B2 | 3/2002 | Ganan-Calvo |
| 6,386,463 B1 | 5/2002 | Ganan-Calvo |
| 6,391,559 B1 | 5/2002 | Brown et al. |
| 6,394,429 B2 | 5/2002 | Ganan-Calvo |
| 6,399,339 B1 | 6/2002 | Wolberg et al. |
| 6,399,389 B1 | 6/2002 | Parce et al. |
| 6,403,373 B1 | 6/2002 | Scanlan et al. |
| 6,405,936 B1 | 6/2002 | Ganan-Calvo |
| 6,408,878 B2 | 6/2002 | Unger et al. |
| 6,409,832 B2 | 6/2002 | Weigl et al. |
| 6,429,025 B1 | 8/2002 | Parce et al. |
| 6,429,148 B1 | 8/2002 | Chu et al. |
| 6,432,143 B2 | 8/2002 | Kubiak et al. |
| 6,432,148 B1 | 8/2002 | Ganan-Calvo |
| 6,432,630 B1 | 8/2002 | Blankenstein |
| 6,439,103 B1 | 8/2002 | Miller |
| 6,440,706 B1 | 8/2002 | Vogelstein et al. |
| 6,450,139 B1 | 9/2002 | Watanabe |
| 6,450,189 B1 | 9/2002 | Ganan-Calvo |
| 6,454,193 B1 | 9/2002 | Busick et al. |
| 6,464,336 B1 | 10/2002 | Sharma |
| 6,464,886 B2 | 10/2002 | Ganan-Calvo |
| 6,475,441 B1 | 11/2002 | Parce et al. |
| 6,481,648 B1 | 11/2002 | Zimmermann |
| 6,489,103 B1 * | 12/2002 | Griffiths et al. ............ 435/6.16 |
| 6,503,933 B1 | 1/2003 | Moloney et al. |
| 6,506,609 B1 | 1/2003 | Wada et al. |
| 6,508,988 B1 | 1/2003 | Van Dam et al. |
| 6,520,425 B1 | 2/2003 | Reneker |
| 6,524,456 B1 | 2/2003 | Ramsey et al. |
| 6,540,395 B2 | 4/2003 | Muhlbauer et al. |
| 6,540,895 B1 | 4/2003 | Spence et al. |
| 6,551,836 B1 | 4/2003 | Chow et al. |
| 6,553,944 B1 | 4/2003 | Allen et al. |
| 6,553,960 B1 | 4/2003 | Yoshikawa et al. |
| 6,554,202 B2 | 4/2003 | Ganan-Calvo |
| 6,557,334 B2 | 5/2003 | Jager |
| 6,557,834 B2 | 5/2003 | Ganan-Calvo |
| 6,558,944 B1 | 5/2003 | Parce et al. |
| 6,558,960 B1 | 5/2003 | Parce et al. |
| 6,560,030 B2 | 5/2003 | Legrand et al. |
| 6,565,010 B2 | 5/2003 | Anderson et al. |
| 6,569,631 B1 | 5/2003 | Pantoliano et al. |
| 6,576,420 B1 | 6/2003 | Carson et al. |
| 6,591,852 B1 | 7/2003 | McNeely et al. |
| 6,592,321 B2 | 7/2003 | Bonker et al. |
| 6,592,821 B1 | 7/2003 | Wada et al. |
| 6,608,726 B2 | 8/2003 | Legrand et al. |
| 6,610,499 B1 | 8/2003 | Fulwyler et al. |
| 6,614,598 B1 | 9/2003 | Quake et al. |
| 6,627,603 B1 | 9/2003 | Bibette et al. |
| 6,630,006 B2 | 10/2003 | Santarsiero et al. |
| 6,630,353 B1 | 10/2003 | Parce et al. |
| 6,632,619 B1 | 10/2003 | Harrison et al. |
| 6,638,749 B1 | 10/2003 | Beckman et al. |
| 6,645,432 B1 | 11/2003 | Anderson et al. |
| 6,646,253 B1 | 11/2003 | Rohwer et al. |
| 6,653,626 B2 | 11/2003 | Fischer et al. |
| 6,656,267 B2 | 12/2003 | Newman |
| 6,659,370 B1 | 12/2003 | Inoue |
| 6,660,252 B2 | 12/2003 | Matathia et al. |
| 6,670,142 B2 | 12/2003 | Lau et al. |
| 6,679,441 B1 | 1/2004 | Borra et al. |
| 6,680,178 B2 | 1/2004 | Harris et al. |
| 6,682,890 B2 | 1/2004 | Mack et al. |
| 6,717,136 B2 | 4/2004 | Andersson et al. |
| 6,729,561 B2 | 5/2004 | Hirae et al. |
| 6,739,036 B2 | 5/2004 | Koike et al. |
| 6,744,046 B2 | 6/2004 | Valaskovic et al. |
| 6,752,922 B2 | 6/2004 | Huang et al. |
| 6,753,147 B2 | 6/2004 | Vogelstein et al. |
| 6,766,817 B2 | 7/2004 | da Silva |
| 6,767,194 B2 | 7/2004 | Jeon et al. |
| 6,767,704 B2 | 7/2004 | Waldman et al. |
| 6,790,328 B2 | 9/2004 | Jacobson et al. |
| 6,793,753 B2 | 9/2004 | Unger et al. |
| 6,797,056 B2 | 9/2004 | David |
| 6,800,849 B2 | 10/2004 | Staats |
| 6,806,058 B2 | 10/2004 | Jesperson et al. |
| 6,808,382 B2 | 10/2004 | Lanfranchi |
| 6,808,882 B2 | 10/2004 | Griffiths et al. |
| 6,814,980 B2 * | 11/2004 | Levy et al. ............ 424/497 |
| 6,818,395 B1 | 11/2004 | Quake et al. |
| 6,832,787 B1 | 12/2004 | Renzi |
| 6,833,242 B2 | 12/2004 | Quake et al. |
| 6,841,350 B2 | 1/2005 | Ogden et al. |
| 6,872,250 B2 | 3/2005 | David et al. |
| 6,890,487 B1 | 5/2005 | Sklar et al. |
| 6,897,018 B1 | 5/2005 | Yuan et al. |
| 6,905,844 B2 | 6/2005 | Kim |
| 6,918,404 B2 | 7/2005 | Dias da Silva |
| 6,926,313 B1 | 8/2005 | Renzi |
| 6,935,768 B2 | 8/2005 | Lowe et al. |
| 6,936,417 B2 | 8/2005 | Orntoft |
| 6,942,978 B1 | 9/2005 | O'Brien |
| 6,949,342 B2 | 9/2005 | Golub et al. |
| 6,960,437 B2 | 11/2005 | Enzelberger et al. |
| 6,974,667 B2 | 12/2005 | Horne et al. |
| 6,998,232 B1 | 2/2006 | Feinstein et al. |
| 7,022,472 B2 | 4/2006 | Robbins et al. |
| 7,041,481 B2 | 5/2006 | Anderson et al. |
| 7,049,072 B2 | 5/2006 | Seshi |
| 7,056,674 B2 | 6/2006 | Baker et al. |
| 7,057,026 B2 | 6/2006 | Barnes et al. |
| 7,066,586 B2 | 6/2006 | da Silva |

(56) References Cited

U.S. PATENT DOCUMENTS

| | | |
|---|---|---|
| 7,068,874 B2 | 6/2006 | Wang et al. |
| 7,078,180 B2 | 7/2006 | Genetta |
| 7,081,192 B1 | 7/2006 | Wang et al. |
| 7,081,340 B2 | 7/2006 | Baker et al. |
| 7,090,983 B1 | 8/2006 | Muramatsu et al. |
| 7,115,230 B2 | 10/2006 | Sundararajan et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,153,700 B1 | 12/2006 | Pardee et al. |
| 7,156,917 B2 | 1/2007 | Moriyama et al. |
| 7,163,801 B2 | 1/2007 | Reed |
| 7,169,560 B2 | 1/2007 | Lapidus et al. |
| 7,171,311 B2 | 1/2007 | Dai et al. |
| 7,198,899 B2 | 4/2007 | Schleyer et al. |
| 7,204,431 B2 | 4/2007 | Li et al. |
| 7,229,770 B1 | 6/2007 | Price et al. |
| 7,252,943 B2 | 8/2007 | Griffiths et al. |
| 7,267,938 B2 | 9/2007 | Anderson et al. |
| 7,268,167 B2 | 9/2007 | Higuchi et al. |
| 7,282,337 B1 | 10/2007 | Harris |
| 7,291,462 B2 | 11/2007 | O'Brien et al. |
| 7,294,503 B2 | 11/2007 | Quake et al. |
| 7,300,765 B2 | 11/2007 | Patel |
| 7,308,364 B2 | 12/2007 | Shaughnessy et al. |
| 7,314,721 B2 | 1/2008 | Gure et al. |
| 7,316,906 B2 | 1/2008 | Chiorazzi et al. |
| 7,326,529 B2 | 2/2008 | Ali et al. |
| 7,332,280 B2 | 2/2008 | Levy et al. |
| 7,332,590 B2 | 2/2008 | Nacht et al. |
| 7,341,211 B2 | 3/2008 | Ganan Calvo et al. |
| 7,348,142 B2 | 3/2008 | Wang |
| 7,358,231 B1 | 4/2008 | McCaffey et al. |
| 7,361,474 B2 | 4/2008 | Siegler |
| 7,364,862 B2 | 4/2008 | Ali et al. |
| 7,368,255 B2 | 5/2008 | Bae et al. |
| 7,378,233 B2 | 5/2008 | Sidransky et al. |
| 7,378,280 B2 | 5/2008 | Quake et al. |
| 7,390,463 B2 | 6/2008 | He et al. |
| 7,393,665 B2 | 7/2008 | Brenner |
| 7,416,851 B2 | 8/2008 | Davi et al. |
| 7,429,467 B2 | 9/2008 | Holliger et al. |
| 7,432,064 B2 | 10/2008 | Salceda et al. |
| 7,442,507 B2 | 10/2008 | Polsky et al. |
| 7,449,303 B2 | 11/2008 | Coignet |
| 7,468,271 B2 | 12/2008 | Golovchenko et al. |
| 7,473,530 B2 | 1/2009 | Huttemann |
| 7,473,531 B1 | 1/2009 | Domon et al. |
| 7,476,506 B2 | 1/2009 | Schleyer et al. |
| 7,479,370 B2 | 1/2009 | Coignet |
| 7,479,371 B2 | 1/2009 | Ando et al. |
| 7,479,376 B2 | 1/2009 | Waldman et al. |
| 7,482,129 B2 | 1/2009 | Soyupak et al. |
| 7,501,244 B2 | 3/2009 | Reinhard et al. |
| 7,504,214 B2 | 3/2009 | Erlander et al. |
| 7,507,532 B2 | 3/2009 | Chang et al. |
| 7,507,541 B2 | 3/2009 | Raitano et al. |
| 7,510,707 B2 | 3/2009 | Platica et al. |
| 7,510,842 B2 | 3/2009 | Podust et al. |
| 7,514,209 B2 | 4/2009 | Dai et al. |
| 7,514,210 B2 | 4/2009 | Holliger et al. |
| 7,524,633 B2 | 4/2009 | Sidransky |
| 7,527,933 B2 | 5/2009 | Sahin et al. |
| 7,537,897 B2 | 5/2009 | Brenner et al. |
| 7,541,383 B2 | 6/2009 | Fu et al. |
| 7,544,473 B2 | 6/2009 | Brenner |
| 7,556,776 B2 | 7/2009 | Fraden et al. |
| 7,582,446 B2 | 9/2009 | Griffiths et al. |
| 7,622,081 B2 | 11/2009 | Chou et al. |
| 7,632,562 B2 | 12/2009 | Nair et al. |
| 7,635,562 B2 | 12/2009 | Harris et al. |
| 7,638,276 B2 | 12/2009 | Griffiths et al. |
| 7,655,435 B2 | 2/2010 | Holliger et al. |
| 7,655,470 B2 | 2/2010 | Ismagilov et al. |
| 7,666,593 B2 | 2/2010 | Lapidus |
| 7,691,576 B2 | 4/2010 | Holliger et al. |
| 7,698,287 B2 | 4/2010 | Becker et al. |
| 7,708,949 B2 | 5/2010 | Stone et al. |
| 7,718,578 B2 | 5/2010 | Griffiths et al. |
| 7,736,890 B2 | 6/2010 | Sia et al. |
| 7,741,130 B2 | 6/2010 | Lee, Jr. et al. |
| 7,814,175 B1 | 10/2010 | Chang et al. |
| 7,824,889 B2 | 11/2010 | Vogelstein et al. |
| 7,897,044 B2 | 3/2011 | Hoyos et al. |
| 7,897,341 B2 | 3/2011 | Griffiths et al. |
| 7,901,939 B2 | 3/2011 | Ismagliov et al. |
| 7,968,287 B2 | 6/2011 | Griffiths et al. |
| 8,012,382 B2 | 9/2011 | Kim et al. |
| 8,153,402 B2 | 4/2012 | Holliger et al. |
| 2001/0010338 A1 | 8/2001 | Ganan-Calvo |
| 2001/0020011 A1 | 9/2001 | Mathiowitz et al. |
| 2001/0023078 A1 | 9/2001 | Bawendi et al. |
| 2001/0029983 A1 | 10/2001 | Unger et al. |
| 2001/0034031 A1 | 10/2001 | Short et al. |
| 2001/0041343 A1 | 11/2001 | Pankowsky |
| 2001/0041344 A1 | 11/2001 | Sepetov et al. |
| 2001/0042793 A1 | 11/2001 | Ganan-Calvo |
| 2001/0048900 A1 | 12/2001 | Bardell et al. |
| 2001/0050881 A1 | 12/2001 | Depaoli et al. |
| 2002/0004532 A1 | 1/2002 | Matathia et al. |
| 2002/0005354 A1 | 1/2002 | Spence et al. |
| 2002/0008028 A1 | 1/2002 | Jacobson et al. |
| 2002/0012971 A1 | 1/2002 | Mehta |
| 2002/0022038 A1 | 2/2002 | Biatry et al. |
| 2002/0022261 A1 | 2/2002 | Anderson et al. |
| 2002/0033422 A1 | 3/2002 | Ganan-Calvo |
| 2002/0036139 A1 | 3/2002 | Becker et al. |
| 2002/0058332 A1 | 5/2002 | Quake et al. |
| 2002/0067800 A1 | 6/2002 | Newman et al. |
| 2002/0119459 A1* | 8/2002 | Griffiths ............ 435/6 |
| 2002/0143437 A1 | 10/2002 | Handique et al. |
| 2002/0155080 A1 | 10/2002 | Glenn et al. |
| 2002/0158027 A1 | 10/2002 | Moon et al. |
| 2002/0164271 A1 | 11/2002 | Ho |
| 2002/0164629 A1 | 11/2002 | Quake et al. |
| 2003/0012586 A1 | 1/2003 | Iwata et al. |
| 2003/0015425 A1 | 1/2003 | Bohm et al. |
| 2003/0017579 A1 | 1/2003 | Corn et al. |
| 2003/0039169 A1 | 2/2003 | Ehrfeld et al. |
| 2003/0059764 A1 | 3/2003 | Ravkin et al. |
| 2003/0061687 A1 | 4/2003 | Hansen et al. |
| 2003/0064414 A1 | 4/2003 | Benecky et al. |
| 2003/0082795 A1 | 5/2003 | Shuler et al. |
| 2003/0124586 A1 | 7/2003 | Griffiths et al. |
| 2003/0144260 A1 | 7/2003 | Gilon |
| 2003/0148544 A1 | 8/2003 | Nie et al. |
| 2003/0183525 A1 | 10/2003 | Elrod et al. |
| 2003/0224509 A1 | 12/2003 | Moon et al. |
| 2003/0229376 A1 | 12/2003 | Sandhu |
| 2003/0230486 A1 | 12/2003 | Chien et al. |
| 2003/0230819 A1* | 12/2003 | Park ............. A61L 31/16 264/4 |
| 2003/0232356 A1 | 12/2003 | Dooley et al. |
| 2004/0005582 A1 | 1/2004 | Shipwash |
| 2004/0005594 A1 | 1/2004 | Holliger et al. |
| 2004/0018525 A1 | 1/2004 | Wirtz et al. |
| 2004/0027915 A1 | 2/2004 | Lowe et al. |
| 2004/0037813 A1 | 2/2004 | Simpson et al. |
| 2004/0041093 A1 | 3/2004 | Schultz et al. |
| 2004/0050946 A1 | 3/2004 | Wang et al. |
| 2004/0053247 A1 | 3/2004 | Cordon-Cardo et al. |
| 2004/0068019 A1 | 4/2004 | Higuchi et al. |
| 2004/0071781 A1 | 4/2004 | Chattopadhyay et al. |
| 2004/0079881 A1 | 4/2004 | Fischer et al. |
| 2004/0096515 A1 | 5/2004 | Bausch et al. |
| 2004/0136497 A1 | 7/2004 | Meldrum et al. |
| 2004/0146921 A1 | 7/2004 | Eveleigh et al. |
| 2004/0159633 A1 | 8/2004 | Whitesides et al. |
| 2004/0181131 A1 | 9/2004 | Maynard et al. |
| 2004/0181343 A1 | 9/2004 | Wigstrom et al. |
| 2004/0182712 A1 | 9/2004 | Basol |
| 2004/0188254 A1 | 9/2004 | Spaid |
| 2004/0224419 A1 | 11/2004 | Zheng et al. |
| 2004/0253731 A1 | 12/2004 | Holliger et al. |

(56) References Cited

U.S. PATENT DOCUMENTS

| | | |
|---|---|---|
| 2004/0258203 A1 | 12/2004 | Yamano et al. |
| 2005/0032238 A1 | 2/2005 | Karp et al. |
| 2005/0032240 A1 | 2/2005 | Lee et al. |
| 2005/0037392 A1 | 2/2005 | Griffiths et al. |
| 2005/0042648 A1 | 2/2005 | Griffiths et al. |
| 2005/0048467 A1 | 3/2005 | Sastry et al. |
| 2005/0064460 A1 | 3/2005 | Holliger et al. |
| 2005/0069920 A1 | 3/2005 | Griffiths et al. |
| 2005/0079510 A1 | 4/2005 | Berka et al. |
| 2005/0084923 A1 | 4/2005 | Mueller et al. |
| 2005/0087122 A1 | 4/2005 | Ismagliov et al. |
| 2005/0095611 A1 | 5/2005 | Chan et al. |
| 2005/0100895 A1 | 5/2005 | Waldman et al. |
| 2005/0129582 A1 | 6/2005 | Breidford et al. |
| 2005/0152908 A1 | 7/2005 | Liew et al. |
| 2005/0164239 A1 | 7/2005 | Griffiths et al. |
| 2005/0170431 A1 | 8/2005 | Ibrahim et al. |
| 2005/0172476 A1 | 8/2005 | Stone et al. |
| 2005/0183995 A1 | 8/2005 | Deshpande et al. |
| 2005/0207940 A1 | 9/2005 | Butler et al. |
| 2005/0221339 A1 | 10/2005 | Griffiths et al. |
| 2005/0226742 A1 | 10/2005 | Unger et al. |
| 2005/0227264 A1 | 10/2005 | Nobile et al. |
| 2005/0260566 A1 | 11/2005 | Fischer et al. |
| 2005/0272159 A1 | 12/2005 | Ismagilov et al. |
| 2006/0003347 A1 | 1/2006 | Griffiths et al. |
| 2006/0003429 A1 | 1/2006 | Frost et al. |
| 2006/0003439 A1 | 1/2006 | Ismagilov et al. |
| 2006/0036348 A1 | 2/2006 | Handique et al. |
| 2006/0046257 A1 | 3/2006 | Pollock et al. |
| 2006/0051329 A1 | 3/2006 | Lee et al. |
| 2006/0078888 A1 | 4/2006 | Griffiths et al. |
| 2006/0078893 A1 | 4/2006 | Griffiths et al. |
| 2006/0094119 A1 | 5/2006 | Ismagilov et al. |
| 2006/0108012 A1 | 5/2006 | Barrow et al. |
| 2006/0110759 A1 | 5/2006 | Paris et al. |
| 2006/0115821 A1 | 6/2006 | Einstein et al. |
| 2006/0147909 A1 | 7/2006 | Rarbach et al. |
| 2006/0153924 A1 | 7/2006 | Griffiths et al. |
| 2006/0154298 A1 | 7/2006 | Griffiths et al. |
| 2006/0160762 A1 | 7/2006 | Zetter et al. |
| 2006/0163385 A1 | 7/2006 | Link et al. |
| 2006/0169800 A1 | 8/2006 | Rosell et al. |
| 2006/0195269 A1 | 8/2006 | Yeatman et al. |
| 2006/0223127 A1 | 10/2006 | Yip et al. |
| 2006/0234254 A1 | 10/2006 | An et al. |
| 2006/0234259 A1 | 10/2006 | Rubin et al. |
| 2006/0252057 A1 | 11/2006 | Raponi et al. |
| 2006/0258841 A1 | 11/2006 | Michl et al. |
| 2006/0263888 A1 | 11/2006 | Fritz et al. |
| 2006/0269558 A1 | 11/2006 | Murphy et al. |
| 2006/0269971 A1 | 11/2006 | Diamandis |
| 2006/0281089 A1 | 12/2006 | Gibson et al. |
| 2007/0003442 A1 | 1/2007 | Link et al. |
| 2007/0026439 A1 | 2/2007 | Faulstich et al. |
| 2007/0053896 A1 | 3/2007 | Ahmed et al. |
| 2007/0054119 A1 | 3/2007 | Garstecki et al. |
| 2007/0056853 A1 | 3/2007 | Aizenberg et al. |
| 2007/0077572 A1 | 4/2007 | Tawfik et al. |
| 2007/0077579 A1 | 4/2007 | Griffiths et al. |
| 2007/0092914 A1 | 4/2007 | Griffiths et al. |
| 2007/0120899 A1 | 5/2007 | Ohnishi et al. |
| 2007/0154889 A1 | 7/2007 | Wang |
| 2007/0166705 A1 | 7/2007 | Milton et al. |
| 2007/0184439 A1 | 8/2007 | Guilford et al. |
| 2007/0184489 A1 | 8/2007 | Griffiths et al. |
| 2007/0195127 A1 | 8/2007 | Ahn et al. |
| 2007/0259351 A1 | 11/2007 | Chinitz et al. |
| 2007/0259368 A1 | 11/2007 | An et al. |
| 2007/0259374 A1 | 11/2007 | Griffiths et al. |
| 2007/0292869 A1 | 12/2007 | Becker et al. |
| 2008/0003142 A1 | 1/2008 | Link et al. |
| 2008/0009005 A1 | 1/2008 | Kruk |
| 2008/0014589 A1 | 1/2008 | Link et al. |
| 2008/0014590 A1 | 1/2008 | Dahary et al. |
| 2008/0020940 A1 | 1/2008 | Stedronsky et al. |
| 2008/0021330 A1 | 1/2008 | Hwang et al. |
| 2008/0023330 A1 | 1/2008 | Viovy et al. |
| 2008/0038754 A1 | 2/2008 | Farias-Eisner et al. |
| 2008/0044828 A1 | 2/2008 | Kwok |
| 2008/0050378 A1 | 2/2008 | Nakamura et al. |
| 2008/0050723 A1 | 2/2008 | Belacel et al. |
| 2008/0053205 A1 | 3/2008 | Pollack et al. |
| 2008/0057514 A1 | 3/2008 | Goldenring |
| 2008/0058432 A1 | 3/2008 | Wang et al. |
| 2008/0063227 A1 | 3/2008 | Rohrseitz |
| 2008/0064047 A1 | 3/2008 | Zetter et al. |
| 2008/0081330 A1 | 4/2008 | Kahvejian |
| 2008/0081333 A1 | 4/2008 | Mori et al. |
| 2008/0092973 A1 | 4/2008 | Lai |
| 2008/0113340 A1 | 5/2008 | Schlegel |
| 2008/0118462 A1 | 5/2008 | Alani et al. |
| 2008/0138806 A1 | 6/2008 | Chow et al. |
| 2008/0166772 A1 | 7/2008 | Hollinger et al. |
| 2008/0171078 A1 | 7/2008 | Gray |
| 2008/0176211 A1 | 7/2008 | Spence et al. |
| 2008/0176236 A1 | 7/2008 | Tsao et al. |
| 2008/0181850 A1 | 7/2008 | Thaxton et al. |
| 2008/0206756 A1 | 8/2008 | Lee et al. |
| 2008/0222741 A1 | 9/2008 | Chinnaiyan |
| 2008/0234138 A1 | 9/2008 | Shaughnessy et al. |
| 2008/0234139 A1 | 9/2008 | Shaughnessy et al. |
| 2008/0268473 A1 | 10/2008 | Moses et al. |
| 2008/0269157 A1 | 10/2008 | Srivastava et al. |
| 2008/0274908 A1 | 11/2008 | Chang |
| 2008/0280302 A1 | 11/2008 | Kebebew |
| 2008/0286199 A1 | 11/2008 | Livingston et al. |
| 2008/0286801 A1 | 11/2008 | Arjol et al. |
| 2008/0286811 A1 | 11/2008 | Moses et al. |
| 2008/0293578 A1 | 11/2008 | Shaugnessy et al. |
| 2008/0311570 A1 | 12/2008 | Lai |
| 2008/0311604 A1 | 12/2008 | Elting et al. |
| 2009/0004687 A1 | 1/2009 | Mansfield et al. |
| 2009/0005254 A1 | 1/2009 | Griffiths et al. |
| 2009/0012187 A1 | 1/2009 | Chu et al. |
| 2009/0017463 A1 | 1/2009 | Bhowmick |
| 2009/0021728 A1 | 1/2009 | Heinz et al. |
| 2009/0023137 A1 | 1/2009 | Van Der Zee et al. |
| 2009/0026082 A1 | 1/2009 | Rothberg et al. |
| 2009/0029372 A1 | 1/2009 | Wewer |
| 2009/0042737 A1 | 2/2009 | Katz et al. |
| 2009/0053700 A1 | 2/2009 | Griffiths et al. |
| 2009/0053732 A1 | 2/2009 | Vermesh et al. |
| 2009/0060797 A1 | 3/2009 | Mathies et al. |
| 2009/0062144 A1 | 3/2009 | Guo |
| 2009/0068170 A1 | 3/2009 | Weitz et al. |
| 2009/0075265 A1 | 3/2009 | Budiman et al. |
| 2009/0075307 A1 | 3/2009 | Fischer et al. |
| 2009/0075311 A1 | 3/2009 | Karl |
| 2009/0081237 A1 | 3/2009 | D'Andrea et al. |
| 2009/0081685 A1 | 3/2009 | Beyer et al. |
| 2009/0087849 A1 | 4/2009 | Malinowski et al. |
| 2009/0092973 A1 | 4/2009 | Erlander et al. |
| 2009/0098542 A1 | 4/2009 | Budiman et al. |
| 2009/0098543 A1 | 4/2009 | Budiman et al. |
| 2009/0118128 A1 | 5/2009 | Liu et al. |
| 2009/0124569 A1 | 5/2009 | Bergan et al. |
| 2009/0127454 A1 | 5/2009 | Ritchie et al. |
| 2009/0127589 A1 | 5/2009 | Rothberg et al. |
| 2009/0131353 A1 | 5/2009 | Insel et al. |
| 2009/0131543 A1 | 5/2009 | Weitz et al. |
| 2009/0191565 A1 | 7/2009 | Lapidus et al. |
| 2009/0197248 A1 | 8/2009 | Griffiths et al. |
| 2009/0197772 A1 | 8/2009 | Griffiths et al. |
| 2009/0246788 A1 | 10/2009 | Albert et al. |
| 2009/0325236 A1 | 12/2009 | Griffiths et al. |
| 2010/0003687 A1 | 1/2010 | Simen et al. |
| 2010/0009353 A1 | 1/2010 | Barnes et al. |
| 2010/0022414 A1 | 1/2010 | Link et al. |
| 2010/0035252 A1 | 2/2010 | Rothberg et al. |
| 2010/0075436 A1 | 3/2010 | Urdea et al. |
| 2010/0105112 A1 | 4/2010 | Holtze et al. |
| 2010/0111768 A1 | 5/2010 | Banerjee et al. |
| 2010/0124759 A1 | 5/2010 | Wang et al. |

(56) References Cited

U.S. PATENT DOCUMENTS

| | | |
|---|---|---|
| 2010/0136544 A1 | 6/2010 | Agresti et al. |
| 2010/0137143 A1 | 6/2010 | Rothberg et al. |
| 2010/0137163 A1 | 6/2010 | Link et al. |
| 2010/0159592 A1 | 6/2010 | Holliger et al. |
| 2010/0172803 A1 | 7/2010 | Stone et al. |
| 2010/0188073 A1 | 7/2010 | Rothberg et al. |
| 2010/0197507 A1 | 8/2010 | Rothberg et al. |
| 2010/0210479 A1 | 8/2010 | Griffiths et al. |
| 2010/0213628 A1 | 8/2010 | Bausch et al. |
| 2010/0233026 A1 | 9/2010 | Ismagliov et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0000560 A1 | 1/2011 | Miller et al. |
| 2011/0142734 A1 | 6/2011 | Ismagliov et al. |
| 2011/0174622 A1 | 7/2011 | Ismagliov et al. |
| 2011/0176966 A1 | 7/2011 | Ismagliov et al. |
| 2011/0177494 A1 | 7/2011 | Ismagliov et al. |
| 2011/0177586 A1 | 7/2011 | Ismagliov et al. |
| 2011/0177609 A1 | 7/2011 | Ismagliov et al. |
| 2011/0188717 A1 | 8/2011 | Baudry et al. |
| 2011/0190146 A1 | 8/2011 | Boehm et al. |
| 2011/0244455 A1 | 10/2011 | Larson et al. |
| 2011/0250597 A1 | 10/2011 | Larson et al. |
| 2011/0275063 A1 | 11/2011 | Weitz et al. |
| 2012/0010098 A1 | 1/2012 | Griffiths et al. |
| 2012/0015382 A1 | 1/2012 | Weitz et al. |
| 2012/0015822 A1 | 1/2012 | Weitz et al. |

FOREIGN PATENT DOCUMENTS

| | | |
|---|---|---|
| CH | 563807 A5 | 7/1975 |
| DE | 4308839 C2 | 4/1997 |
| EP | 0047130 B1 | 2/1985 |
| EP | 0249007 A3 | 3/1991 |
| EP | 0476178 A1 | 3/1992 |
| EP | 0540281 B1 | 7/1996 |
| EP | 0528580 B1 | 12/1996 |
| EP | 0895120 | 2/1999 |
| EP | 1741482 | 1/2007 |
| EP | 2127736 | 12/2009 |
| GB | 0114854.3 | 4/1969 |
| GB | 1446998 | 8/1976 |
| GB | 2005224 | 4/1979 |
| GB | 2047880 | 12/1980 |
| GB | 2062225 | 5/1981 |
| GB | 2064114 | 6/1981 |
| GB | 2097692 A | 11/1982 |
| GB | 0221053.2 | 6/1989 |
| WO | WO-84/02000 | 5/1984 |
| WO | WO-91/05058 A1 | 4/1991 |
| WO | WO-91/07772 | 5/1991 |
| WO | WO-92/03734 | 3/1992 |
| WO | WO-92/21746 | 12/1992 |
| WO | WO-93/03151 | 2/1993 |
| WO | WO-93/08278 | 4/1993 |
| WO | WO-93/22053 | 11/1993 |
| WO | WO-93/22054 | 11/1993 |
| WO | WO-93/22055 | 11/1993 |
| WO | WO-93/22058 | 11/1993 |
| WO | WO-93/22421 | 11/1993 |
| WO | WO-94/16332 | 7/1994 |
| WO | WO-94/23738 | 10/1994 |
| WO | WO-94/24314 | 10/1994 |
| WO | WO-94/26766 | 11/1994 |
| WO | WO-98/00705 | 1/1995 |
| WO | WO-95/11922 | 5/1995 |
| WO | WO-95/19922 | 7/1995 |
| WO | WO-95/24929 | 9/1995 |
| WO | WO-95/33447 | 12/1995 |
| WO | WO-96/34112 | 10/1996 |
| WO | WO-96/38730 | 12/1996 |
| WO | WO-96/40062 | 12/1996 |
| WO | WO-96/40723 | 12/1996 |
| WO | WO-97/00125 | 1/1997 |
| WO | WO-97/00442 | 1/1997 |
| WO | WO-97/04297 | 2/1997 |
| WO | WO-97/04748 | 2/1997 |
| WO | WO-97/23140 | 7/1997 |
| WO | WO-97/28556 | 8/1997 |
| WO | WO-97/39814 | 10/1997 |
| WO | WO-97/40141 | 10/1997 |
| WO | WO-97/45644 | 12/1997 |
| WO | WO-97/47763 | 12/1997 |
| WO | WO-98/00231 | 1/1998 |
| WO | WO-98/02237 | 1/1998 |
| WO | WO-98/10267 | 3/1998 |
| WO | WO-98/13502 | 4/1998 |
| WO | WO-98/23733 | 6/1998 |
| WO | WO-98/31700 | 7/1998 |
| WO | WO-98/33001 | 7/1998 |
| WO | WO-98/34120 | 8/1998 |
| WO | WO-98/37186 | 8/1998 |
| WO | WO-98/41869 | 9/1998 |
| WO | WO-98/52691 | 11/1998 |
| WO | WO-98/58085 | 12/1998 |
| WO | WO 99/02671 * 1/1999 | ............ C12N 15/10 |
| WO | WO-99/02671 | 1/1999 |
| WO | WO 9902671 A1 * 1/1999 | |
| WO | WO-99/22858 | 5/1999 |
| WO | WO-99/28020 | 6/1999 |
| WO | WO-99/31019 | 6/1999 |
| WO | WO-00/04139 | 7/1999 |
| WO | WO-99/54730 | 10/1999 |
| WO | WO-99/61888 | 12/1999 |
| WO | WO-00/47322 | 2/2000 |
| WO | WO-00/52455 | 2/2000 |
| WO | WO-00/40712 | 6/2000 |
| WO | WO-00/61275 | 10/2000 |
| WO | WO-00/70080 | 11/2000 |
| WO | WO-00/76673 | 12/2000 |
| WO | WO-01/12327 | 2/2001 |
| WO | WO-01/14589 | 3/2001 |
| WO | WO-01/18244 | 3/2001 |
| WO | WO-01/64332 | 9/2001 |
| WO | WO-01/68257 | 9/2001 |
| WO | WO-01/69289 | 9/2001 |
| WO | WO-01/72431 | 10/2001 |
| WO | WO-01/80283 | 10/2001 |
| WO | WO-02/18949 | 3/2002 |
| WO | WO-02/22869 | 3/2002 |
| WO | WO-02/23163 | 3/2002 |
| WO | WO-02/31203 | 4/2002 |
| WO | WO-02/47665 | 6/2002 |
| WO | WO-02/047665 | 8/2002 |
| WO | WO-02/060275 | 8/2002 |
| WO | WO-02/078845 | 10/2002 |
| WO | WO-02/103011 | 12/2002 |
| WO | WO-02/103363 | 12/2002 |
| WO | WO-03/011443 | 2/2003 |
| WO | WO-03/037302 | 5/2003 |
| WO | WO-03/044187 | 5/2003 |
| WO | WO-03/078659 | 9/2003 |
| WO | WO-03/099843 | 12/2003 |
| WO | WO-2004/002627 | 1/2004 |
| WO | WO-2004/018497 | 3/2004 |
| WO | WO-2004/024917 | 3/2004 |
| WO | WO-2004/038363 | 5/2004 |
| WO | WO-2004/069849 | 8/2004 |
| WO | WO-2004/074504 | 9/2004 |
| WO | WO-2004/083443 | 9/2004 |
| WO | WO-2004/087308 | 10/2004 |
| WO | WO-2004/088314 | 10/2004 |
| WO | WO-2004/091763 | 10/2004 |
| WO | WO-2004/102204 | 11/2004 |
| WO | WO-2004/103565 | 12/2004 |
| WO | WO-2005/000970 | 1/2005 |
| WO | WO-2005/002730 | 1/2005 |
| WO | WO-2005/021151 | 3/2005 |
| WO | WO 2005021151 A1 * 3/2005 | |
| WO | WO-2005/103106 | 11/2005 |
| WO | WO-2005/118138 | 12/2005 |

(56) References Cited

FOREIGN PATENT DOCUMENTS

| WO | WO-2006/002641 | 1/2006 |
|---|---|---|
| WO | WO-2006/009657 | 1/2006 |
| WO | WO-2006/027757 | 3/2006 |
| WO | WO-2006/038035 | 4/2006 |
| WO | WO-2006/040551 | 4/2006 |
| WO | WO-2006/040554 | 4/2006 |
| WO | WO-2006/078841 | 7/2006 |
| WO | WO-2006/096571 | 9/2006 |
| WO | WO-2006/101851 | 9/2006 |
| WO | WO-2007/021343 | 2/2007 |
| WO | WO-2007/030501 | 3/2007 |
| WO | WO-2007/081385 | 7/2007 |
| WO | WO-2007/081387 | 7/2007 |
| WO | WO-2007/089541 | 8/2007 |
| WO | WO-2007/114794 | 10/2007 |
| WO | WO-2007/123744 | 11/2007 |
| WO | WO-2007/133710 | 11/2007 |
| WO | WO-2007/138178 | 12/2007 |
| WO | WO-2008/021123 | 2/2008 |
| WO | WO-2008/063227 | 5/2008 |
| WO | WO-2008/097559 | 8/2008 |
| WO | WO-2008/121342 | 10/2008 |
| WO | WO-2008/130623 | 10/2008 |
| WO | WO-2009/029229 | 3/2009 |
| WO | WO-2010/056728 | 5/2010 |
| WO | WO-2010/040006 | 8/2010 |
| WO | WO-2010/151776 | 12/2010 |
| WO | WO-2011/042564 | 4/2011 |
| WO | WO-2011/079176 | 6/2011 |

OTHER PUBLICATIONS

Stapleton et al., Development of An In Vitro Compartmentalization Screen for High Throughput Directed Evolution of [FeFe] Hydrogenases, PLoS One, 2010, 5(12), 1-8.*
Holtze et al., Biocompatible Surfactants for Water-In-Fluorocarbon Emulsions, Lab on a Chip, 2008, 8(10), 1632-1639.*
Griffiths et al., Directed Evolution of an Extremely Fast Phosphotriesterase by In Vivo Compartmentalization, The EMBO Journal, 2003, 22(1), 24-35.*
Manafi, M., New Developments in Chromogenic and Fluorogenic Culture Media, International Journal of Food Microbiology, 2000, 60, 205-218.*
Sadtler et al., Reverse Water-in-Fluorocarbon Oil Emulsions as a Drug Delivery System: An In Vitro Study, Colloids and Surfaces A: Physiochemical and Engineering Aspects, 1999, 147, 309-315.*
Adang, A.E. et al., The contribution of combinatorial chemistry to lead generation: an interim analysis, Curr Med Chem 8: 985-998 (2001).
Advisory Action for U.S. Appl. No. 11/360,845, dated Jun. 14, 2010.
Advisory Action for U.S. Appl. No. 11/698,298 dated May 20, 2011.
Affholter and F. Arnold, Engineering a Revolution, Chemistry in Britain, Apr. 1999, p. 48.
Agrawal and Tang, Site-specific functionalization of oligodeoxynucleotides for non-radioactive labelling, Tetrahedron Letters 31:1543-1546 (1990).
Aharoni et al., High-Throughput screens and selections of enzyme-encoding genes, Curr Opin Chem Biol, 9(2): 210-6 (2005).
Ahn et al., Dielectrophoretic manipulation of drops for high-speed microluidic sorting devices, Applied Phys Lett 88, 024104 (2006).
Allen et al., High throughput fluorescence polarization: a homogeneous alternative to radioligand binding for cell surface receptors J Biomol Screen. 5(2):63-9 (2000).

Altman et al., Solid-state laser using a rhodamine-doped silica gel compound, IEEE Photonics technology letters 3(3):189-190 (1991).
Amstutz, P. et al., In vitro display technologies: novel developments and applications. Curr Opin Biotechnol, 12, 400-405 (2001).
Anarbaev et al., Klenow fragment and DNA polymerase alpha-primase fromserva calf thymus in water-in-oil microemulsions, Biochim Biophy Acta 1384:315-324 (1998).
Anderson et al., Preparation of a cell-free protein-synthesizing system from wheat germ, Methods Enzymol 101:635-44 (1983).
Anderson, J.E., Restriction endonucleases and modification methylases, Curr. Op. Struct. Biol., 3:24-30 (1993).
Ando, S. et al., PLGA microspheres containing plasmid DNA: preservation of supercoiled DNA via cryopreparation and carbohydrate stabilization, J Pharm Sci, 88(1):126-130 (1999).
Angell et al., Silicon micromechanical devices, Scientific American 248:44-55 (1983).
Anhuf et al., Determination of SMN1 and SMN2 copy number using TaqMan technology, Hum Mutat 22(1):74-78 (2003).
Anna et al., Formation of dispersions using flow focusing in microchannels, Applied Physics Letters,82(3): 364-366 (2003).
Arkin, M.R. et al., Probing the importance of second sphere residues in an esterolytic antibody by phage display, J Mol Biol 284(4):1083-94 (1998).
Armstrong et al., Multiple-Component Condensation Strategies for Combinatorial Library Synthesis, Acc. Chem. Res. 29(3):123-131 (1996).
Ashkin and Dziedzic, Optical trapping and manipulation of viruses and bacteria, Science 235(4795):1517-20 (1987).
Ashkin et al., Optical trapping and manipulation of single cells using infrared laser beams, Nature 330:769-771 (1987).
Atwell, S. & Wells, J.A., Selection for Improved Subtiligases by Phage Display, PNAS 96: 9497-9502(1999).
Auroux, Pierre-Alain et al., Micro Total Analysis Systems. 2. Analytical Standard Operations and Applications, Analytical Chemistry, vol. 74, No. 12, 2002, pp. 2637-2652.
Baccarani et al., Escherichia coli dihydrofolate reductase: isolation and characterization of tWO isozymes, Biochemistry 16(16):3566-72 (1977).
Baez et al., Glutathione transferases catalyse the detoxication of oxidized metabolites (o-quinones) of catecholamines and may serve as an antioxidant system preventing degenerative cellular processes, Biochem. J 324:25-28 (1997).
Baker, M., Clever PCR: more genotyping, smaller volumes, Nature Methods 7:351-356 (2010).
Ball and Schwartz, CMATRIX: software for physiologically based pharmacokinetic modeling using a symbolic matrix representation system, Comput Biol Med 24(4):269-76 (1994).
Ballantyne and Nixon, Selective Area Metallization by Electron-Beam Controlled Direct Metallic Deposition, J. Vac. Sci. Technol. 10:1094 (1973).
Barany F., The ligase chain reaction in a PCR World, PCR Methods and Applications 1(1):5-16 (1991).
Barany, F. Genetic disease detection and DNA amplification using cloned thermostable ligase, PNAS 88(1): 189-93 (1991).
Baret et al., Fluorescence-activated droplet sorting (FADS): efficient microfluidic cell sorting based on enzymatic activity, Lab on a Chip 9:1850-1858 (2009).
Baret et al., Kinetic aspects of emulsion stabilization by surfactants: a microfluidic analysis, Langmuir 25:6088-6093 (2009).
Bass et al., Hormone Phage: An Enrichment Method for Variant Proteins With Altered Binding Properties, Proteins 8:309-314(1990).
Bauer, J., Advances in cell separation: recent developments in counterflow centrifugal elutriation and continuous flow cell separation, J Chromotography, 722:55-69 (1999).
Beebe et al., Functional hydrogel structures for autonomous flow control inside microfluidic channels, Nature 404:588-590 (2000).
Beer et al., On-Chip, Real-Time, Single-Copy Polymerase Chain Reaction in Picoliter Droplets, Anal. Chem., 2007, v. 79, pp. 847-8475.
Bein, Thomas, Efficient Assays for Combinatorial methods for the Discovery of Catalysts, Agnew. Chem. Int. Ed. 38:3, 323-26 (1999).

(56) References Cited

OTHER PUBLICATIONS

Benichou et al., Double Emulsions Stabilized by New Molecular Recognition Hybrids of Natural Polymers, Polym. Adv. Tehcnol 13:1019-1031 (2002).
Benner, S.A., Expanding the genetic lexicon: incorporating non-standard amino acids into proteins by ribosome-based synthesis, Trends Biotechnol 12:158-63 (1994).
Benning, M.M. et al., The binding of substrate analogs to phosphotriesterase. J Biol Chem, 275, 30556-30560 (2000).
Berman et al., An agarose gel electrophoresis assay for the detection of DNA-binding activities in yeast cell extracts, Methods Enzymol 155:528-37 (1987).
Bernath et al, In Vitro Compartmentalization by Double Emulsions: Sorting and Gene Enrichment by Fluorescence Activated Cell Sorting, Anal. Biochem 325:151-157 (2004).
Bernath et al., Directed evolution of protein inhibitors of DNA-nucleases by in vitro compartmentalization (IVC) and nano-droplet delivery, J. Mol. Biol 345(5):1015-26 (2005).
Betlach, L. et al., A restriction endonuclease analysis of the bacterial plasmid controlling the EcoRI restriction and modification of DNA. Federation Proceedings, 35, 2037-2043 (1976).
Bibette et al., Emulsions: basic principles, Rep. Prog. Phys. 62: 969-1033 (1999).
Bico, Jose et al., Rise of Liquids and Bubbles in Angular Capillary Tubes, Journal of Colloid and Interface Science, vol. 247, 2002, pp. 162-166.
Bico, Jose et al., Self-Propelling Slugs, J. Fluid Mech., vol. 467, 2002, pp. 101-127.
Blattner and Dahlberg, RNA synthesis startpoints in bacteriophage lambda: are the promoter and operator transcribed?, Nature New Biol 237(77):227-32 (1972).
Boder et al., Yeast surface display for screening combinatorial polypeptide libraries, Nat Biotechnol 15(6):553-7 (1997).
Bougueleret, L. et al., Characterization of the gene coding for the EcoRV restriction and modification system of *Escherichia coli*, Nucleic Acids Res 12(8):3659-76 (1984).
Boyum, A., Separation of leukocytes from blood and bone marrow. Introduction, Scand J Clin Lab Invest Suppl 97:7 (1968).
Branebjerg et al., Fast mixing by lamination, MEMS Proceedings 9th Ann WO rkshop, San Diego, Feb. 11-15, 1996, 9:441-446 (1996).
Braslaysky et al., Sequence information can be obtained from single DNA molecules, PNAS 100(7):3960-3964 (2003).
Bringer et al., Microfluidic Systems for Chemical Kinetics That Rely on Chaotic Mixing in Droplets, Philos Transact A Math Phys Eng Sci 362:1-18 (2004).
Brody et al., A self-assembled microlensing rotational probe, Applied Physics Letters, 74:144-46 (1999).
Brown et al., Chemical synthesis and cloning of a tyrosine tRNA gene, Methods Enzymol 68:109-151 (1979).
Bru, R. et al., Catalytic activity of elastase in reverse micelles, Biochem Mol Bio Int, 31(4):685-92 (1993).
Bru, R. et al., Product inhibition of alpha-chymotrypsin in reverse micelles. Eur J Biochem 199(1): 95-103 (1991).
Brummelkamp et al., A system for stable expression of short interfering RNAs in mammalian cells, Science 296(5567):550-3 (2002).
Buckpitt et al.,Hepatic and pulmonary microsomal metabolism of naphthalene to glutathione adducts: factors affecting the relative rates of conjugate formation, J. Pharmacol. Exp. Ther. 231:291-300 (1984).
Buican et al., Automated single-cell manipulation and sorting by light trapping, Applied Optics 26(24):5311-5316 (1987).
Burbaum, J., Miniaturization technologies in HTS: how fast, how small, how soon? Drug Discov Today 3:313-322 (1998).
Burns et al., Microfabricated structures for integrated DNA analysis, Proc. Natl. Acad. Sci. USA, May 1996, vol. 93, pp. 5556-5561.
Burns, J.R. et al., The Intensification of Rapid Reactions in Multiphase Systems Using Slug Flow in Capillaries, Lab on a Chip, vol. 1, 2001 pp. 10-15.
Burns, Mark et al., An Integrated Nanoliter DNA Analysis Device, Science, vol. 282, 1998, pp. 484-487.
Byrnes, P.J. et al., Sensitive fluorogenic substrates for the detection of trypsin-like proteases and pancreatic elastase, Anal Biochem, 126:447 (1982).
Cahill et al., Polymerase chain reaction and Q beta replicase amplification, Clin Chem 37(9):1482-5 (1991).
Caldwell, S.R. et al., Limits of diffusion in the hydrolysis of substrates by the phosphodiesterase from Pseudomonas diminuta, Biochemistry, 30: 7438-7444 (1991).
Calvert, P., Inkjet printing for materials and devices, Chem Mater 13: 3299-3305 (2001).
Caruthers, Gene synthesis machines: DNA chemistry and its uses, Science 230:281-285 (1985).
Chakrabarti, A.C. et al., Production of RNA by a polymerase protein encapsulated within phospholipid vesicles, J Mol Evol, 39(6):555-9 (1994).
Chamberlain and Ring, Characterization of T7-specific ribonucleic acid polymerase. 1. General properties of the enzymatic reaction and the template specificity of the enzyme, J Biol Chem 248:2235-44 (1973).
Chan, Emory M. et al., Size-Controlled Growth of CdSe Nanocrystals in Microfluidic Reactors, Nano Letters, vol. 3, No. 2, 2003, pp. 199-201.
Chang and Su, Controlled double emulsification utilizing 3D PDMS microchannels, Journal of Micromechanics and Microengineering 18:1-8 (2008).
Chang, T.M., Recycling of NAD(P) by multienzyme systems immobilized by microencapsulation in artifical cells, Methods Enzymol, 136(67):67-82 (1987).
Chao et al., Control of Concentration and Volume Gradients in Microfluidic Droplet Arrays for Protein Crystallization Screening, 26th Annual International Conference of the IEEE Engineering in Medicine and Biology Society, San Francisco, California Sep. 1-5, (2004).
Chao et al., Droplet Arrays in Microfluidic Channels for Combinatorial Screening Assays, Hilton Head 2004: A Solid State Sensor, Actuator and Microsystems Workshop, Hilton Head Island, South Carolina, Jun. 6-10, (2004).
Chapman et al., In vitro selection of catalytic RNAs, Curr. op. Struct. Biol., 4:618-22 (1994).
Chayen, Crystallization with oils: a new dimension in macromolecular crystal growth Journal of Crystal Growth 196 (1999), pp. 434-441.
Chen et al., Capturing a Photoexcited Molecular Structure Through Time-Domain X-ray Absorption Fine Structure, Science 292(5515):262-264 (2001).
Chen et al., Microfluidic Switch for Embryo and Cell Sorting the 12th International Conference on Solid State Sensors, Actuators, and Microsystems, Boston, MA Jun. 8-12, 2003 Transducers, 1: 659-662 (2003).
Chen-Goodspeed et al., Structural Determinants of the substrate and stereochemical specificity of phosphotriesterase, Biochemistry, 40(5):1325-31 (2001).
Chen-Goodspeed, M. et al., Enhancement, relaxation, and reversal of the stereoselectivity for phosphotriesterase by rational evolution of active site residues, Biochemistry, 40: 1332-1339 (2001b).
Cheng, Z.,et al, Electro flow focusing inmicrofluidic devices, Microfluidics Poster, presented at DBAS, Frontiers in Nanoscience, presented Apr. 10, 2003.
Chetverin and Spirin, Replicable RNA vectors: prospects for cell-free gene amplification, expression, and cloning, Prog Nucleic Acid Res Mol Biol, 51:225-70 (1995).
Chiang, C.M. et al., Expression and purification of general transcription factors by FLAG epitope-tagging and peptide elution, Pept Res, 6: 62-64 (1993).
Chiba et al., Controlled protein delivery from biodegradable tyrosino-containing poly(anhydride-co-imide) microspheres, Biomaterials, 18(13): 893-901 (1997).
Chiou et al., A closed-cylce capillary polymerase chain reaction machine, Analytical Chemistry, American Chemical Society, 73:2018-21 (2001).

(56) References Cited

OTHER PUBLICATIONS

Chiu et al., Chemical transformations in individual ultrasmall biomimetic containers, Science, 283: 1892-1895 (1999).
Chou et al., A mirofabricated device for sizing and sorting DNA molecules 96:11-13(1998).
Clackson, T. et al., In vitro selection from protein and peptide libraries, Trends Biotechnol, 12:173-84 (1994).
Clausell-Tormos et al., Droplet-based microfluidic platforms for the encapsulation and screening of Mammalian cells and multicellular organisms, Chem Biol 15(5):427-437 (2008).
Cohen, S. et al., Controlled delivery systems for proteins based on poly(lactic/glycolic acid) microspheres, Pharm Res, 8(6):713-720 (1991).
Collins et al., Optimization of Shear Driven Droplet Generation in a Microluidic Device, ASME International Mechanical Engineering Congress and R&D Expo, Washington (2003).
Collins, J. et al., Microfluidic flow transducer based on the measurements of electrical admittance, Lab on a Chip, 4:7-10 (2004).
Compton, J., Nucleic acid sequence-based amplification, Nature, 350(6313):91-2 (1991).
Cormack, B.P. et al., FACS-optimized mutants of the green fluorescent protein (GFP), Gene 173(1):33-38 (1996).
Cortesi et al., Production of lipospheres as carriers for bioactive compounds, Biomateials, 23(11): 2283-2294 (2002).
Courrier et al., Reverse water-in-fluorocarbon emulsions and microemulsions obtained with a ?uorinated surfactant, Colloids and Surfaces A: Physicochem. Eng. Aspects 244:141-148 (2004).
Craig, D. et al., Fluorescence-based enzymatic assay by capillary electrophoresis laser-induced fluoresence detection for the determinination of a few alpha-galactosidase molecules, Anal. Biochem. 226: 147 (1995).
Creagh, A.L. et al., Structural and catalytic properties of enzymes in reverse micelles, Enzyme Microb Technol 15(5): 383-92 (1993).
Crosland-Taylor, A Device for Counting Small Particles suspended in a Fluid through a Tube, Nature 171:37-38 (1953).
Crowley, J. M., Electrical breakdown of bimolecular lipid membranes as an electromechanical instability, Biophys J. 13(7):711-724 (1973).
Cull, M.G. et al., Screening for receptor ligands using large libraries of peptides linked to the C terminus of the lac repressor, PNAS 89:1865-9 (1992).
Curran, D.P., Strategy-level separations in organic synthesis: from planning to practice. Angew Chem Int Ed, 37: 1174-11-96 (1998).
Czarnik, A.W., Encoding methods for combinatorial chemistry, Curr Opin Chem Biol 1:60-66 (1997).
Dankwardt et al., Combinatorial synthesis of small-molecule libraries using 3-amino-5-hydroxybenzoic acid, 1:113-120 (1995).
Davis, J.A. et al., Deterministic hydrodynamics: Taking blood apart, PNAS 103:14779-14784 (2006).
Davis, S.S. et al., Multiple emulsions as targetable delivery systems, Methods in Enzymology, 149: 51-64 (1987).
de Gans, B.J. et al., Inkjet printing of polymers: state of the art and future developments, Advanced materials, 16: 203-213 (2004).
De-Bashan, L. E. et al., Removal of ammonium and phosphorus ions from synthetic wastewater by the microalgae Chlorella vulgaris coimmobilized in alginate beads with the microalgae growth-promoting bacterium *Azospirillum brasilense*, Water Research 36 (2002),pp. 2941-2948.
Delagrave, S. et al., Red-shifted excitation mutants of the green fluorescent protein, Biotechnology 13(2):151-4 (1995).
DelRaso, In vitro methodologies for enhanced toxicity testing, Toxicol. Lett. 68:91-99 (1993).
Demartis et al., A strategy for the isolation of catalytic activities from repertoires of enzymes displayed on phage, J. Mol. Biol 286:617-633 (1999).
Dickinson, E., Emulsions and droplet size control, Wedlock, D.J., Ed., in Controlled Particle Droplet and Bubble Formulation, ButterWO rth-Heine-mann, 191-257 (1994).

DiMatteo, et al., Genetic conversion of an SMN2 gene to SMN1: A novel approach to the treatment of spinal muscular atrophy, Exp Cell Res. 314(4):878-886 (2008).
Dinsmore et al., Colioidosomes: Selectively Permeable Capsules Composed of Colloidal Particles, Science 298(5595):1006-1009. (2002).
Dittrich et al., A new embedded process for compartmentalized cell-free protein expression and on-line detection in microfluidic devices, Chembiochem 6(5):811-814 (2005).
Doi et al., In vitro selection of restriction endonucleases by in vitro compartmentilization, Nucleic Acids Res, 32(12): e95 (2004).
Doi, N. and Yanagawa, H. Stable: protein-DNA fusion system for screening of combinatorial protein libraries in vitro, FEBS Lett., 457: 227-230 (1999).
Doman, T.N. et al., Molecular docking and high-throughput screening for novel inhibitors of protein tyrosine phosphatase-1B, J Med Chem, 45: 2213-2221 (2002).
Domling A., Recent advances in isocyanide-based multicomponent chemistry, Curr Opin Chem Biol, 6(3):306-13 (2002).
Domling and Ugi, Multicomponent Reactions with Isocyanides, Angew Chem Int Ed 39(18):3168-3210 (2000).
Dove et al., In Brief, Nature Biotechnology 20:1213 (2002).
Dower et al., High efficiency transformation of E. coli by high voltage electroporation, Nucleic Acids Res 16:6127-6145 (1988).
Dressman et al., Transforming single DNA molecules into fluorescent magnetic particles for detection and enumeration of genetic variations, PNAS 100:8817-22 (2003).
Dreyfus et al., Ordered and disordered patterns in two phase flows in microchannels, Phys Rev Lett 90(14):144505-1-144505-4 (2003).
Drmanac et al., Sequencing by hybridization: towards an automated sequencing of one million M13 clones arrayed on membranes, Elctrophoresis 13:566-573 (1992).
Dubertret et al., In vivo imaging of quantum dots encapsulated in phospholipid micelles, Science, 298: 1759-1762 (2002).
Duffy et al., Rapid Protyping of Microfluidic Systems and Polydimethylsiloxane, Anal Chem 70:474-480 (1998).
Duggleby, R. G. Enzyme Kinetics and Mechanisms, Pt D. Academic Press 249:61-90 (1995).
Dumas, D.P., Purification and properties of the phosphotriesterase from Psuedomonas diminuta, J Biol Chem 264: 19659-19665 (1989).
Eckert and Kunkel, DNA polymerase fidelity and the polymerase chain reaction, Genome Res 1:17-24 (1991).
Edd et al., Controlled encapsulation of single-cells into monodisperse picolitre drops, Lab Chip 8(8):1262-1264 (2008).
Edel, Joshua B. et al., Microfluidic Routes to the Controlled Production of Nanopaticles, Chemical Communications, 2002 pp. 1136-1137.
Edris et al., Encapsulation of orange oil in a spray dried double emulsion, Nahrung/Food, 45(2):133-137 (2001).
Effenhauser et al., Glass chips for high-speed capillary electrophoresis separations with submicrometer plate heights, Anal Chem 65:2637-2642 (1993).
Eggers, Jens et al., Coalescence of Liquid Drops, J. Fluid Mech., vol. 401, 1999, pp. 293-310.
Ehrig, T. et al., Green-fluorescent protein mutants with altered fluorescence excitation spectra, Febs Lett, 367(2):163-66 (1995).
Eigen et al., hypercycles and compartments: compartments assists—but does not replace—hypercyclic organization of early genetic information, J Theor Biol, 85:407-11 (1980).
Eigen et al., The hypercycle: coupling of RNA and protein biosynthesis in the infection cycle of an RNA bacteriophage, Biochemistry, 30:11005-18 (1991).
Eigen, Wie entsteht information? Prinzipien der selbstorganisation in der biologie, Berichte der punsen-gesellschaft fur physikalische chemi, 80:1059-81 (1976).
Ellington and Szostak, In vitro selection of RNA molecules that bind specific ligands, Nature, 346:818-822 (1990).
Ellman et al., Biosynthetic method for introducing unnatural amino acids site-specifically into proteins, Methods Enzymol, 202:301-36 (1991).

(56) References Cited

OTHER PUBLICATIONS

Endo et al. Kinetic determination of trace cobalt by visual autocatalytic indication, Talanta 47:349-353 (1998).
Endo et al., Autocatalytic decomposition of cobalt complexes as an indicator system for the determination of trace amounts of cobalt and effectors, Analyst 121:391-394 (1996).
Eow et al., Electrocoalesce-separators for the separation of aqueous drops from a flowing dielectric viscous liquid, Separation and Purification Tech 29:63-77 (2002).
Eow et al., Electrostatic enhancement of coalescence of water droplets in oil: a review of the technology, Chemical Engineeing Journal 85:357-368 (2002).
Eow et al., Motion, deformation and break-up of aqueous drops in oils under high electric field strengths, Chemical Eng Proc 42:259-272 (2003).
Eow et al., The behavior of a liquid-liquid interface and drop-interface coalescence under the influence of an electric field, Colloids and Surfaces A: Physiochern. Eng. Aspects 215:101-123 (2003).
Eow, et al. Electrostatic and hydrodynamic separation of aqueous drops in a flowing viscous oil, Chemical Eng Proc 41:649-657 (2002).
Extended European Search Report for EP 10181911.8 dated Jun. 1, 2011 (7 pages).
Extended European Search Report for EP 10184514.7 dated Dec. 20, 2010 (5 pages).
Faca et al., A mouse to human search for plasma proteome changes associated with pancreatic tumor development, PLoS Med 5(6):e123 (2008).
Fahy et al., Self-sustained sequence replication (3SR): an isothermal transcription-based amplification system alternative to PCR, PCR Methods Appl 1:25-33 (1991).
Fan and Harrison, Micromachining of capillary electrophoresis injectors and separators on glass chips and evaluation of flow at capillary intersections, Anal Chem 66:177-184 (1994).
Fastrez, J., In vivo versus in vitro screening or selection for catalytic activity in enzymes and abzymes, Mol Biotechnol 7(1):37-55 (1997).
Fettinger et al., Stacked modules for micro flow systems in chemical analysis: concept and studies using an enlarged model, Sens Actuat B. 17:19-25 (1993).
Fiedler et al., Dielectrophoretic sorting of particles and cells in a microsystem, Anal Chem 70(9):1909-1915 (1998).
Field, J. et al., Purification of a RAS-responsive adenylyl cyclase complex from *Saccharomyces cervisiae* by use of an epitope addition method. Mol Cell Biol, 8: 2159-2165 (1988).
Fields, S. and Song, O., A novel genetic system to detect protein-protein interactions, Nature 340(6230): 245-6 (1989).
Filella et al., TAG-72, CA 19.9 and CEA as tumor markers in gastric cancer, Acta Oncol. 33(7):747-751 (1994).
Finch, C.A., Encapsulation and controlled release, Spec Publ R Soc Chem, 138:35 (1993).
Finch, C.A., Industrial Microencapsulation: Polymers for Microcapsule Walls, 1-12 in Encapsulation and Controlled Release, Woodhead Publishing (1993).
Fire & Xu, Rolling replication of short DNA circles, PNAS 92(10):4641-5 (1995).
Firestine, S.M. et al., Using an AraC-based three hybrid system to detect biocatalysts in vivo, Nat Biotechnol 18: 544-547 (2000).
Fisch et al., A strategy of exon shuffling for making large peptide repertoires displayed on filamentous bacteriophage, PNAS 93:7761-6 (1996).
Fisher et al., Cell Encapsulation on a Microfluidic Platform, The Eighth International Conference on Miniaturised Systems for Chemistry and Life Scieces, MicroTAS 2004, Sep. 26-30, Malmo, Sweden.
Fletcher et al., Micro reactors: principles and applications in organic synthesis, Tetrahedron 58:4735-4757 (2002).
Fluri et al., Integrated capillary electrophoresis devices with an efficient postcolumn reactor in planar quartz and glass chips, Anal Chem 68:4285-4290 (1996).
Fornusek, L. et al., Polymeric microspheres as diagnostic tools for cell surface marker tracing, Crit Rev Ther Drug Carrier Syst, 2:137-74 (1986).
Fowler, Enhancement of Mixing by Droplet-Based Microfluidics, Int Conf MEMS 97-100 (2002).
Freese, E., The specific mutagenic effect of base analogues on Phage T4, J Mol Biol, 1: 87 (1959).
Frenz et al., Reliable microfluidic on-chip incubation of droplets in delay-lines, Lab on a Chip 9:1344-1348 (2008).
Fu et al., A microfabricated fluorescence-activated cell sorter, Nature Biotechnology, 17(11):1109-1111 (1999).
Fu et al., An Integrated Microfabricated Cell Sorter, Anal. Chem., 74: 2451-2457 (2002).
Fulton et al., Advanced multiplexed analysis with the FlowMetrix system, Clin Chem 43:1749-1756 (1997).
Fulwyler, Electronic Separation of Biological Cells by Volume, Science 150(3698):910-911 (1965).
Gallarate et al., On the stability of ascorbic acid in emulsified systems for topical and cosmetic use, Int J Pharm 188(2):233-241 (1999).
Ganan-Calvo, A.M., Perfectly Monodisperse Microbubbling by Capillary Flow Focusing, Phys Rev Lett 87(27): 274501-1-4 (2001).
Ganan-Calvo, Generation of Steady Liquid Microthreads and Micron-Sized Monodisperse Sprays and Gas Streams, Phys Rev Lett 80(2):285-288 (1998).
Garcia-Ruiz et al. A super-saturation wave of protein crystallization, J. Crystal Growth, 2001, v232, pp. 149-155.
Garcia-Ruiz et al., Investigation on protein crystal growth by the gel acupuncture method{, Acta, Cryst., 1994, D50, 99. pp. 484-490.
Garstecki, et al., Formation of monodisperse bubbles in a microfiuidic flow-focusing device, Appl Phys Lett 85(13):2649-2651 (2004).
Gasperlin et al., The structure elucidation of semisolid w/o emulsion systems containing silicone surfactant, Intl J Pharm, 107:51-6 (1994).
Gasperlin et al., Viscosity prediction of lipophillic semisolid emulsion systems by neural network modeling, Intl J Pharm, 196:37-50 (2000).
Georgiou et al., Display of heterologous proteins on the surface of microorganisms: from the screenign of combinatiorial libraires to live recombinant vaccines. Nat Biotechnol 15(1), 29-34 (1997).
Georgiou, G., Analysis of large libraries of protein mutants using flow cytometry, Adv Protein Chem, 55: 293-315 (2000).
Gerdts et al., A Synthetic Reaction NetWork: Chemical Amplification Using Nonequilibrium Autocatalytic Reactions Coupled in Time, J. Am. Chem. Soc 126:6327-6331 (2004).
Ghadessy et al., Directed Evolution of Polymerase Function by Compartmentalized Self-Replication, PNSAS 98(8): 4552-4557 (2001).
Gibbs et al., Detection of single DNA base differences by competitive oligonucleotide priming, Nucleic Acids Res. 17(7): 2437-48 (1989).
Gilliland, G., Analysis of cytokine mRNA and DNA: Detection and quantitation by competitive polymerase chain reaction, PNAS, 87(7):2725-9 (1990).
Giusti et al., Synthesis and characterization of 5' fluorescent dye labeled oligonucleotides, Genome Res 2:223-227 (1993).
Gold et al., Diversity of Oligonucleotide Functions Annu Rev Biochem, 64: 763-97 (1995).
Goodall, J. L. et al., Operation of Mixed-Culture Immobilized Cell Reactors for the Metabolism of Meta- and Para-Nitrobenzoate by *Comamonas* Sp. JS46 and *Comamonas* Sp. JS47, Biotechnology and Bioengineering, vol. 59, No. 1, Jul. 5, 1998, pp. 21-27.
Gordon and Balasubramanian, Solid phase synthesis—designer linkers for combinatorial chemistry: a review, J. Chem. Technol. Biotechnol., 74(9):835-851 (1999).
Grasland-Mongrain et al., Droplet coalescence in microfluidic devices, 30 pages (Jul. 2003) From internet: http://www.eleves.ens.fr/home/grasland/rapports/stage4.pdf.

(56) References Cited

OTHER PUBLICATIONS

Green, R. and Szostak, J.W., Selection of a Ribozyme That Functions as a Superior Template in a Self Copying Reaction, Science, 258: 1910-5 (1992).
Gregoriadis, G., Enzyme entrapment in liposomes, Methods Enzymol 44:218-227 (1976).
Griffiths et al., Directed evolution of an extremely fast phosphotriesterase by in vitro compartmentalization, EMBO J, 22:24-35 (2003).
Griffiths et al., Isolation of high affinity human antibodies directly from large synthetic repertoires, Embo J 13(14):3245-60 (1994).
Griffiths et al., Man-made enzymes-from design to in vitro compartmentalisation, Curr Opin Biotechnol 11:338-353 (2000).
Griffiths, A., and Tawfik, D., Miniaturising the laboratory in emulsion droplets, Trend Biotech 24(9):395-402 (2006).
Griffiths, A.D. et al., Strategies for selection of antibodies by phage display, Curr Opin Biotechnol, 9:102-8 (1998).
Guatelli, J.C. et al., Isothermal, in vitro amplification of nucleic acids by a multienzyme reaction modeled after retroviral replication, PNAS, 87(5):1874-8 (1990).
Guixe et al., Ligand-Induced Conformational Transitions in *Escherichia coli* Phosphofructokinase 2: Evidence for an Allosteric Site for MgATP2n, Biochem., 37: 13269-12375 (1998).
Gupta, K.C., et al., A general method for the synthesis of 3'-sulfhydryl and phosphate group containing oligonucleotides, Nucl Acids Res 19 (11): 3019-3026 (1991).
Haber et al., Activity and spectroscopic properties of bovine liver catalase in sodium bis(2-ethylhexyl) sulfosuccinate/isooctane reverse micelles, Eur J Biochem 217(2): 567-73 (1993).
Habig and Jakoby, Assays for differentiation of glutathione S-transferases, Methods in Enzymology, 77: 398-405 (1981).
Hadd et al., Microchip Device for Performing Enzyme Assays, Anal. Chem 69(17): 3407-3412 (1997).
Haddad et al., A methodology for solving physiologically based pharmacokinetic models without the use of simulation software, Toxicol Lett. 85(2): 113-26 (1996).
Hagar and Spitzer, The effect of endotoxemia on concanavalin A induced alterations in cytoplasmic free calcium in rat spleen cells as determined with Fluo-3, Cell Calcium 13:123-130 (1992).
Hai et al., Investigation on the release of fluorescent markers from the w/o/w emulsions by fluorescence-activated cell sorter, J Control Release, 96(3): 393-402 (2004).
Haies et al., Morphometric study of rat lung cells. I. Numerical and dimensional characteristics of parenchymal cell population, Am. Rev. Respir. Dis. 123:533-54 (1981).
Hall, Experimental evolution of Ebg enzyme provides clues about the evolution of catalysis and to evolutionary potential, FEMS Microbiol Lett, 174(1):1-8 (1999).
Hall, The EBG system of *E. coli*: origin and evolution of a novel beta-galactosidase for the metabolism of lactose, Genetica 118(2-3):143-56 (2003).
Han et al., Quantum-dot-tagged Microbeads for Multiplexed Optical Coding of Biomolecules, Nat Biotech 19(7): 631-635 (2001).
Handen, J.S., High-throughput screening-challenges for the future, Drug Discov World, 47-50 (2002).
Handique, K. et al., On-Chip Thermopneumatic Pressure for Discrete Drop Pumping, Analytical Chemistry, vol. 73, 2001, pp. 1831-1838.
Hanes et al., Degradation of porous poly(anhydide-co-imide) microspheres and implication for controlled macromolecule delivery, Biomaterials, 19(1-3): 163-172(1998).
Hanes et al., In vitro selection and evolution of functional proteins by using ribosome display, PNAS 94:4937-42 (1997).
Hansen et al., A robust and scalable microfluidic metering method that allows protein crystal growth by free interface diffusion, PNAS 99(26):16531-16536 (2002).
Harada et al., Monoclonal antibody G6K12 specific for membrane-associated differentiation marker of human stratified squamous epithelia and squamous cell carcinoma, J. Oral Pathol. Med 22(4):145-152 (1993).

Harder, K.W. et al., Characterization and kinetic analysis of the intracellular domain of human protein tyrosine phosphatase beta (HPTP beta) using synthetic phosphopeptides, Biochem J 298 (Pt 2): 395-401 (1994).
Harries et al., A Numerical Model for Segmented Flow in a Microreactor, Int J of Heat and Mass Transfer, 46:3313-3322 (2006).
Harris et al., Single-molecule DNA sequencing of a viral genome, Science 320(5872):106-109 (2008).
Harrison et al., Micromachining a miniaturized capillary electrophoresis-based chemical analysis system on a chip, Science 261(5123):895-897 (1993).
Hasina et al., Plasminogen activator inhibitor-2: a molecular biomarker for head and neck cancer progression, Cancer Research 63:555-559 (2003).
Haynes Principles of Digital PCR and Measurement Issue Oct. 15, 2012.
Hayward et al., Dewetting Instability during the Formation of Polymersomes from BloceCopolymer-Stabilized Double Emulsions, Langmuir, 22(10): 4457-4461 (2006).
He et al., Selective encapsulation of single cells and subcellular organelles into picoliter- and femtoliter-volume droplets, Anal Chem 77(6):1539-1544 (2005).
Heim et al., Engineering Green Fluorescent Protein for Improved Brightness, Longer Wavelengths and Fluorescence Response Energy Transfer, Carr. Biol, 6(2): 178-182 (1996).
Hellman et al., Differential tissue-specific protein markers of vaginal carcinoma, Br J Cancer, 100(8): 1303-131 (2009).
Hergenrother et al., Small-Molecule Microarrays: Covalent Attachment and Screening of Alcohol-Containing Small Molecules on Glass Slides, J. Am. Chem. Soc, 122: 7849-7850 (2000).
Hildebrand et al., Liquid-Liquid Solubility of Perfluoromethylcyclohexane with Benzene, Carbon Tetrachloride, Chlorobenzene, Chloroform and Toluene, J. Am. Chem. Soc, 71:22-25 (1949).
Hjelmfelt et al, Pattern-Recognition in Coupled Chemical Kinetic Systems, Science, 260(5106):335-337 (1993).
Ho, S.N. et al., Site-directed mutageneiss by overlap extension using the polymerase chain reaction, Gene, 77(1):51-9 (1989).
Hoang, Physiologically based pharmacokinetic models: mathematical fundamentals and simulation implementations, Toxicol Lett 79(1-3):99-106 (1995).
Hochuli et al., New metal chelate adsorbent selective for proteins and peptides containing neighbouring histidine residues, J Chromatogr 411: 177-84 (1987).
Holmes et al., Reagents for Combinatorial Organic Synthesis: Development of a New O-Nitrobenzyl Photolabile Linder for Solid Phase Synthesis, J. OrgChem., 60: 2318-2319(1995).
Hong, S.B. et al., Stereochemical constraints on the substrate specificity of phosphodiesterase, Biochemistry, 38: 1159-1165 (1999).
Hoogenboom et al., Multi-subunit proteins on the surface of filamentous phage: methodologies for displaying antibody (Fab) heavy and light chains, Nucl Acids Res., 91: 4133-4137 (1991).
Hoogenboom, H.R., Designing and optimizing library selection strategies for generating high-affinity antibodies, Trends Biotechnol, 15:62-70 (1997).
Hopfinger & Lasheras, Explosive Breakup of a Liquid Jet by a Swirling Coaxial Jet, Physics of Fluids 8(7):1696-1700 (1996).
Hopman et al., Rapid synthesis of biotin-, digoxigenin-, trinitrophenyl-, and fluorochrome-labeled tyramides and their application for In situ hybridization using CARD amplification, J of Histochem and Cytochem, 46(6):771-77 (1998).
Horton et al., Engineering hybrid genes without the use of restriction enzymes: gene splicing by overlap extension, Gene 77(1), 61-8 (1989).
Hosokawa, Kazuo et al., Handling of Picoliter Liquid Samples in a Poly(dimethylsiloxane)-Based Microfluidic Device, Analytical Chemistry, vol. 71, No. 20, 1999 pp. 4781-4785.
Hsu et al., Comparison of process parameters for microencapsulation of plasmid DNA in poly(D, L-lactic-co-glycolic acid microspheres, J Drug Target, 7:313-23 (1999).

(56) References Cited

OTHER PUBLICATIONS

Huang L. R. et al., Continuous particle separation through deterministic lateral displacement, Science 304(5673):987-990 (2004).
Huang, Z. et al., A sensitive competitive ELISA for 2,4-dinitrophenol using 3,6-fluorescein diphosphate as a fluorogenic substrate, J Immunol Meth, 149:261 (1992).
Huang, Z.J., Kinetic assay of fluorescein mono-beta-D-galactosidase hydrolysis by beta-galactosidase: a front-face measurement for strongly absorbing fluorogenic substrates, Biochemistry, 30:8530-4 (1991).
Hubert et al. Data Concordance from a Comparison between Filter Binding and Fluorescence Polarization Assay Formats for Identification of RUOCK-II Inhibitors, J biomol Screen 8(4):399-409 (2003).
Huebner, A. et al., Quantitative detection of protein expression in single cells using droplet microfluidics, Chem Com 12:1218-1220 (2007).
Hung et al., Optimization of Droplet Generation by controlling PDMS Surface Hydrophobicity, 2004 ASME International Mechanical Engineering Congres and RD&D Expo, Nov. 13-19, Anaheim, CA (2004).
Hung, et al, Controlled Droplet Fusion in Microfluidic Devices, MicroTAS 2004, Sep. 26-30, Malmo, Sweden (2004).
Hutchison et al., Cell-free cloning using Phi29 polymerase, PNAS 102(48):17332-17336 (2005).
Ibrahim, S.F. et al., High-speed cell sorting: fundamentals and recent advances, Curr Opin Biotchnol, 14(1):5-12 (2003).
Ikeda et al., Bioactivation of tegafur to 5-fluorouracil is catalyzed by cytochrome P-450 2A6 in human liver microsomes in vitro, Clin Cancer Res 6(11):4409-4415 (2000).
Inai et al., Immunohistochemical detection of an enamel protein-related epitope in rat bone at an early stage of osteogenesis, Histochemistry 99(5):335-362 (1993).
International Preliminary Report of Patentability for PCTUS2010061741 dated Sep. 16, 2011(4 pages).
International Preliminary Report on Patentability dated Sep. 20, 2007, for PCT/US2006/007772.
International Search Report and Written Opinion for PCT/US2009/050931 dated Nov 26, 2009 (3 pages).
International Search Report and Written Opinion for PCTUS1154353 dated Apr. 20, 2012 (34 pages).
International Search Report and Written Opinion for PCTUS12024745 dated May 11, 2012 (21 pages).
International Search Report and Written Opinion for PCTUS1224741 dated Jun. 12, 2012 (12 pages).
International Search Report and Written Opinion for PCTUS125499 dated May 29, 2012 (10 pages).
International Search Report and Written Opinion in PCT/EP2010/065188 dated Jan. 12, 2011 (7 pages).
International Search Report and Written Opinion in PCT/US11/24615 dated Jul. 25, 2011 (37 pages).
International Search Report and Written Opinion in PCT/US2004/010903 dated Dec. 20, 2004 (16 pages).
International Search Report and Written Opinion in PCT/US2006/021286 dated Sep. 14, 2007 (16 pages).
International Search Report and Written Opinion in PCT/US2007/002063 dated Nov. 15, 2007 (20 pages).
International Search Report in PCT/US01/18400 dated Jan. 28, 2005 (37 pages).
Ismagilov, Integrated Microfluidic Systems, Angew. Chem. Int. Ed 42:4130-4132 (2003).
Janda, et al, Chemical selection for catalysis in combinatorial antibody libraries, Science, 275:945-948 (1997).
Jang et al., Controllable delivery of non-viral DNA from porous scaffold, J Controlled Release 86(1):157-168 (2003).
Japanese Office Action for JP 2006-509830 dated Jun. 1, 2011 (4 pages).
Jermutus et al., Recent advances in producing and selecting functional proteins by using cell-free translation, Curr Opin Biotechnol 9(5): 534-48 (1998).

Jestin et al., A Method for the Selection of Catalytic Activity Using Phage Display and Proximity Coupling, Agnew. Chem. Int. Ed. Engi. 38(8):1124-1127 (1999).
Jo, et al, Encapsulation of Bovine Serum Albumin in Temperature-Programmed Shell-in-Shell Structures, Macromol. Rapid Comm 24:957-962 (2003).
Joerger et al., Analyte detection with DNA-labeled antibodies and polymerase chain reaction, Clin. Chem. 41(9):1371-7 (1995).
Johannsson et al., Amplification by Second Enzymes, in ELISA and Other Solid Phase Immunoassays, Kemeny et al (ed.), Chapter 4, pp. 85-106 John Wiley (1988).
Johannsson, A., Heterogeneous Enzyme Immunoassays, In Principles and Practice of Immunoassay, pp. 295-325 Stockton Press (1991).
Johnson, T.O. et al., Protein tyrosine phosphatase 1B inhibitors for diabetes, Nature Review Drug Discovery 1, 696-709 (2002).
Jones et al. Glowing jellyfish, luminescence and a molecule called coelenterazine, Trends Biotechnol. 17(12):477-81 (1999).
Jones, L.J. et al., Quenched BODIPY dye-labeled casein substrates for the assay of protease activity by direct fluorescence measurement, Anal Biochem, 251:144 (1997).
Joo et al., Laboratory evolution of peroxide-mediated cytochrome P450 hydroxylaion, Nature 399:670 (1999).
Joos et al., Covalent attachment of hybridizable oligonucleotides to glass supports, Analytical Biochemistry 247:96-101 (1997).
Joyce, G.F., In vitro Evolution of Nucleic Acids, Curr. Opp. Structural Biol, 4: 331-336 (1994).
Kadir and Moore, Haem binding to horse spleen ferritin, Febs Lett, 276: 81-4 (1990).
Kallen, R.G. et al., The mechanism of the condensation of formaldehyde with tetrahydrofolic acid, J. Biol. Chem., 241:5851-63 (1966).
Kambara et al., Optimization of Parameters in a DNA Sequenator Using Fluorescence Detection, Nature Biotechnology 6:816-821 (1988).
Kamensky et al., Spectrophotometer: new instrument for ultrarapid cell analysis, Science 150(3696):630-631 (1965).
Kanouni et al., Preparation of a stable double emulsion (W1/0/W2): role of the interfacial films on the stability of the system, Adv. Collid. Interf. Sci., 99(3): 229-254 (2002).
Katanaev et al., Viral Q beta RNA as a high expression vector for mRNA translation in a cell-free system, Febs Lett, 359:89-92 (1995).
Katsura et al., Indirect micromanipulation of single molecules in water-in-oil emulsion, Electrophoresis, 22:289-93 (2001).
Kawakatsu et al., Regular-sized cell creation in microchannel emulsification by visual microprocessing method, Journal of the American Oil ChemistS Society, 74:317-21 (1997).
Keana J. & Cai, S. X., New reagents for photoaffinity labeling: synthesis and photolysis of functionalized perfluorophenyl azides, J. Org. Chem.55(11):3640-3647 (1990).
Keefe, A.D. et al., Functional proteins from a random-sequence library, Nature, 410: 715-718 (2001).
Keij et al., High-Speed Photodamage Cell Selection Using a Frequency-Doubled Argon Ion Laser, Cytometry, 19(3): 209-216 (1995).
Keij, J.F., et al., High-speed photodamage cell sorting: An evaluation of the ZAPPER prototype, Methods in cell biology, 42: 371-358 (1994).
Kelly et al., Miniaturizing chemistry and biology in microdroplets, Chem Commun 18:1773-1788 (2007).
Kerker, M., Elastic and inelastic light scattering in flow cytometry, Cytometry, 4:1-10 (1983).
Khandjian, UV crosslinking of RNA to nylon membrane enhances hybridization signals, Mol. Bio. Rep. 11: 107-115 (1986).
Kim et al., Comparative study on sustained release of human growth hormone from semi-crystalline poly(L-lactic acid) and amorphous poly(D,L-lactic-co-glycolic acid) microspheres: morphological effect on protein release, Journal of Controlled Release, 98(1):115-125 (2004).
Kim S. et al, Type II quantum dots: CdTe/CdSe (core/shell) and CdSe/ZnTe (core/shell) heterostructures, J. Am Chem Soc. 125:11466-11467 (2003).

(56) References Cited

OTHER PUBLICATIONS

Kircher et al., High-throughput DNA sequencing-concepts and limitations, Bioessays 32(6):524-536 (2010).
Kiss et al., High-throughput quantitative polymerase chain reaction in picoliter droplets, Anal. Chem 80:8975-8981 (2008).
Kitagawa et al., Manipulation of a single cell with microcapillary tubing based on its electrophoretic mobility, Electrophoresis 16:1364-1368 (1995).
Klug and Famulok, All you wanted to know about selex, Molecular Biology Reports, 20:97-107 (1994).
Klug and Schwabe, Protein motifs 5. Zinc fingers, FASEB J 9(8):597-604 (1995).
Klug, A., Gene Regulatory Proteins and Their Interaction with DNA, Ann NY Acad Sci, 758: 143-60 (1995).
Knaak et al., Development of partition coefficients, Vmax and Km values, and allometric relationships, Toxicol Lett. 79(I-3):87-98 (1995).
Knight, James B., Hydrodynamic Focusing on a Silicon Chip: Mixing Nanoliters in Microseconds, Physical Review Lett 80(17):3863-3866 (1998).
Kojima et al. PCR amplification from single DNA molecules on magnetic beads in emulsion: application for high-throughput screening of transcription factor targets. Nucleic Acids Res. 33:e150 (2005).
Kolb et al., Cotranslational folding of proteins, Biochem Cell Biol, 73:1217-20 (1995).
Komatsu et al., Roles of cytochromes P450 1A2, 2A6, and 2C8 in 5-fluorouracil formation rom tegafur, an anticancer prodrug, in human liver microsomes. Drug Met. Disp., 28:1457-1463 (2001).
Kopp et al., Chemical amplification: continuous flow PCR on a chip, Science, 280:1046-48 (1998).
Koster et al., Drop-based microfluidic devices for encapsulation of single cells, Lab on a Chip 8:1110-1115 (2008).
Kowalczykowski et al., Biochemistry of homologous recombination in *Escherichia coli*, Microbiol Rev 58(3):401-65 (1994).
Krafft et al., Emulsions and microemulsions with a fluorocarbon phase, Colloid and Interface Science 8(3):251-258 (2003).
Krafft et al., Synthesis and preliminary data on the biocompatibility and emulsifying properties of perfluoroalkylated phosphoramidates as injectable surfactants, Eur. J. Med. Chem., 26:545-550 (1991).
Kralj et al., Surfactant-enhanced liquid-liquid extraction in microfluidic channels with inline electric-field enhanced coalescence, Lab Chip 5:531-535 (2005).
Kricka and Wilding, Microchip PCR, Anal Bioanal Chem 377(5):820-825 (2003).
Kricka and Wilding, Micromachining: a new direction for clinical analyzers, Pure and Applied Chemistry 68(10):1831-1836 (1996).
Krumdiek, C.L. et al., Solid-phase synthesis of pteroylpolyglutamates, Methods Enzymol, 524-29 (1980).
Kumar, A. et al., Activity and kinetic characteristics of glutathione reductase in vitro in reverse micellar waterpool, Biochem Biophys Acta, 996(1-2):1-6 (1989).
Lage et al., Whole genome analysis of genetic alterations in small DNA samples using hyperbranched strand displacement amplification and array—CGH. Genome Res. 13: 294-307 (2003).
Lamprecht et al., pH-sensitive microsphere delivery increases oral bioavailability of calcitonin, Journal of Controlled Release, 98(1): 1-9(2004).
Lancet, D. et al., Probability model for molecular recognition in biuological receptor repertoirs: significance to the olfactory system, PNAS, 90(8):3715-9 (1993).
Landergren et al., A ligase mediated gene detection technique. Science 241(4869):1077-80 (1988).
Lasheras, et al., Breakup and Atomization of a Round Water Jet by a High Speed Annular Air Jet, J Fluid Mechanics 357:351-379 (1998).
Leary et al., Application of Advanced Cytometric and Molecular Technologies to Minimal Residual Disease Monitoring, Proceedings of SPIE 3913:36-44 (2000).

Lee et al, Investigating the target recognition of DNA cytosine-5 methyltransferase Hhal by library selection using in vitro compartmentalisation (IVC), Nucleic Acids Res 30:4937-4944 (2002).
Lee et al., Circulating flows inside a drop under time-periodic non-uniform electric fields, Phys Fuilds 12(8):1899-1910 (2000).
Lee, et al, Effective Formation of Silicone-in-Fluorocarbon-in-Water Double Emulsions: Studies on Droplet Morphology and Stability, Journal of Dispersion Sci Tech 23(4):491-497(2002).
Lee, et al, Preparation of Silica Paticles Encapsulating Retinol Using O/W/O Multiple Emulsions, Journal of Colloid and Interface Science, 240(1): 83-89 (2001).
Lemof, et al, An AC Magnetohydrodynamic Microfluidic Switch for Micro Total Analysis Systems, Biomedical Microdevices, 5(I):55-60 (2003).
Lesley et al., Use of in vitro protein synthesis from PCR-generated templates to study interaction of *E coli* transcription factors with core RNA polymerase, J Biol Chem 266(4):2632-8 (1991).
Lesley, S.A., Preparation and use of *E. coli* S-30 extracts, Methods Mol Biol, 37:265-78 (1995).
Leung et al., A method for random mutagenesis of a defined DNA segment using a modified polymerase chain reaction. Technique 1:11-15 (1989).
Li and Harrison, Transport, Manipulation, and Reaction of Biological Cells On-Chip Using Electrokinetic Effects, Analytical Chemistry 69(8):1564-1568 (1997).
Li et al., Nanoliter microfluidic hybrid method for simultaneous screening and optimization validated with crystallization of membrane proteins, PNAS 103: 19243-19248 (2006).
Li et al., Single-step procedure for labeling DNA strand breaks with fllourescein-or BODIPY-conjugated deoxynucleotides: detection of apoptosis and bromodeoxyuridine incorporation. Cytometry 20:172-180 (1995).
Liao et al., Isolation of a thermostable enzyme variant by cloning and selection in a thermophile, PNAS 83:576-80 (1986).
Lim et al., Microencapsulated islets as bioartificial endocrine pancreas, Science 210(4472):908-10 (1980).
Link et al, Geometrically Mediated Breakup of Drops in Microfluidic Devices, Phys. Rev. Lett., 92(5): 054503-1 thru 054503-4 (2004).
Link et al., Electric control droplets in microfluidic devices, Angew Chem Int Ed 45:2556-2560 (2006).
Lipinski et al., Experimental and Computational Approaches to Estimate Solubility and Permeability in Drug Discovery and Development Settings ,Adv. Drug Deliv. Rev., 46:3-26 (2001).
Lipkin et al., Biomarkers of increased susceptibility to gastreointestinal cancer: new application to studies of cancer prevention in human subjects, Cancer Research 48:235-245 (1988).
Liu et al., Fabrication and characterization of hydrogel-based microvalves, Mecoelectromech. Syst.11:45-53 (2002).
Liu et al., Passive Mixing in a Three-Dimensional Serpentine MicroChannel, J MEMS 9(2):190-197 (2000).
Lizardi et al., Mutation detection and single-molecule counting using isothermal rolling-circle amplification. Nat Genet 19(3):225-32 (1998).
Loakes and Brown, 5-Nitroindole as a universal base analogue. Nucleic Acids Res 22: 4039-4043 (1994).
Loakes et al., Stability and structure of DNA oligonucleotides containing non-specific base analogues. J. Mol. Biol 270:426-435 (1997).
Loeker et al., Colloids and Surfaces A: Physicochem. Eng. Aspects 214: 143-150, 2003).
Lopez-Herrera, et al, Coaxial jets generated from electrified Taylor cones. Scaling laws., Aerosol Science, 34 :535-552 (2003).
Lopez-Herrera, et al, One-Dimensional Simulation of the Breakup of Capillary Jets of Conducting Liquids Application to E.H.D. Spraying, Aerosol. Set, 30 (7): 895-912 (1999).
Lopez-Herrera, et al, {The electrospraying of viscous and non-viscous semi-insulating liquids. Scalilng laws,{ Bulletin of the American Physical Society, vol. 40, No. 12, pp. 2041 (1995).
Lorenceau et al, Generation of Polymerosomes from Double-Emulsions, Langmuir, 21(20): 9183-9186 (2005).

(56) References Cited

OTHER PUBLICATIONS

Lorenz et al, Isolation and expression of a cDNA encoding Renilla reniformis luciferase, PNAS 88(10):4438-42 (1991).
Loscertales, et al, Micro/Nano Encapsulation via Electrified Coaxial Liquid Jets, Science, 295(5560): 1695-1698 (2002).
Low N.M. et al., Mimicking somatic hypermutaion: affinity maturation of antibodies displayed on bacteriophage using a bacterila mutator strain. J Mol Biol 260(3), 359-68 (1996).
Lowe, K.C., Perfluorochemical respiratory gas carriers: benefits to cell culture systems, J Fluorine Chem 118:19-26 (2002).
Lowman et al., Selecting high affinity binding proteins by monovalent phage display, Biochemistry 30(45):10832-8 (1991).
Lu et al., Robust fluorescein-doped silica nanoparticles via dense-liquid treatment, Colloids and Surfaces a Physicachemical and Engineering Aspects, 303(3):207-210 (2007).
Luisi et al, Activity and Conformation of Enzymes in Reverse Micellar Solutions, Meth. Enzymol 136:188-216 (1987).
Lund et al., Assesment of methods for covalent binding of nucleic acids to magnetic beads, Dynabeads, and the characteristics of the bound nucleic acids in hybridization reactions, Nucleic Acids Research, Oxford University Press, 16(22) (1998).
Lunderberg et al., Solid-phase technology: magnetic beads to improve nucleic acid detection and analysis, Biotechnology Annual Review, 1:373-401 (1995).
Lundstrom, et al, Breakthrough in cancer therapy: Encapsulation of drugs and viruses, www.currentdrugdiscovery.com, Nov. 19-23, 2002.
Lyne, P.D., Structure-Based Virtual Screening: An Overview, Drug Discov. Today, 7(20):1047-1055 (2002).
Ma, C. et al., In vitro protein engineering using synthetic tRNA(Ala) with different anticodons, Biochemistry 32(31):7939-45 (1993).
Mackenzie et al., The application of flow microfluorimetry to biomedical research and diagnosis: a review, Dev Biol Stand 64:181-193 (1986).
Mackenzie, IABS Symposium on Reduction of Animal Usage in the Development and Control of Biological Products, London, UK, 1985.
Maclean, D. et al., Glossary of terms used in combinatorial chemistry, Pure Appl. Chem. 71(12):2349-2365 (1999).
Magdassi et al., Multiple Emulsions: HLB Shift Caused by Emulsifier Migration to External Interface, J. Colloid Interface Sci 97:374-379 (1984).
Mahajan et al., Bcl-2 and Bax Interactions in Mitochondria Probed with Green Florescent Protein and Fluorescence Resonance Energy Transfer, Nat. Biotechnol. 16(6): 547-552 (1998).
Manley et al., In vitro transcription: whole cell extract, Methods Enzymol, 101:568-82 (1983).
Manz et al., Micromachining of monocrystalline silicon and glass for chemical analysis systems a look into next century's technology or just a fashionable craze, Trends in Analytical Chemistry 10(5):144-149 (1991).
Mao et al., Kinetic behaviour of alpha-chymotrypsin in reverse micelles: a stopped-flow study, Eur J Biochem 208(1):165-70 (1992).
Mao, Q. et al., Substrate effects on the enzymatic activity of alphachymotrypsin in reverse micelles, Biochem Biophys Res Commun, 178(3):1105-12 (1991).
Mardis, E.R., The impact of next-generation sequencing technology on genetics, Trends Genet 24:133-141 (2008).
Margulies, M et al., Genome sequencing in microfabricated high-density picolitre reactors, Nature 437(7057):376-380 (2005).
Marques et al., Porous Flow within Concentric Cylinders, Bull Am Phys Soc Div Fluid Dyn 41:1768 (1996).
Mason, T.J. and Bibette, J. Shear Rupturing of Droplets in Complex Fluids, Langmuir, 13(17):4600-4613 (1997).
Mastrobattista et al., High-throughput screening of enzyme libraries: in vitro evolution of a beta-galactosidase by fluorescence-activated sorting of double emulsions, Chem. Biol. 12(12): 1291-1300 (2005).
Masui et ai., Probing of DNA-Binding Sites of Escherichia coli RecA Protein Utilizing 1-anilinonaphthalene-8-Sulfonic Acid, Biochem 37(35):12133-12143 (1998).
Matayoshi, E.D. et al., Novel fluorogenic substrates for assaying retroviral proteases by resonance energy transfer, Science 247:954 (1990).
Mattheakis et al., An in vitro polysome display system for identifying ligands from very large peptide libraries, PNAS 91:9022-6 (1994).
Mayr, L.M., and Fuerst, P., The Future of High-Throughput Screening, JBiomol Screen 13:443-448 (2008).
Mazutis et al., Droplet-Based Microfluidic Systems for High-Throughput Single DNA Molecule Isothermal Amplification and Analysis, Anal Chem 81(12):4813-4821 (2009).
Mazutis et al., Multi-step microfluidic droplet processing: kinetic analysis of an in vitro translated enzyme, Lab Chip 9:2902-2908 (2009).
McCafferty et al., Phage antibodies: filamentous phage displaying antibody variable domains,Nature, 348: 552-4 (1990).
McDonald and Whitesides, Poly(dimethylsiloxane) as a material for fabricating microfluidic devices, Account Chem. Res. 35:491-499 (2002).
McDonald et al. Fabrication of microfluidic systems in poly(dimethylsiloxane), Electrophoresis 21(1):27-40 (2000).
Melton et al., Efficient in vitro synthesis of biologically active RNA and RNA hybridization probes from plasmids containing a bacteriophage SP6 promoter, Nucl. Acids Res. 12(18):7035-7056 (1984).
Mendel, D. et al., Site-Directed Mutagenesis with an Expanded Genetic Code, Annu Rev Biophys Biomol Struct, 24:435-62 (1995).
Menger and Yamada, Enzyme catalysis in water pools, J. Am. Chem. Soc., 101:6731-4 (1979).
Meylan and Howard, Atom/fragment contribution method for estimating octanol-water partition coefficients, J Pharm Sci. 84(1):83-92 (1995).
Miele et al., Autocatalytic replication of a recombinant RNA, J Mol Biol, 171:281-95 (1983).
Minshuil, J. and Stemmer, W.P., Protein evolution by molecular breeding, Curr Opin Chem Biol 3(3): 284-90 (1999).
Miroux and Walker, Over-production of proteins in Escherichia coli: mutant hosts that allow synthesis of some membrane proteins and globular proteins at high levels, J of Mol Biol 260(3):289-98 (1996).
Miyawaki et at., Fluorescent Indicators for Ca2+ Based on Green Fluorescent Proteins and Calmodulin, Nature, 388: 882-887 (1997).
Mize et al., Dual-enzyme cascade—an amplified method for the detection of alkaline phosphatase, Anal Biochem 179(2): 229-35 (1989).
Mock et al., A fluorometric assay for the biotin-avidin interaction based on displacement of the fluorescent probe 2-anilinonaphthalene-6-sulfonic acid, Anal Biochem, 151:178-81 (1985).
Moldavan, A., Photo-electric technique for the counting of microscopical cells, Science 80:188-189 (1934).
Montigiani, S. et al., Alanine substitutions in calmodulin-binding peptides result in unexpected affinity enhancement, J Mol Biol, 258:6-13 (1996).
Moore, M.J., Exploration by lamp light, Nature, 374:766-7 (1995).
Moudrianakis and Beer, Base sequence determination in nucelic acids with the electron microscope 3. Chemistry and microscopy of guanine-labeled DNA, PNAS 53:564-71 (1965).
Mueth et al., Origin of stratification in creaming emulsions, Physical Review Letters 77(3):578-581 (1996).
Mulbry, W.W. et al., Parathion hydrolase specified by the Flavobacterium opd gene: relationshio between the gene and protein. J Bacteriol, 171: 6740-6746 (1989).
Mulder et al., Characterization of two human monoclonal antibodies reactive with HLA-B12 and HLA-B60, respectively, raised by in vitro secondary immunization of peripheral blood lymphocytes, Hum. Immunol 36(3):186-192 (1993).
Nakano et al., High speed polymerase chain reaction in constant flow, Biosci Biotech and Biochem, 58:349-52 (1994).
Nakano et al., Single-molecule PCR using water-in-oil emulsion, J Biotech, 102:117-24 (2003).

(56) References Cited

OTHER PUBLICATIONS

Nakano et al., Single-molecule reverse transcription polymerase chain reaction using water-in-oil emulsion, J Biosci Bioeng 99:293-295 (2005).
Nametkin, S.N. et al., Cell-free translation in reversed micelles, FEB Letters, 309(3):330-32.
Narang et al, Improved phosphotriester method for the synthesis of gene fragments, Methods Enzymol, 68:90-98 (1979).
Nelson, P. S., et al., Bifunctional oligonucleotide probes synthesized using a novel CPG support are able to detect single base pair mutations, Nucl Acids Res 17(18): 7187-7194 (1989).
Nemoto et al., In vitro virus: bonding of mRNA bearing puromycin at the 3 terminal end to the C-terminal end of its encoded protein on the ribosome in vitro, Federation of European Biochemical Societies, 414:405-8 (1997).
Ness, J.E. et al., Molecular Breeding: the natural approach to protein design. Adv Protein Chem, 55: 261-292 (2000).
Ng et al., Protein crystallization by capillary counter-diffusion for applied crystallographic structure determination, J. Struct. Biol. 2003, v142, pp. 218-231.
Ng, B.L. et al., Factors affecting flow karyotype resolution, Cytometry, Part A 69A: 1028-1036 (2006).
Nguyen et al., Optical detection for droplet size control in microfluidic droplet-based analysis systems, Sensors and Actuators B 117(2):431-436 (2006).
Nihant et al., Polylactide Microparticles Prepared by Double Emulsion/Evaporation Technique. I. Effect of Primary Emulsion Stability, Pharmaceutical Research, 11(10):1479-1484 (1994).
Nisisako et al., Controlled formulation of monodisperse double emulsions in a multiple-phase microluidic system, Sot Matter, 1:23-27 (2005).
Nisisako et al., Formation of droplets using branch channels in a microfluidic circuit, Proceedings of the SICE Annual Conference. International Session Papers 1262-1264 (2002).
Nisisako et al., Microstructured Devices for Preparing Controlled Multiple Emulsions. Chem. Eng. Technol 31(8):1091-1098 (2008).
Nisisako, Takasi et al., Droplet Formation in a MicroChannel NetWO rk, Lab on a Chip, vol. 2, 2002, pp. 24-26.
Nissim, A. et al., Antibody fragments from a single pot phage display library as immunochemical reagents, Embo J, 13:692-8 (1994).
Nof and Shea, Drug-releasing scaffolds fabricated from drug-loaded microspheres, J. Biomed Mater Res 59:349-356 (2002).
Norman, A., Flow Cytometry, Med. Phys., 7(6):609-615 (1980).
Oberholzer et al., Enzymatic RNA replication in self-reproducing vesicles: an approach to a minimal cell, Biochem Biophys Res Commun 207(1):250-7 (1995).
Oberholzer et al., Polymerase chain reaction in liposomes, Chem. Biol. 2(10):677-82 (1995).
Obukowicz, M.G. et al., Secretion and export of IGF-1 in *Escerichia coli* strain JM101, Mol Gen Genet, 215:19-25 (1988).
Office Action for U.S. Appl. No. 11/246,911 dated Feb. 8, 2011.
Office Action for U.S. Appl. No. 11/360,845 dated Apr. 26, 2011.
Office Action for U.S. Appl. No. 11/360,845 dated Aug. 4, 2010.
Office Action for U.S. Appl. No. 11/698,298, dated Jun. 29, 2011.
Ogura, Y., Catalase activity at high concentrations of hydrogen peroxide, Archs Biochem Biophys, 57: 288-300 (1955).
Oh et al., Distribution of Macropores in Silica Particles Prepared by Using Multiple Emulsions, Journal of Colloid and Interface Science, 254(1): 79-86 (2002).
Okushima et al. Controlled production of monodisperse double emulsions by two-step droplet breakup in microfluidic devices, Langmuir 20(23): 9905-8 (2004).
Olsen et ai., Function-based isolation of novel enzymes from a large library, Nat Bioteoltnol 13(10):1071-4 (2000).
Omburo, G.A. et al., Characterization of the zinc binding site of bacterial phosphotriesterase, J of Biological Chem, 267:13278-83 (1992).
Oroskar et al., Detection of immobilized amplicons by ELISA-like techniques, Clin. Chem. 42:1547-1555 (1996).

Ostermeier, M. et al., A combinatorial approach to hybrid enzymes independent of DNA homology, Nat Biotechnol, 17(12):1205-9 (1999).
Ouelette, A new wave of microfluidic devices, Indust Physicist pp. 14-17 (2003).
Pabit et al., Laminar-Flow Fluid Mixer for Fast Fluorescence Kinetics Studies, Biophys J 83:2872-2878 (2002).
Paddison et al., Stable suppression of gene expression by RNAi in mammalian cells, PNAS 99(3):1443-1448 (2002).
Pannacci et al., Equilibrium and Nonequilibrium States in Microluidic Double Emulsions Physical Review Leters, 101(16):164502 (2008).
Park et al., Cylindrical compact thermal-cycling device for continuoflow polymeras chain reaction, Anal Chem, ACS, 75:6029-33 (2003).
Park et al., Model of Formation of Monodispersed Colloids, J. Phys. Chem. B 105:11630-11635 (2001).
Parker et al., Development of high throughput screening assays using fluorescence polarization: nuclear receptor-ligand-binding and kinase/phosphatase assays, J Biomol Screen, 5(2): 77-88 (2000).
Parmley et al., Antibody-selectable filamentous fd phage vectors: affinity purification of target genes. Gene 73(2):305-18 (1988).
Pedersen et al., A method for directed evolution and functional cloning of enzymes, PNAS 95(18):10523-8 (1998).
Pelham and Jackson, An efficient mRNA-dependent translation system from reticulocyte lysates, Eur J Biochem 67:247-56 (1976).
Pelletier et al., An in vivo library-verslibrary selection of optimized protein-protein interactions, Nature Biotechnology, 17:683-90 (1999).
Peng et al., Controlled Production of Emulsions Using a Crossflow Membrane, Particle & Particle Systems Characterization 15:21-25 (1998).
Perelson et al., Theorectical studies of clonal selection: minimal antibody repertoire size and relaibility of self-non-self discrimination. J Theor Biol 81(4):645-70 (1979).
Perez-Gilabert et al., Application of active-phase plot to the kinetic analysis of lipoxygenase in reverse micelles, Biochemistry J. 288:1011-1015 (1992).
Perrin, J., Polarisation de la lumiere de fluorescence vie moyenne des molecules dans letat excite, J. Phys. Rad. 1:390-401 (1926).
Petrounia, I.P. et al., Designed evolution of enzymatic properties, Curr Opin Biotechnol, 11:325-330 (2000).
Piemi et al., Transdermal delivery of glucose through hairless rat skin in vitro: effect of multiple and simple emulsions, Int J Pharm, 171:207-215 (1998).
Pirrung et al., A General Method for the Spatially Defined Immobilization of Biomolecules on Glass Surfaces Using 'Caged' Biotin, Bioconjug Chem 7: 317-321 (1996).
Ploem, in Fluorescent and Luminescent Probes for Biological Activity Mason, T. G. Ed., Academic Press, Landon, pp. 1-11, 1993.
Pluckthun, A. et al., In vitro selection and evolution of proteins, Adv Protein Chem, 55: 367-403 (2000).
Pollack et al., Electrowetting-based actuation of droplets for integrated microfluidics, Lab Chip 2:96-101 (2002).
Pollack et al., Selective chemical catalysis by an antibody, Science 234(4783):1570-3 (1986).
Pons et al, Synthesis of Near-Infrared-Emitting, Water-Soluble CdTeSe/CdZnS Core/Shell Quantum Dots, Chemistry of Materials 21(8):1418-1424 (2009).
Posner et al., Engineering specificity for folate into dihydrofolate reductase from *Escherichia coli*, Biochemistry, 35: 1653-63 (1996).
Poulin and Theil, "A priori" prediction of tissue: plasma partition coefficients of drugs to facilitate the use of physiologically-based pharmokinetic models in drug discovery, J Pharm Sci 89(1):16-35 (2000).
Priest, et al. Generation of Monodisperse Gel Emulsions in a Microfluidic Device, Applied Physics Letters, 88:024106 (2006).
Qi et al., Acid Beta-Glucosidase: Intrinsic Fluorescence and Conformational Changes Induced by Phospholipids and Saposin C, Biochem., 37(33): 11544-11554 (1998).

(56) References Cited

OTHER PUBLICATIONS

Raghuraman et al., Emulston Liquid Membranes for Wastewater Treatment: Equillibrium Models for Some Typical Metal-Extractant Systems,Environ. Sci. Technol 28:1090-1098 (1994).
Ralhan, Discovery and Verification of Head-and-neck Cancer Biomarkers by Differential Protein Expression Analysis Using iTRAQ Labeling, Multidimensional Liquid Chromatography, and Tandem Mass Spectrometry, Mol Cell Proteomics 7(6):1162-1173 (2008).
Ramsey, J.M., The burgeoning power of the shrinking laboratory, Nat Biotechnol 17(11):1061-2 (1999).
Ramstrom and Lehn, Drug discovery by dynamic combinatorial libraries, Nat Rev Drug Discov 1:26-36 (2002).
Raushel, F.M. et al., Phosphotriesterase: an enzyme in search of its natural substrate, Adv Enzymol Relat Areas Mol Biol, 74: 51-93 (2000).
Rech et al., Introduction of a yeast artificial chromosome vector into *Sarrachomyeces cervesia* by electroporation, Nucleic Acids Res 18:1313 (1990).
Reyes et al., Micro Total Analysis Systems. 1. Introduction, Theory and Technology, Anal Chem 74(12):2623-2636 (2002).
Riess, J.S., Fluorous micro- and nanophases with a biomedical perspective, Tetrahedron 58(20):4113-4131 (2002).
Roach et al., Controlling nonspecific protein adsorption in a plug-based microfluidic system by controlling inteifacial chemistry using fluorophase surfactants, Anal. Chem. 77:785-796 (2005).
Roberts & Ja, In vitro selection of nucleic acids and proteins: What are we learning?, Curr Opin Struct Biol 9(4): 521-9 (1999).
Roberts et al., Simian virus 40 DNA directs synthesis of authentic viral polypeptides in a linked transcription-translation cell-free system 72(5):1922-1926 (1975).
Roberts, et al., RNA-peptide fusion for the in vitro selection of peptides and proteins, PNAS 94:12297-302 (1997).
Roberts, J.W.,Termination factor for RNA synthesis, Nature, 224: 1168-74 (1969).
Roberts, R.W. Totally in vitro protein selection using mRNA-protein fusions and ribosome display. Curr Opin Chem Biol 3(3), 268-73 (1999).
Rodriguez-Antona et al., Quantitative RT-PCR measurement of human cytochrome P-450s: application to drug induction studies. Arch. Biochem. Biophys., 376:109-116 (2000).
Rolland et al., Fluorescence Polarization Assay by Flow Cytometry, J. Immunol. Meth., 76(1): 1-10 (1985).
Rosenberg et al.,Termination of transcription in bacteriophage lambda, J Biol Chem, 250: 4755-64 (1975).
Rosenberry, T.L., Acetylcholinesterase, Adv Enzymol Relat Areas Mol Biol, 43: 103-218 (1975).
Rotman, Measurement of activities of single molecules of beta-galactosidase, PNAS, 47:1981-91 (1961).
Russon et al., Single-nucleotide polymorphism analysis by allele-specific extension of fluorescently labeled nucleotides in a microfluidic flow-through device, Electrophoresis, 24:158-61 (2003).
Sadtler et al., Achieving stable, reverse water-in-fluorocarbon emulsions. Angew Chem Int Ed 35:1976-1978 (1996).
Saiki, R.K, et al, Primer directed enzymatic amplification of DNA with a thermostable DNA polymerase. Science 239(4839):487-91 (1988).
Sakamoto, Rapid and simple quantification of bacterial cells by using a microfluidic device, Appl Env Microb. 71:2 (2005).
Sanchez et al., Breakup of Charged Capillary Jets, Bulletin of the American Physical Society Division of Fluid Dynamics 41:1768-1768 (1996).
Sano, T. et al., Immuno-PCR-Very sensitive antigen-detection by means of sepcific antibody-DNA conjugates. Science 258(5079), 120-122 (1992).
SantaLucia, A unified view of polymer, dumbbell, and oligonucleotide DNA nearest-neighbor thermodynamics, PNAS 95(4):1460-5 (1998).
Santra et al., Fluorescence lifetime measurements to determine the core-shell nanostructure of FITC-doped silica nanoparticles: An optical approach to evaluate nanoparticle photostability, J Luminescence 117(1):75-82 (2006).
Schatz et al., Screening of peptide libraries linked to lac repressor, Methods Enzymol 267: 171-91 (1996).
Schneegass et al., Miniaturized flow-through PCR with different template types in a silicone chip thermocycler, Lab on a Chip, Royal Soc of Chem, 1:42-9 (2001).
Schubert et al., Designer Capsules, Nat Med 8:1362 (2002).
Schweitzer et al., Immunoassays with rolling circle DNA amplification: A versatile platform for ultrasensitive antigen detection, PNAS 97(18), 10113-10119 (2000).
Schweitzer, B. et al., Combining nucleic acid amplification and detection. Curr Opin Biotechnol 12(1):21-7 (2001).
Scott, R.L., The Solubility of Fluorocarbons, J. Am. Chem. Soc, 70: 4090-4093 (1948).
Seethala and Menzel, Homogeneous, Fluorescence Polarization Assay for Src-Family Tyrosine Kinases, Anal Biochem 253(2):210-218 (1997).
Seiler et al., Planar glass chips for capillary electrophoresis: repetitive sample injection, quantitation, and separation efficiency, Anal Chem 65(10):1481-1488 (1993).
Selwyn M. J., A simple test for inactivation of an enzyme during assay, Biochim Biophys Acta 105:193-195 (1965).
Seo et al., Microfluidic consecutive flow-focusing droplet generators, Soft Matter, 3:986-992 (2007).
Seong and Crooks, Efficient Mixing and Reactions Within Microfluidic Channels Using Microbead-Supported Catalysts, J Am Chem Soc 124(45):13360-1 (2002).
Seong et al., Fabrication of Microchambers Defined by Photopolymerized Hydrogels and Weirs Within Microfluidic Systems: Application to DNA Hybridization, Analytical Chem 74(14):3372-3377 (2002).
Sepp et al., Microbead display by in vitro compartmentalisation: selection for binding using flow cytometry, FEBS Letters 532:455-58 (2002).
Serpersu et al., Reversible and irreversible modification of erythrocyte membranse permeability by electric field, Biochim Biophys Acta 812(3):779-785 (1985).
Shapiro, H.M., Multistation multiparameter flow cytometry: a critical review and rationale, Cytometry 3: 227-243 (1983).
Shestopalov et al., Multi-Step Synthesis of Nanoparticles Performed on Millisecond Time Scale in a Microfluidic Droplet-Based System, The Royal Society of Chemistry 4:316-321, 2004.
Shtern V, and Hussain F., Hysteresis in swirling jets, J. Fluid Mech. 309:1-44 (1996).
Sia &Whitesides, Micro?uidic devices fabricated in poly(dimethylsiloxane) for biological studies, Electrophoresis 24(21):3563-3576 (2003).
Sidhu, S.S., Phage display in pharmaceutical biotechnology, Curr Opin Biotech 11:610-616 (2000).
Siemering et al., Mutations that suppress the thermosensitivity of green fluorescent protein, Current Biology 6:1653-1663 (1996).
Silva-Cunha et al., W/O/W multiple emulsions of insulin containing a protease inhibitor and an absorption enhancer: biological activity after oral administration to normal and diabetic rats, Int J Pharm 169:33-44 (1998).
Sims et al., Immunopolymerase chain reaction using real-time polymerase chain reaction for detection, Anal. Biochem. 281(2):230-2 (2000).
Slappendel et al., Normal cations and abnormal membrane lipids in the red blood cells of dogs with familial stomatocytosis hypertrophic gastritis, Blood 84:904-909 (1994).
Slob et al., Structural identifiability of PBPK models: practical consequences for modeling strategies and study designs, Crit Rev Toxicol. 27(3):261-72 (1997).
Smith et al., Direct mechanical measurements of the elasticity of single DNA molecules by using magnetic beads, Science 258(5085):1122-1126 (1992).
Smith et al., Fluorescence detection in automated DNA sequence analysis, Nature 321 :674-679 (1986).

(56) References Cited

OTHER PUBLICATIONS

Smith et al., Phage display, Chemical Reviews 97(2), 391-410 (1997).
Smith et al., The synthesis of oligonucleotides containing an aliphatic amino group at the 5' terminus: synthesis of fluorescent DNA primers for use in DNA sequence analysis, Nucl. Acid Res. 13:2399-2412 (1985).
Smith G.P., Filamentous fusion phage: novel expression vectors that display cloned antigens on the virion surface, Science 228(4705): 1315-7(1985).
Smyth et al., Markers of apoptosis: methods for elucidating the mechanism of apoptotic cell death from the nervous system, Biotechniques 32:648-665 (2000).
Sohn, et al, Capacitance cytometry: Measuring biological cells one by one, PNAS 97(20):10687-10690 (2000).
Somasundaram and Ramalingam, Gain studies of Rhodamine 6G dye doped polymer laser, J Photochem Photobiol 125(1-3):93-98 (1999).
Song et al., A microfluidic system for controlling reaction networks in time, Angew. Chem. Int. Ed. 42(7):768-772 (2003).
Song et al., Experimental Test of Scaling of Mixing by Chaotic Advection in Droplets Moving Through Microfluidic Channels, App Phy Lett 83(22):4664-4666 (2003).
Song, H. and Ismagilov, R.F., Millisecond kinetics on a microluidic chip using nanoliters of reagents, J Am Chem Soc. 125: 14613-14619 (2003).
Soni and Meller, Progress toward ultrafast DNA sequencing using solid-state nanopores, Clin Chem 53:1996-2001 (2007).
Soumillion et al., Novel concepts for the selection of catalytic activity. Curr Opin Biotechnol 12:387-394 (2001).
Soumillion et al., Selection of B-lactomase on filamentous bacteriophage by catalytic activity, J Mol Biol, 237:415-22 (1994).
Sproat et al., The synthesis of protected 5'-mercapto-2',5'-dideoxyribonucleoside-3'-0-phosphorainidites, uses of 5'-mercapto-oligodeoxyribonucleotides, Nucleic Acids Res 15:4837-4848 (1987).
Stauber, et a., Rapid generation of monoclonal antibody-secreting hybridomas against African horse sickness virus by in vitro immunization and the fusion/cloning technique, J. Immunol. Meth 161(2):157-168 (1993).
Stemmer, W.P., DNA shuffling by random fragmentation and reassembly: in vitro recombination for molecular evolution. PNAS 91(22):10747-51(1994).
Stemmer, W.P., Rapid evolution of a protein in vitro by DNA shuffling, Nature 370(6488):389-91 (1994).
Stober et al., Controlled growth of monodisperse silica spheres in the micron size range, J Colloid and Interface Sci 26(1):62-69 (1968).
Stofko, H.R. et al., A single step purification for recombinant proteins. Characterization of microtube associated protein (MAP2) fragment which associates with the type II cAMP-dependent protein kinase, Febs Lett 302: 274-278 (1992).
Stone et al., Engineering flows in small devices: Microfluidics toward a lab-on-a-chip, Ann. Rev. Fluid Mech. 36:381-441 (2004).
Strizhkov et al., PCR amplification on a microarray of gel-immobilized oligonucleotides: Detection of bacterial toxin- and drug-resistant genes and their mutations, BioTechniques 29(4):844-857 (2000).
Stroock et al., Chaotic mixer for microchannels, Science 295(5555):647-651 (2002).
Studer et al., Fluorous Synthesis: A FluoroPhase Strategy for Improving Separation Efficiency in Organic Synthesis, Science 275: 823-826 (1997).
Sugiura et al., Effect of Channel Structure on MicroChannel Emuisification, Langmuir 18:5708-5712 (2002).
Sugiura et al., Interfacial tension driven monodispersed droplet formation from mtcrofabricated channel array Langmuir, 17: 5562-5566 (2001).
Sundberg et al., Spatially-Addressable Immobilisation of Macromolecules on Solid Supports, J. Am. Chem. Soc, 117:12050-12057 (1995).
Sung et al. Chip-based microfluidic devices coupled with electrospray ionization-mass spectrometry, Electrophoresis 26:1783-1791 (2005).
Suzuki et al., Random mutagenesis of thermus aquaticus DNA polmerase I: concordance of immutable sites in vivo with the crystal structure, PNAS USA, 93:96701-9675 (1996).
Tabatabai and Faghri, A New Two-Phase Flow Map and Transition Boundary Accounting for Surface Tension Effects in Horizontal Miniature and Micro Tubes, J Heat Transfer 123:958-968 (2001).
Tabatabai et al, Economic feasability study of polyelectrolyte-enhanced ultrafiltration (PEUF) for water softening, J Membrane Science 100(3):193-207 (1995).
Tabatabai et al., Reducing Surfactant Adsorption on Carbonate Reservoirs, SPE Resenroir Engineering 8(2):117-122 (1993).
Tabatabai, Water Softening Using polyelectrolyte-enhanced ultrafiltration, Separation Science Technology 30(2):211-224 (1995).
Takayama et al., Patterning Cells and Their Environments Using Multiple Laminar Fluid Flows in Capillary NetWO rks, PNAS 96:5545-5548 (1999).
Takeuchi et al., An Axisymmetric Flow-Focusing Microfluidic Device, Adv. Mater 17(8):1067-1072 (2005).
Taly et al., Droplets as Microreactors for High-Throughput Biology, Chembiochem 8(3):263-272 (2007).
Tan et al., Controlled Fission of Droplet Emulsions in Bifurcating Microfluidic Channels, Transducers Boston (2003).
Tan et al., Design of microluidic channel geometries for the control of droplet volume, chemical concentration, and sorting, Lab Chip, 4(4): 292-298 (2004).
Tan et al., Monodispersed micro?uidic droplet generation by shear focusing microfluidic device, Sensors and Actuators 114:350-356 (2006).
Tan, Y.C., Microfluidic Liposome Generation from Monodisperse Droplet Emulsion-Towards the Realization of Artificial Cells, Summer Bioengineering Conference, Florida (2003).
Tan, Y.C., Monodisperse Droplet Emulsions in Co-Flow Microfluidic Channels, Micro TAS, Lake Tahoe (2003).
Tanaka et al., Ethanol Production from Starch by a Coimmobilized Mixed Culture System of Aspergillus awamori and Zymomonas mobilis, Biotechnol Bioeng XXVII:1761-1768 (1986).
Tang et al., A multi-color fast-switching microfluidic droplet dye laser, Lab Chip 9:2767-2771 (2009).
Taniguchi et al., Chemical Reactions in Microdroplets by Electrostatic Manipulation of Droplets in Liquid Media, Lab on a Chip 2:19-23 (2002).
Tawfik et al., catELISA: a facile general route to catalytic antibodies, PNAS 90(2):373-7 (1993).
Tawfik et al., Efficient and selective p-nitrophenyl-ester=hydrolyzing antibodies elicited by a p-nitrobenzyl phosphonate hapten, Eur J Biochem, 244:619-26 (1997).
Tawfik et al., Man-made cell-like compartments for molecular evolution, Nature Biotechnology, 7(16):652-56 (1998).
Tawfik, D.S. et al., 1,8-diabycyclo[5.4.0]undecane mediated transesterification of p-nitrophenyl phosphonates—a novel route to phosphono esters, Synthesis-Stuttgart, 10: 968-972 (1993).
Taylor et al., Characterization of chemisorbed monolayers by surface potential measurments, J. Phys. D. Appl. Phys. 24:1443 (1991).
Taylor, The formation of emulsions in definable field of flow, Proc R Soc London A 146(858):501-523 (1934).
Tchagang et al., Early detection of ovarian cancer using group biomarkers, Mol Cancer Ther 7:27-37 (2008).
Tencza et al., Development of a Fluorescence Polarization-Based Diagnostic Assay for Equine Infectious Anemia Virus, J Clinical Microbiol 38(5):1854-185 (2000).
Terray et al., Microfluidic Control Using Colloidal Devices,Science, 296(5574):1841-1844 (2002).
Terray, et al, Fabrication of linear colloidal structures for microfluidic applications, Applied Phys Lett 81(9):1555-1557 (2002).

(56) References Cited

OTHER PUBLICATIONS

Tewhey et al., Microdroplet-based PCR amplification for large scale targeted sequencing, Nat Biotechnol 27(11):1025-1031 (2009).
Theberge et al., Microdroplets in Microfluidics: An Evolving Platform for Discoveries in Chemistry and Biology, Angew. Chem. Int. Ed 49(34):5846-5868 (2010).
Thompson, L.F., Introduction to Lithography, ACS Symposium Series 219:1-13, (1983).
Thorsen et al., Dynamic pattern formation in a vesicle-generating microfluidic device, Phys Rev Lett 86(18):4163-4166 (2001).
Thorsen et al., Microfluidic Large-Scale Integration, Science 298:580-584 (2002).
Tice et al., Effects of viscosity on droplet formation and mixing in microfluidic channels, Analytica Chimica Acta 507:73-77 (2004).
Tice et al., Formation of droplets and mixing in multiphase microfluidics at low values of the reynolds and the capillary numbers, Langmuir 19:9127-9133 (2003).
Titomanlio et al., Capillary experiments of flow induced crystallization of HOPE, AlChe Journal, 1990, v36, No. 1, pp. 13-18.
Tleugabulova et al., Evaluating formation and growth mechanisms of silica particles using fluorescence anisotropy decay analysis, Langmuir 20(14):5924-5932 (2004).
Tokatlidis et al., Nascent chains: folding and chaperone intraction during elongation on ribosomes, Philos Trans R Soc Lond B Biol Sci, 348:89-95 (1995).
Tokeshi et al., ContinuoFlow Chemical Processing on a Microchip by Combining Microunit Operations and a Multiphase Flow NetWO rk, Anal Chem 74(7):1565-1571 (2002).
Tokumitsu, H. et al., Preparation of gadopentetic acid-loaded chitosan microparticles for gadolinium neutron-capture therapy of cancer by a novel emulsion-droplet coalescence technique, Chem and Pharm Bull 47(6):838-842 (1999).
Tramontano, A., Catalytic antibodies, Science 234(4783):1566-70 (1986).
Trindade, T., Nanocrystalline semiconductors: synthesis, properties, and perspectives, Chem. Mat. 13:3843-3858 (2001).
Tripet, B. et al., Engineering a de novo-designed coiled-coil heterodimerization domain off the rapid detection, purification and characterization of recombinantly expressed peptides and proteins, Protein Engng., 9:1029-42 (1996).
Tuerk, C. and Gold, L., Systematic Evolution of Ligands by Exponentid Enrichment: RNA Ligands to Bacteriophage T4 DNA Polymerase, Science, 249:505-10 (1990).
Umbanhowar et al., Monodisperse Emulsion Generation via Drop Break Off in a Coflowing Stream, Langmuir 16(2):347-351 (2000).
Unger et al., Monolithic microfabricated valves and pumps by multylayer soft lithography, Science 288(5463):113-116 (2000).
Utada, A. et al., Monodisperse double emulsions generated from a microcapillary device, Science, 308:537-541 (2005).
Vainshtein et al., Peptide rescue of an N-terminal truncation of the stoffel fragment of Taq DNA polymerase, Protein Science, 5:1785-92 (1996).
Van Bockstaele et al., Prognostic markers in chronic lymphocytic leukemia: a comprehensive review, Blood Rev 23(1):25-47 (2009).
Van Dilla et al., Cell Microfluorometry: A Method for Rapid Fluorescence Measurement, Science 163(3872):1213-1214 (1969).
Van Dilla et al., The fluorescent cell photometer: a new method for the rapid measurement of biological cells stained with fluorescent dyes, Annual Report of the Los Alamos Scientific Laboratory of the University of California (Los Alamos, NM), Biological and Medical Research Groupp (H-4) of the Health Division, Compiled by D. G. Ott, pp. 100-105, distributed Jan. 23, 1968.
Vanhooke et al., Three-dimensional structure of the zinc-containing phosphotrieesterase with the bound substrate analog diethy 4-methylbenzylphosphonate, Biochemistry 35:6020-6025 (1996).
Varga, J.M. et al., Mechanism of allergic cross-reactions-I. Multispecific binding of ligands to a mouse monoclonal anti-DNP IgE antibody. Mol Immunol 28(6), 641-54 (1991).
Vary, A homogeneous nucleic acid hybridization assay based on strand displacement, Nucl Acids Res 15(17):6883-6897 (1987).
Venkateswaran et al., Production of Anti-Fibroblast Growth Factor Receptor Monoclonal Antibodies by In Vitro Immunization, Hybirdoma, 11(6):729-739 (1992).
Venter et al., The sequence of the human genome, Science 291(5507):1304-51 (2001).
Vogelstein et al., Digital PCR, PNAS 96(16):9236-9241 (1999).
Voss, E.W., Kinetic measurements of molecular interactions by spectrofluorometry, J Mol Recognit, 6:51-58 (1993).
Wahler, D. et al., Novel methods for biocatalyst screening. Curr Opin Chem Biol, 5: 152-158 (2001).
Walde, P. et al., Oparin's reactions revisited: enzymatic synthesis of poly(adenylic acid) in micelles and self-reproducing vesicles. J Am Chem Soc, 116: 7541-7547 (1994).
Walde, P. et al., Spectroscopic and kinetic studies of lipases solubilized in reverse micelles, Biochemistry, 32(15):4029-34 (1993).
Walde, P. et al., Structure and activity of trypsin in reverse micelles, Eur J Biochem, 173(2):401-9 (1988).
Walker et al., Isothermal in vitro amplification of DNA by a restriction enzyme/DNA polymerase system, PNAS 89(1):392-6 (1992).
Walker et al., Strand displacement amplification—an isothermal, in vitro DNA amplification technique, Nucleic Acid Res, 20(7):1691-6 (1992).
Wang et al., DEP actuated nanoliter droplet dispensing using feedback control, Lab on a Chip 9:901-909 (2008).
Wang et al., Preparation of Titania Particles Utilizing the Insoluble Phase Interface in a MicroChannel Reactor, Chemical Communications 14:1462-1463 (2002).
Wang, A.M. et al., Quantitation of mRNA by the polymerase chain reaction. Proc natl Acad Sci USA 86(24), 9717-21 (1989).
Wang, G.T. et al., Design and synthesis of new fluorogenic HIV protease substrates based on resonance energy transfer, Tetrahedron Lett., 31:6493 (1990).
Warburton, B., Microcapsules for Multiple Emulsions, Encapsulation and Controlled Release, Spec Publ R Soc Chem, 35-51 (1993).
Wasserman et al., Structure and reactivity of allyl-siloxane monolayers formed by reaction of allcyltrichlorosilanes on silicon substrates, Langmuir 5:1074-1087 (1989).
Weil. et al., Selective and accurate initiation of transcription at the Ad2 major late promotor in a soluble system dependent on purified RNA polymerase II and DNA, Cell, 18(2):469-84 (1979).
Werle et al., Convenient single-step, one tube purification of PCR products for direct sequencing, Nucl Acids Res 22(20):4354-4355 (1994).
Wetmur et al., Molecular haplotyping by linking emulsion PCR: analysis of paraoxonase 1 haplotypes and phenotypes, Nucleic Acids Res 33(8):2615-2619 (2005).
Wick et al., Enzyme-containing liposomes can endogenously produce membrane-constituting lipids, Chem Biol 3(4):277-85 (1996).
Widersten and Mannervik, Glutathione Transferases with Novel Active Sites Isolated by Phage Display from a Library of Random Mutants, J Mol Biol 250(2):115-22 (1995).
Wiggins et al., Foundations of chaotic mixing, Philos Transact a Math Phys Eng Sci 362(1818):937-70 (2004).
Williams et al., Amplification of complex gene libraries by emulsion PCR, Nature Methods 3(7):545-550 (2006).
Williams et al., Methotrexate, a high-affinity pseudosubstrate of dihydrofolate reductase, Biochemistry, 18(12):2567-73 (1979).
Wilson, D.S. and Szostak, J.W., In vitro selection of functional nucleic acids, Ann. Rev. Biochem. 68: 611-647 (1999).
Winter et al., Making antibodies by phage display technology, Annu Rev Immunol 12:433-55 (1994).
Wittrup, K.D., Protein engineering by cell-surface display. Curr Opin Biotechnology, 12: 395-399 (2001).
Wolff et al., Integrating advanced functionality in a microfabricated high-throughput fluorescent-activated cell sorter, Lab Chip, 3(1): 22-27 (2003).
Wronski et al., Two-color, fluorescence-based microplate assay for apoptosis detection. Biotechniques, 32:666-668 (2002).

(56) References Cited

OTHER PUBLICATIONS

Wu et al., The ligation amplification reaction (LAR)-amplification of specific DNA sequences using sequential rounds of template-dependent ligation, Genomics 4(4):560-9 (1989).

Wyatt et al., Synthesis and purification of large amounts of RNA oligonucleotides, Biotechniques 11(6):764-9 (1991).

Xia and Whitesides, Soft Lithography, Angew. Chem. Int. Ed. 37:550-575 (1998).

Xia and Whitesides, Soft Lithography, Ann. Rev. Mat. Sci. 28:153-184 (1998).

Xu, S. et al., Generation of monodisperse particles by using microfluidics: control over size, shape, and composition, Angew. Chem. Int. Ed. 44:724-728 (2005).

Yamagishi, J. et al., Mutational analysis of structure-activity relationships in human tumor necrosis factor-alpha, Protein Eng, 3:713-9 (1990).

Yamaguchi et al., Insulin-loaded biodegradable PLGA microcapsules: initial burst release controlled by hydrophilic additives, Journal of Controlled Release, 81(3): 235-249 (2002).

Yelamos, J. et al., Targeting of non-Ig sequences in place of the V segment by somatic hypermutation. Nature 376(6537):225-9 (1995).

Yershov et al., DNA analysis and diagnostics on oligonucleotide microchips, PNAS 93(10):4913-4918 (1996).

Yonezawa et al., DNA display for in vitro selection of diverse peptide libraries, Nucleic Acids Research, 31(19): e118 (2203).

Yu et al. Responsive biomimetic hydrogel valve for microfluidics. Appl. Phys. Lett 78:2589-2591 (2001).

Yu et al., Quantum dot and silica nanoparticle doped polymer optical fibers, Optics Express 15(16):9989-9994 (2007).

Yu et al., Specifc inhibition of PCR by non-extendable oligonucleotides using a 5{ to 3{ exonuclease-deficient DNA polymerase, Biotechniques 23(4):714-6, 718-20 (1997).

Zaccolo, M. et al., An approach to random mutagenesis of DNA using mixtures of triphosphate derivatives of nucleoside analogues. J Mol Biol 255(4):589-603 (1996).

Zakrzewski, S.F., Preparation of tritiated dihydrofolic acid of high specific activity, Methods Enzymol, 539 (1980).

Zaug and Cech, The intervening sequence RNA of Tetrahymena is an enzyme, Science 231(4737):470-5 (1986).

Zaug and Cech, The Tetrahymena intervening sequence ribonucleic acid enzyme is a phosphotransferase and an acid phosphatase, Biochemistry 25(16):4478-82 (1986).

Zaug et al., The Tetrahymena ribozyme acts like an RNA restriction endonuclease, Nature 324(6096):429-33 (1986).

Zhang et al., A Simple Statistical Parameter for Use in Evaluation and Validation of High Throughput Screening Assays, Journal of Biomolecular Screening, 4(2): 67-73 (1999).

Zhang, Z.Y., Substrate specificity of the protein tyrosine phosphatases, PNAS 90: 4446-4450 (1993).

Zhao, B. et al., Control and Applications of Immiscible Liquids in Microchannels, J. Am. Chem. Soc, vol. 124:5284-5285 (2002).

Zhao, H. et al., Molecular evolution by staggered extension process (StEP) in vitro recombination. Nat Biotechnol 16(3):258-61 (1998).

Zheng et al., A Droplet-Based, Composite PDMS/Glass Capillary Microfluidic System for Evaluating Protein Crystallization Conditions by Microbatch and Vapor-Diffusion Methods with On-Chip X-Ray Diffraction, Angew. Chem., pp. 1-4, 2004.

Zheng et al., A Microiuidic Approach for Screening Submicroliter Volumes against Multiple Reagents by Using Performed Arrays of Nanoliter Plugs in a Three-Phase Liquid/Liquid/Gas Flow, Angew. Chem. Int. Ed., 44(17): 2520-2523 (2005).

Zheng et al., Formation of Droplets of Alternating Composition in Microfluidic Channels and Applications to Indexing of Concentrations in Droplet-Based /Assays, Anal. Chem.,76: 4977-4982 (2004).

Zheng et al., Screening of Protein Crystallization Conditions on a Microfluidic Chip Using Nanoliter-Size Droplets, J Am Chem Soc 125(37):11170-11171 (2003).

Zimmermann et al., Dielectric Breakdown of Cell Membranes, Biophys J 14(11):881-889 (1974).

Zimmermann et al., Microscale Production of Hybridomas by Hypo-Osmolar Electrofusion, Hum. Antibod. Hybridomas, 3(1): 14-18 (1992).

Zubay, G., In vitro synthesis of protein in microbial systems, Annu Rev Genet, 7: 267-87 (1973).

Zubay, G., The isolation and properties of CAP, the catabolite gene activator, Methods Enzymol, 65: 856-77 (1980).

Zuckermann, R. et al., Efficient Methods for Attachment of Thiol-Specific Probes to the 3{-end of Synthetic Oligodeoxyribonucleotides, Nucleic Acids Res. 15:5305-5321 (1987).

* cited by examiner

SEQUENCE LISTING

<160> NUMBER OF SEQ ID NOS: 1

<210> SEQ ID NO 1
<211> LENGTH: 11
<212> TYPE: PRT
<213> ORGANISM: Homo sapiens

<400> SEQUENCE: 1

Asp Ala Asp Glu Tyr Leu Ile Pro Gln Gln Gly
1               5                   10

SELECTION BY COMPARTMENTALISED SCREENING

RELATED APPLICATION

The present application is a continuation of and claims priority to U.S. patent application Ser. No. 11/238,258, filed Sep. 29, 2005, which is a continuation of and claims priority to PCT application number PCT/GB2004/001362, filed Mar. 31, 2004, which claims the benefit of and priority to Great Britain application serial number 0307403.6, filed Mar. 31, 2003, the content of each of which is hereby incorporated by reference herein in its entirety.

The present invention relates to a method for selection of compounds from a library of compounds by screening in microcapsules. The method of the invention is particularly applicable to selection of low molecular weight compounds such as candidate drugs for potential activity against any desired drug target.

BACKGROUND TO THE INVENTION

The present invention relates to methods for use in the identification of molecules which bind to a target component of a biochemical system or modulate the activity of a target.

Over the past decade, high-throughput screening (HTS) of compound libraries has become a cornerstone technology of pharmaceutical research. Investment into HTS is substantial. A current estimate is that biological screening and preclinical pharmacological testing alone account for ~14% of the total research and development (R&D) expenditures of the pharmaceutical industry (Handen, Summer 2002). HTS has seen significant improvements in recent years, driven by a need to reduce operating costs and increase the number of compounds and targets that can be screened. Conventional 96-well plates have now largely been replaced by 384-well, 1536-well and even 3456-well formats. This, combined with commercially available plate-handling robotics allows the screening of 100,000 assays per day, or more, and significantly cuts costs per assay due to the miniaturisation of the assays.

HTS is complemented by several other developments. Combinatorial chemistry is a potent technology for creating large numbers of structurally related compounds for HTS. Currently, combinatorial synthesis mostly involves spatially resolved parallel synthesis. The number of compounds that can be synthesised is limited to hundreds or thousands but the compounds can be synthesised on a scale of milligrams or tens of milligrams, enabling full characterisation and even purification. Larger libraries can be synthesised using split synthesis on beads to generate one-bead-one compound libraries. This method is much less widely adopted due to a series of limitations including: the need for solid phase synthesis; difficulties characterising the final products (due to the shear numbers and small scale); the small amounts of compound on a bead being only sufficient for one or a few assays; the difficulty in identifying the structure of a hit compound, which often relies on tagging or encoding methods and complicates both synthesis and analysis. Despite this split synthesis and single bead analysis still has promise. Recently there have been significant developments in miniaturised screening and single bead analysis. For example, printing techniques allow protein-binding assays to be performed on a slide containing 10,800 compound spots, each of 1 nl volume (Hergenrother et al., 2000). Combichem has so far, however, generated only a limited number of lead compounds. As of April 2000, only 10 compounds with a combinatorial chemistry history had entered clinical development and all but three of these are (oligo)nucleotides or peptides (Adang and Hemikens, 2001). Indeed, despite enormous investments in both HTS and combinatorial chemistry during the past decade the number of new drugs introduced per year has remained constant at best.

Dynamic combinatorial chemistry (DCC) can also be used to create dynamic combinatorial libraries (DCLs) from a set of reversibly interchanging components, however the sizes of libraries created and screened to date are still fairly limited ($\leq 40,000$) (Ramstrom and Lehn, 2002).

Virtual screening (VS) (Lyne, 2002), in which large compound bases are searched using computational approaches to identify a subset of candidate molecules for testing may also be very useful when integrated with HTS. However, there are to date few studies that directly compare the performance of VS and HTS, and further validation is required.

Despite all these developments, current screening throughput is still far from adequate. Recent estimates of the number of individual genes in the human genome (~30,000) and the number of unique chemical structures theoretically attainable using existing chemistries suggests that an enormous number of assays would be required to completely map the structure-activity space for all potential therapeutic targets (Burbaum, 1998).

Hence, the provision of a method which permits screening vast numbers ($\geq 10^{10}$) of compounds quickly, using reaction volumes of only a few femtoliters, and at very low cost would be of enormous utility in the generation of novel drug leads.

Tawfik and Griffiths (1998), and International patent application PCT/GB98/01889, describe a system for in vitro evolution using compartmentalisation in microcapsules to link genotype and phenotype at the molecular level. In Tawfik and Griffiths (1998), and in several embodiments of International patent application PCT/GB98/01889, the desired activity of a gene product results in a modification of the genetic element which encoded it (and is present in the same microcapsule). The modified genetic element can then be selected in a subsequent step.

SUMMARY OF THE INVENTION

We have now developed a methodology for selection of compounds, not encoded by genetic elements, using a compartmentalised microcapsule system based on that described in Griffiths & Tawfik (1998). The novel method according to the present invention permits the rapid, high-throughput screening of compounds for activity against a target at low cost in a manner compatible with modern HTS approaches.

In a first aspect, there is provided a method for identifying a compound or compounds in a repertoire of compounds, which compound or compound(s) possess(es) a desired activity, comprising the steps of:
  a) compartmentalising the compounds into microcapsules, such that only a subset of the repertoire is represented in multiple copies in any one microcapsule;
  b) identifying the compounds which possess the desired activity.

Preferably, the desired activity is selected from the group consisting of a binding activity and the modulation of the activity of a target. The target is advantageously compartmentalised into microcapsules together with the compound(s), allowing the activity of the compound(s) on the target to be measured within the microcapsule which links the target and the compound together.

Preferably, the subset of the repertoire present in any one microcapsule is a single compound. Each microcapsule contains multiple molecules of the subset of the repertoire, which is advantageously multiple copies of a single compound.

Compounds can be screened in accordance with the invention by screening for a change in a microcapsule containing a compound. In a preferred embodiment, the microcapsules are modified by the action of the compound(s) such as to change their optical properties.

The change in optical properties of the microcapsule can be due to a change in the optical properties of the compound when bound to target or to a change in the optical properties of the target when bound by the compound. Moreover, the change in optical properties of the microcapsule can be due to a change in the optical properties of both target and compound on binding.

The change in the optical properties of the microcapsule may be due to modulation of the activity of the target by the compound. The compound may activate or inhibit the activity of the target. For example, if the target is an enzyme, the substrate and the product of the reaction catalysed by the target can have different optical properties. Advantageously, the substrate and product have different fluorescence properties.

It is to be understood that the detected change in the microcapsule may be caused by the direct action of the compound, or indirect action, in which a series of reactions, one or more of which involve the compound having the desired activity leads to the detected change.

The compounds in a microcapsule can be identified using a variety of techniques familiar to those skilled in the art, including mass spectroscopy, chemical tagging or optical tagging. Advantageously, the compounds are contained in optically tagged microcapsules to enable the identification of the microcapsule and the compound contained in it.

Advantageously, the microcapsules are analysed by detection of a change in their fluorescence. For example, microcapsules can be analysed by flow cytometry and, optionally sorted using a fluorescence activated cell sorter (FACS). The different fluorescence properties of the target and the product can be due to fluorescence resonance energy transfer (FRET).

In a further embodiment, the internal environment of the microcapsules can be modified by the addition of one or more reagents to the oil phase. This allows reagents to be diffused in to the microcapsules during the reaction, if necessary.

According to a preferred implementation of the present invention, the compounds may be screened according to an activity of the compound or derivative thereof which makes the microcapsule detectable as a whole. Accordingly, the invention provides a method wherein a compound with the desired activity induces a change in the microcapsule, or a modification of one or more molecules within the microcapsule, which enables the microcapsule containing the compound to be identified. In this embodiment, therefore, the microcapsules are either: (a) physically sorted from each other according to the activity of the compound(s) contained therein, and the contents of the sorted microcapsules analysed to determine the identity of the compound(s) which they contain; or (b) analysed directly without sorting to determine the identity of the compound(s) which the microcapsules contain.

Preferably, microencapsulation is achieved by forming a water-in-oil emulsion.

Compartmentalisation of a subset of a repertoire in multiple copies may be achieved in a number of ways. For example, compounds may be attached to beads, and the emulsion formed such that substantially only a single bead is included in each compartment. Step (a) above is thus modified, such that it comprises
  a) attaching the repertoire of compounds onto microbeads, such that only a subset of the repertoire is represented on any one microbead;
  b) compartmentalising the microbeads into microcapsules;
such that a subset of the repertoire is represented in multiple copies in any one microcapsule.

Thus, in a further aspect, there is provided a method for identifying a compound or compounds in a repertoire of compounds, which compound or compound(s) possess(es) a desired activity, comprising the steps of:
  4. attaching the repertoire of compounds onto microbeads, such that only a subset of the repertoire is represented on any one microbead;
  5. compartmentalising the microbeads into microcapsules;
  6. optionally, releasing compounds from the microbeads; and
  7. identifying the compounds which possess the desired activity.

Preferably, the subset of the repertoire present on any one microbead is a single compound. Advantageously, each microbead has attached thereto multiple molecules of a single compound.

Preferably, compounds are attached to microbeads by means of cleavable linkers, for example photocleavable linkers, which permit the release of the compound from the microbead if desired.

Compounds can be screened in accordance with the invention by screening either for a change in a microcapsule containing a compound or a change in or on a microbead to which a compound is attached.

The compounds on beads can be identified using a variety of techniques familiar to those skilled in the art, including mass spectroscopy, chemical tagging or optical tagging.

Advantageously, the compounds are coupled to optically tagged microbeads to enable the identification of the bead and the compound coupled to it in step (d).

Repertoires may also be emulsified in different ways to achieve encapsulation of multiple copies of a single compound.

For example, an aqueous solution of each compound can be compartmentalised in the microcapsules of a water-in-oil emulsion and then aliquots of the emulsions containing the different compounds mixed. Microcapsules can normally also contain a target and the activity of the target can be suppressed by keeping the microcapsules cold.

In a further embodiment, small aliquots of an aqueous solution of each compound can be deposited into an oil phase (advantageously containing surfactants and/or other stabilising molecules) whilst applying mechanical energy, thereby dispersing each compound into multiple aqueous microcapsules, each of which contains (for the most part) a single sort of compound but multiple copies thereof. Advantageously, the compounds can be deposited into the oil phase in the form of droplets generated using inkjet printing technology (Calvert, 2001; de Gans et al., 2004), and more advantageously by piezoelectric drop-on-demand (DOD) inkjet printing technology. Inkjet printing technology can also be used to mix reagents (e.g. the compound, the target and reagents to assay target activity) immediately prior to forming the emulsion. Advantageously, multiple compounds can be mixed with multiple targets in a combinatorial manner. This approach achieves a similar result, forming individual emulsions in situ in the oil phase from the aqueous droplets, which are subsequently mixed.

Thus, step (a) above can be modified such that it comprises forming separate emulsion compartments containing individual compounds and mixing the emulsion compartments to form an emulsified compound repertoire wherein a subset of the repertoire is represented in multiple copies in any one microcapsule.

Moreover, compound libraries can be compartmentalised in highly monodisperse microcapsules produced using microfluidic techniques. For example, aliquots of each compound can be compartmentalised into one or more aqueous microcapsules (with less than 3% polydispersity) in water-in-oil emulsions created by droplet break off in a co-flowing steam of oil (Umbanhowar et al., 2000). Advantageously, the aqueous microcapsules are then transported by laminar-flow in a stream of oil in microfluidic channels (Thorsen et al., 2001). These microcapsules containing single compounds can, optionally, be split into two or more smaller microcapsules using microfluidics (Link et al., 2004; Song et al., 2003). The microcapsules containing single compounds can, optionally be fused with other microcapsules (Song et al., 2003) containing a target. A single microcapsule containing a target can, optionally, be split into two or more smaller microcapsules which can subsequently be fused with microcapsules containing different compounds, or compounds at different concentrations. Advantageously, a compound and a target can be mixed by microcapsule fusion prior to a second microcapsule fusion which delivers the necessary to assay the activity of the target (e.g. the substrate for the target if the target is an enzyme). This allows time for the compound to bind to the target. The microcapsules can be analysed and, optionally, sorted using microfluidic devices (Fu et al., 2002).

According to a preferred implementation of the present invention, the screening of compounds may be performed by, for example:

(I) In a first embodiment, the microcapsules are screened according to an activity of the compound or derivative thereof which makes the microcapsule detectable as a whole. Accordingly, the invention provides a method wherein a compound with the desired activity induces a change in the microcapsule, or a modification of one or more molecules within the microcapsule, which enables the microcapsule containing the compound to be identified. In this embodiment, therefore, the microcapsules are either: (a) physically sorted from each other according to the activity of the compound(s) contained therein, the contents of the sorted microcapsules optionally pooled into one or more common compartments, and the microcapsule contents analysed to determine the identity of the compound(s); or (b) analysed directly without sorting to determine the identity of the compound(s) which the microcapsules contained. Where the microcapsule contains microbeads, the microbeads can be analysed to determine the compounds with which they are coated.

(II) In a second embodiment, microbeads are analysed following pooling of the microcapsules into one or more common compartments. In this embodiment, a compound having the desired activity modifies the microbead which carried it (and which resides in the same microcapsule) in such a way as to make it identifiable in a subsequent step. The reactions are stopped and the microcapsules are then broken so that all the contents of the individual microcapsules are pooled. Modified microbeads are identified and either: (a) physically sorted from each other according to the activity of the compound(s) coated on the microbeads, and the sorted microbeads analysed to determine the identity of the compound(s) with which they are/were coated; or (b) analysed directly without sorting to determine the identity of the compound(s) with which the microbeads are/were coated. It is to be understood, of course, that modification of the microbead may be direct, in that it is caused by the direct action of the compound, or indirect, in which a series of reactions, one or more of which involve the compound having the desired activity, leads to modification of the microbead. Advantageously, the target is bound to the microbead and is a ligand and the compound within the microcapsule binds, directly or indirectly, to said ligand to enable the isolation of the microbead. In another configuration, a substrate for the target is and is bound to the microbead, and the activity of the compound within the microcapsule results, directly or indirectly, in the conversion of said substrate into a product which remains part of the microbead and enables its isolation. Alternatively, the activity of the compound may prevent or inhibit the conversion of said substrate into product. Moreover, the product of the activity of the compound within the microcapsule can result, directly or indirectly, in the generation of a product which is subsequently complexed with the microbead and enables its identification.

(III) In a third embodiment, the microbeads are analysed following pooling of the microcapsules into one or more common compartments. In this embodiment, a compound with a desired activity induces a change in the microcapsule containing the compound and the microbead which carries it. This change, when detected, triggers the modification of the microbead within the compartment. The reactions are stopped and the microcapsules are then broken so that all the contents of the individual microcapsules are pooled. Modified microbeads are identified and either: (a) physically sorted from each other according to the activity of the compound(s) coated on the microbeads, and the sorted microbeads analysed to determine the identity of the compound(s) with which they are/were coated; or (b) analysed directly without sorting to determine the identity of the compound(s) with which the microbeads are/were coated.

The microcapsules or microbeads may be modified by the action of the compound(s) such as to change their optical properties. For example, the modification of the microbead can enable it to be further modified outside the microcapsule so as to induce a change in its optical properties.

In another embodiment, the change in optical properties of the microcapsule or microbead is due to binding of a compound with distinctive optical properties to the target.

Moreover, the change in optical properties of the microcapsule or microbead can be due to binding of a target with distinctive optical properties by the compound.

The change in optical properties of the microcapsule or microbead can be due to a change in the optical properties of the compound when bound to target or to a change in the optical properties of the target when bound by the compound. Moreover, the change in optical properties of the microcapsule or microbead can be due to a change in the optical properties of both target and compound on binding.

The change in the optical properties of the microcapsule may be due to modulation of the activity of the target by the compound. The compound may activate or inhibit the activity of the target. For example, if the target is an enzyme, the substrate and the product of the reaction catalysed by the target can have different optical properties. Advantageously, the substrate and product have different fluorescence properties. In the case where the microcapsules contain microbeads, both the substrate and the product can have similar optical properties, but only the product of the reaction, and not the substrate, binds to, or reacts with, the microbead, thereby changing the optical properties of the microbead.

In a further configuration, further reagents specifically bind to, or specifically react with, the product (and not the substrate) attached to or contained in the microcapsule or microbead, thereby altering the optical properties of the microcapsule or microbead.

Advantageously, microcapsules or microbeads are modified directly or indirectly by the activity of the compound are further modified by Tyramide Signal Amplification (TSA™; NEN), resulting directly or indirectly in a change in the optical properties of said microcapsules or microbeads thereby enabling their separation.

Where the compounds are attached to beads, the density with which compounds are coated onto the microbeads, combined with the size of the microcapsule will determine the concentration of the compound in the microcapsule. High compound coating densities and small microcapsules will both give higher compound concentrations which may be advantageous for the selection of molecules with a low affinity for the target. Conversely, low compound coating densities and large microcapsules will both give lower compound concentrations which may be advantageous for the selection of molecules with a high affinity for the target.

The microbead can be nonmagnetic, magnetic or paramagnetic.

Advantageously, the microcapsules or microbeads are analysed by detection of a change in their fluorescence. For example, microbeads can be analysed by flow cytometry and, optionally sorted using a fluorescence activated cell sorter (FACS). The different fluorescence properties of the target and the product can be due to fluorescence resonance energy transfer (FRET).

The invention also provides for a product when identified according to the invention. As used in this context, a "product" may refer to any compound, selectable according to the invention.

Further embodiments of the invention are described in the detailed description below and in the accompanying claims.

DETAILED DESCRIPTION OF THE INVENTION

Definitions

Figure 1:
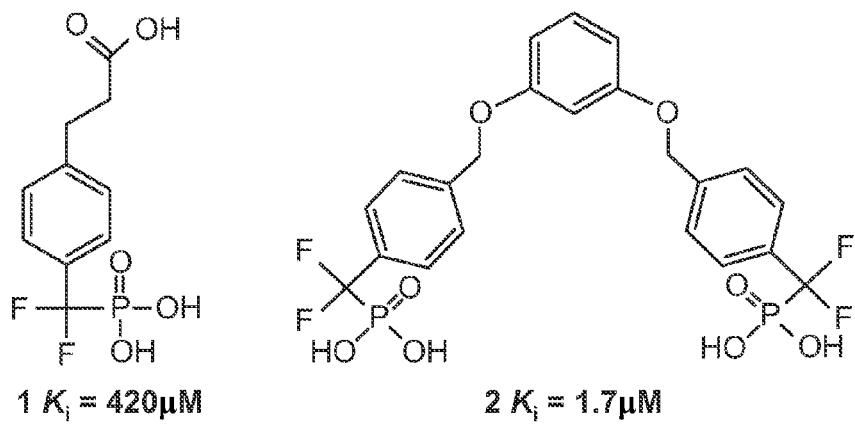
FIG. 1. Examples of PTP1B inhibitors. Compounds with a bis-difluoromethylene phosphonate moiety (e.g. 2) have significantly more potency than those with a single moiety (e.g. 1).

The term "microcapsule" is used herein in accordance with the meaning normally assigned thereto in the art and further described hereinbelow. In essence, however, a microcapsule is an artificial compartment whose delimiting borders restrict the exchange of the components of the molecular mechanisms described herein which allow the identification of the molecule with the desired activity. The delimiting borders preferably completely enclose the contents of the microcapsule. Preferably, the microcapsules used in the method of the present invention will be capable of being produced in very large numbers, and thereby to compartmentalise a library of compounds. Optionally, the compounds can be attached to microbeads. The microcapsules used herein allow mixing and sorting to be performed thereon, in order to facilitate the high throughput potential of the methods of the invention. Arrays of liquid droplets on solid surfaces, and multiwell plates, are not microcapsules as defined herein.

The term "microbead" is used herein in accordance with the meaning normally assigned thereto in the art and further described hereinbelow. Microbeads, are also known by those skilled in the art as microspheres, latex particles, beads, or minibeads, are available in diameters from 20 nm to 1 mm and can be made from a variety of materials including silica and a variety of polymers, copolymers and terpolymers. Highly uniform derivatised and non-derivatised nonmagnetic and paramagnetic microparticles (beads) are commercially available from many sources (e.g. Sigma, Bangs Laboratories, Luminex and Molecular Probes) (Fomusek and Vetvicka, 1986).

Microbeads can be "compartmentalised" in accordance with the present invention by distribution into microcapsules. For example, in a preferred aspect the microbeads can be placed in a water/oil mixture and emulsified to form a water-in-oil emulsion comprising microcapsules according to the invention. The concentration of the microbeads can be adjusted such that a single microbead, on average, appears in each microcapsule.

The term "compound" is used herein in accordance with the meaning normally assigned thereto in the art. The term compound is used in its broadest sense i.e. a substance comprising two or more elements in fixed proportions, including molecules and supramolecular complexes. This definition includes small molecules (typically <500 Daltons) which make up the majority of pharmaceuticals. However, the definition also includes larger molecules, including polymers, for example polypeptides, nucleic acids and carbohydrates, and supramolecular complexes thereof.

A "repertoire" of compounds is a group of diverse compounds, which may also be referred to as a library of compounds. Repertoires of compounds may be generated by any means known in the art, including combinatorial chemistry, compound evolution, such as by the method of our copending UK patent application entitled "Compartmentalised Combinatorial Chemistry" filed on even date herewith, or purchased from commercial sources such as Sigma Aldrich, Discovery Partners International, Maybridge and Tripos. A repertoire advantageously comprises at least $10^2$, $10^3$, $10^4$, $10^5$, $10^6$, $10^7$, $10^8$, $10^9$, $10^{10}$, $10^{11}$ or more different compounds, which may be related or unrelated in structure or function.

A "subset" of a repertoire is a part thereof, which may be a single compound or a group of compounds having related or unrelated structures. Advantageously, the subset is a single compound. Preferably, multiple copies of each compound are encapsulated in a microcapsule. Subsets of the repertoire, which may be attached to microbeads, are advantageously attached in multiple copies of each compound; for example, where each microbead has attached thereto only one compound, multiple molecules of that compound are attached to said microbead. The amount of compound attached to the microbead will determine the concentration of the compound in the microcapsule.

Compounds can be "released" from a microbead by cleavage of a linker which effects the attachment of the compound to the microbead. Release of the compounds from the microbead allows the compounds to interact more freely with other contents of the microcapsule, and to be involved in reactions therein and optionally to become combined with other reagents to form new compounds, complexes, molecules or supramolecular complexes. Cleavage of linkers can be performed by any means, with means such as photochemical cleavage which can be effected from without the microcapsule being preferred. Photochemically cleavable linkers are known in the art (see for example (Gordon and Balasubramanian, 1999)) and further described below.

As used herein, the "target" is any compound, molecule, or supramolecular complex. Typical targets include targets of medical significance, including drug targets such as receptors, for example G protein coupled receptors and hormone receptors; transcription factors, protein kinases and phosphatases involved in signalling pathways; gene products specific to microorganisms, such as components of cell walls, replicases and other enzymes; industrially relevant targets, such as enzymes used in the food industry, reagents intended for research or production purposes, and the like.

A "desired activity", as referred to herein, is the modulation of any activity of a target, or an activity of a molecule which is influenced by the target, which is modulatable directly or indirectly by a compound or compounds as assayed herein. The activity of the target may be any measurable biological or chemical activity, including binding activity, an enzymatic activity, an activating or inhibitory activity on a third enzyme or other molecule, the ability to cause disease or influence metabolism or other functions; and the like. Activation and inhibition, as referred to herein, denote the increase or decrease of a desired activity 1.5 fold, 2 fold, 3 fold, 4 fold, 5 fold, 10 fold, 100 fold or more. Where the modulation is inactivation, the inactivation can be substantially complete inactivation.

The desired activity may moreover be purely a binding activity, which may or may not involve the modulation of the activity of the target bound to.

A compound defined herein as "low molecular weight" or a "small molecule" is a molecule commonly referred to in the pharmaceutical arts as a "small molecule". Such compounds are smaller than polypeptides and other, large molecular complexes and can be easily administered to and assimilated by patients and other subjects. Small molecule drugs can advantageously be formulated for oral administration or intramuscular injection. For example, a small molecule may have a molecular weight of up to 2000 Dalton; preferably up to 1000 Dalton; advantageously between 250 and 750 Dalton; and more preferably less than 500 Dalton.

A "selectable change" is any change which can be measured and acted upon to identify or isolate the compound which causes it. The selection may take place at the level of the microcapsule, the microbead, or the compound itself, optionally when complexed with another reagent. A particularly advantageous embodiment is optical detection, in which the selectable change is a change in optical properties, which can be detected and acted upon for instance in a FACS device to separate microcapsules or microbeads displaying the desired change.

As used herein, a change in optical properties refers to any change in absorption or emission of electromagnetic radiation, including changes in absorbance, luminescence, phosphorescence or fluorescence. All such properties are included in the term "optical". Microcapsules or microbeads can be identified and, optionally, sorted, for example, by luminescence, fluorescence or phosphorescence activated sorting. In a preferred embodiment, flow cytometry is employed to identify and, optionally, sort microcapsules or microbeads. A variety of optical properties can be used for analysis and to trigger sorting, including light scattering (Kerker, 1983) and fluorescence polarisation (Rolland et al., 1985). In a highly preferred embodiment microcapsules or microbeads are analysed and, optionally, sorted using a fluorescence activated cell sorter (FACS) (Norman, 1980; Mackenzie and Pinder, 1986).

The compounds in microcapsules or on beads can be identified using a variety of techniques familiar to those skilled in the art, including mass spectroscopy, chemical tagging or optical tagging.

General Techniques

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) $4^{th}$ Ed, John Wiley & Sons, Inc. which are incorporated herein by reference) and chemical methods. In addition Harlow & Lane, A Laboratory Manual Cold Spring Harbor, N.Y., is referred to for standard Immunological Techniques.

(A) General Description

The microcapsules of the present invention require appropriate physical properties to allow the working of the invention.

First, to ensure that the compounds and the target may not diffuse between microcapsules, the contents of each microcapsule must be isolated from the contents of the surrounding microcapsules, so that there is no or little exchange of compounds and target between the microcapsules over the timescale of the experiment. However, the permeability of the microcapsules may be adjusted such that reagents may be allowed to diffuse into and/or out of the microcapsules if desired.

Second, the method of the present invention requires that there are only a limited number of different compounds per microcapsule. In the case that compounds are attached to beads, the method of the present invention requires that there are only a limited number of beads per microcapsule.

Third, the formation and the composition of the microcapsules advantageously does not abolish the activity of the target.

Consequently, any microencapsulation system used preferably fulfils these three requirements. The appropriate system(s) may vary depending on the precise nature of the requirements in each application of the invention, as will be apparent to the skilled person.

A wide variety of microencapsulation procedures are available (see Benita, 1996) and may be used to create the microcapsules used in accordance with the present invention. Indeed, more than 200 microencapsulation methods have been identified in the literature (Finch, 1993).

These include membrane enveloped aqueous vesicles such as lipid vesicles (liposomes) (New, 1990) and non-ionic surfactant vesicles (van Hal et al., 1996). These are closed-membranous capsules of single or multiple bilayers of non-covalently assembled molecules, with each bilayer separated from its neighbour by an aqueous compartment. In the case of liposomes the membrane is composed of lipid molecules; these are usually phospholipids but sterols such as cholesterol may also be incorporated into the membranes (New, 1990). A variety of enzyme-catalysed biochemical reactions, including RNA and DNA polymerisation, can be performed within liposomes (Chakrabarti et al., 1994; Oberholzer et al., 1995a; Oberholzer et al., 1995b; Walde et al., 1994; Wick & Luisi, 1996).

With a membrane-enveloped vesicle system much of the aqueous phase is outside the vesicles and is therefore non-compartmentalised. This continuous, aqueous phase should be removed or the biological systems in it inhibited or destroyed in order that the reactions are limited to the microcapsules (Luisi et al., 1987).

Enzyme-catalysed biochemical reactions have also been demonstrated in microcapsules generated by a variety of other methods. Many enzymes are active in reverse micellar solutions (Bru & Walde, 1991; Bru & Walde, 1993; Creagh et al., 1993; Haber et al., 1993; Kumar et al., 1989; Luisi & B., 1987; Mao & Walde, 1991; Mao et al., 1992; Perez et al., 1992; Walde et al., 1994; Walde et al., 1993; Walde et al., 1988) such as the AOT-isooctane-water system (Menger & Yamada, 1979).

Microcapsules can also be generated by interfacial polymerisation and interfacial complexation (Whateley, 1996). Microcapsules of this sort can have rigid, nonpermeable membranes, or semipermeable membranes. Semipermeable microcapsules bordered by cellulose nitrate membranes, polyamide membranes and lipid-polyamide membranes can all support biochemical reactions, including multienzyme systems (Chang, 1987; Chang, 1992; Lim, 1984). Alginate/polylysine microcapsules (Lim & Sun, 1980), which can be formed under very mild conditions, have also proven to be very biocompatible, providing, for example, an effective method of encapsulating living cells and tissues (Chang, 1992; Sun et al., 1992).

Non-membranous microencapsulation systems based on phase partitioning of an aqueous environment in a colloidal system, such as an emulsion, may also be used.

Preferably, the microcapsules of the present invention are formed from emulsions; heterogeneous systems of two immiscible liquid phases with one of the phases dispersed in the other as droplets of microscopic or colloidal size (Becher, 1957; Sherman, 1968; Lissant, 1974; Lissant, 1984).

Emulsions may be produced from any suitable combination of immiscible liquids. Preferably the emulsion of the present invention has water (containing the biochemical components) as the phase present in the form of finely divided droplets (the disperse, internal or discontinuous phase) and a hydrophobic, immiscible liquid (an 'oil') as the matrix in which these droplets are suspended (the nondisperse, continuous or external phase). Such emulsions are termed 'water-in-oil' (W/O). This has the advantage that the entire aqueous phase containing the biochemical components is compartmentalised in discreet droplets (the internal phase). The external phase, being a hydrophobic oil, generally contains none of the biochemical components and hence is inert.

The emulsion may be stabilised by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash and Ash, 1993). Suitable oils include light white mineral oil and decane. Suitable surfactants include: non-ionic surfactants (Schick, 1966) such as sorbitan monooleate (Span™80; ICI), sorbitan monostearate (Span™60; ICI), polyoxyethylenesorbitan monooleate (Tween™ 80; ICD, and octylphenoxyethoxyethanol (Triton X-100); ionic surfactants such as sodium cholate and sodium taurocholate and sodium deoxycholate; chemically inert silicone-based surfactants such as polysiloxane-polycetyl-polyethylene glycol copolymer (Cetyl Dimethicone Copolyol) (e.g. Abil™EM90; Goldschmidt); and cholesterol.

Emulsions with a fluorocarbon (or perfluorocarbon) continuous phase (Krafft et al., 2003; Riess, 2002) may be particularly advantageous. For example, stable water-in-perfluorooctyl bromide and water-in-perfluorooctylethane emulsions can be formed using F-alkyl dimorpholinophosphates as surfactants (Sadder et al., 1996). Non-fluorinated compounds are essentially insoluble in fluorocarbons and perfluorocarbons (Curran, 1998; Hildebrand and Cochran, 1949; Hudlicky, 1992; Scott, 1948; Studer et al., 1997) and small drug-like molecules (typically <500 Da and Log P<5) (Lipinski et al., 2001) are compartmentalised very effectively in the aqueous microcapsules of water-in-fluorocarbon and water-in-perfluorocarbon emulsions—with little or no exchange between microcapsules.

Creation of an emulsion generally requires the application of mechanical energy to force the phases together. There are a variety of ways of doing this which utilise a variety of mechanical devices, including stirrers (such as magnetic stir-bars, propeller and turbine stirrers, paddle devices and whisks), homogenisers (including rotor-stator homogenisers, high-pressure valve homogenisers and jet homogenisers), colloid mills, ultrasound and 'membrane emulsification' devices (Becher, 1957; Dickinson, 1994).

Complicated biochemical processes, notably gene transcription and translation are also active in aqueous microcapsules formed in water-in-oil emulsions. This has enabled compartmentalisation in water-in-oil emulsions to be used for the selection of genes, which are transcribed and translated in emulsion microcapsules and selected by the binding or catalytic activities of the proteins they encode (Doi and Yanagawa, 1999; Griffiths and Tawfik, 2003; Lee et al., 2002; Sepp et al., 2002; Tawfik and Griffiths, 1998). This was possible because the aqueous microcapsules formed in the emulsion were generally stable with little if any exchange of nucleic acids, proteins, or the products of enzyme catalysed reactions between microcapsules.

The technology exists to create emulsions with volumes all the way up to industrial scales of thousands of liters (Becher, 1957; Sherman, 1968; Lissant, 1974; Lissant, 1984).

The preferred microcapsule size will vary depending upon the precise requirements of any individual screening process that is to be performed according to the present invention. In all cases, there will be an optimal balance between the size of the compound library and the sensitivities of the assays to determine the identity of the compound and target activity.

The size of emulsion microcapsules may be varied simply by tailoring the emulsion conditions used to form the emulsion according to requirements of the screening system. The larger the microcapsule size, the larger is the volume that will be required to encapsulate a given compound library, since the ultimately limiting factor will be the size of the microcapsule and thus the number of microcapsules possible per unit volume.

Water-in-oil emulsions can be re-emulsified to create water-in-oil-in water double emulsions with an external (continuous) aqueous phase. These double emulsions can be analysed and, optionally, sorted using a flow cytometer (Bernath et al., 2004).

Highly monodisperse microcapsules can be produced using microfluidic techniques. For example, water-in-oil emulsions with less than 3% polydispersity can be generated by droplet break off in a co-flowing steam of oil (Umbanhowar et al., 2000). Microfluidic systems can also be used for laminar-flow of aqueous microdroplets dispersed in a stream of oil in microfluidic channels (Thorsen et al., 2001). This allows the construction of microfluidic devices for flow analysis and, optionally, flow sorting of microdroplets (Fu et al., 2002).

Microcapsules can, advantageously, be fused or split. For example, aqueous microdroplets can be merged and split using microfluidics systems (Link et al., 2004; Song et al., 2003). Microcapsule fusion allows the mixing of reagents. Fusion, for example, of a microcapsule containing the target with a microcapsule containing the compound could initiate the reaction between target and compound. Microcapsule splitting allows single microcapsules to be split into two or more smaller microcapsules. For example a single microcapsule containing a compound can be split into multiple microcapsules which can then each be fused with a different microcapsule containing a different target. A single microcapsule containing a target can also be split into multiple microcapsules which can then each be fused with a different microcapsule containing a different compound, or compounds at different concentrations.

Microcapsules can be optically tagged by, for example, incorporating fluorochromes. In a preferred configuration, the microcapsules are optically tagged by incorporating quantum dots: quantum dots of 6 colours at 10 concentrations would allow the encoding of $10^6$ microcapsules (Han et al., 2001). Microcapsules flowing in an ordered sequence in a microfluidic channel can be encoded (wholly or partially) by their sequence in the stream of microcapsules (positional encoding).

Microbeads, also known by those skilled in the art as microspheres, latex particles, beads, or minibeads, are available in diameters from 20 nm to 1 mm and can be made from a variety of materials including silica and a variety of polymers, copolymers and terpolymers including polystyrene (PS), polymethylmethacrylate (PMMA), polyvinyltoluene (PVT), styrene/butadiene (S/B) copolymer, and styrene/vinyltoluene (S/VT) copolymer. They are available with a variety of surface chemistries from hydrophobic surfaces (e.g. plain polystyrene), to very hydrophilic surfaces imparted by a wide variety of functional surface groups: aldehyde, aliphatic amine, amide, aromatic amine, carboxylic acid, chloromethyl, epoxy, hydrazide, hydroxyl, sulfonate and tosyl. The functional groups permit a wide range of covalent coupling reactions for stable or reversible attachment of compounds to the microbead surface.

Microbeads can be optically tagged by, for example, incorporating fluorochromes. For example, one hundred different bead sets have been created, each with a unique spectral address due to labelling with precise ratios of red (>650 nm) and orange (585 nm) fluorochromes (Fulton et al., 1997) and sets of up to $10^6$ beads can be encoded by incorporating quantum dots of 10 intensities and 6 colours (Han et al., 2001).

The compounds can be connected to the microbeads either covalently or non-covalently by a variety of means that will be familiar to those skilled in the art (see, for example, (Hermanson, 1996)). Advantageously, the compounds are attached via a cleavable linker. A variety of such linkers are familiar to those skilled in the art (see for example (Gordon and Balasubramanian, 1999)), including for example, linkers which can be cleaved photochemically and reversible covalent bonds which can be controlled by changing the pH (e.g. imines and acylhydrazones), by adjusting the oxido-reductive properties (e.g. disulphides), or using an external catalyst (e.g. cross-metathesis and transamidation).

The method of the present invention permits the identification of compounds which modulate the activity of the target in a desired way in pools (libraries or repertoires) of compounds.

The method of the present invention is useful for screening repertoires or libraries of compounds. The invention accordingly provides a method according to preceding aspects of the invention, wherein the compounds are identified from a library of compounds.

The compounds identified according to the invention are advantageously of pharmacological or industrial interest, including activators or inhibitors of biological systems, such as cellular signal transduction mechanisms suitable for diagnostic and therapeutic applications. In a preferred aspect, therefore, the invention permits the identification of clinically or industrially useful products. In a further aspect of the invention, there is provided a product when isolated by the method of the invention.

The selection of suitable encapsulation conditions is desirable. Depending on the complexity and size of the compound library to be screened, it may be beneficial to set up the encapsulation procedure such that one compound (or one or less than one microbead) is encapsulated per microcapsule. This will provide the greatest power of resolution. Where the library is larger and/or more complex, however, this may be impracticable; it may be preferable to encapsulate several compounds (or several microbeads) together and rely on repeated application of the method of the invention to identify the desired compound. A combination of encapsulation procedures may be used to identify the desired compound.

Theoretical studies indicate that the larger the number of compounds created the more likely it is that a compound will be created with the properties desired (see (Perelson and Oster, 1979) for a description of how this applies to repertoires of antibodies). It has also been confirmed practically that larger phage-antibody repertoires do indeed give rise to more antibodies with better binding affinities than smaller repertoires (Griffiths et al., 1994). To ensure that rare variants are generated and thus are capable of being identified, a large library size is desirable. Thus, the use of optimally small microcapsules is beneficial.

The largest repertoires of compounds that can be screened in a single experiment to date, using two dimensional microarrays of 1 nl volume spots, is ~$10^3$ (Hergenrother et al., 2000). Using the present invention, at a microcapsule diameter of 2.6 mm (Tawfik and Griffiths, 1998), by forming a three-dimensional dispersion, a repertoire size of at least $10^{11}$ can be screened using 1 ml aqueous phase in a 20 ml emulsion.

In addition to the compounds, or microbeads coated with compounds, described above, the microcapsules according to the invention will comprise further components required for the screening process to take place. They will comprise the target and a suitable buffer. A suitable buffer will be one in which all of the desired components of the biological system are active and will therefore depend upon the requirements of each specific reaction system. Buffers suitable for biological and/or chemical reactions are known in the art and recipes provided in various laboratory texts, such as (Sambrook and Russell, 2001).

Other components of the system will comprise those necessary for assaying the activity of the target. These may for example comprise substrate(s) and cofactor(s) for a reaction catalysed by the target, and ligand(s) bound by the target. They may also comprise other catalysts (including enzymes), substrates and cofactors for reactions coupled to the activity of the target which allow for the activity of the target to be detected.

(B) Screening Procedures

To screen compounds which bind to or modulate the activity of a target, the target is compartmentalised in microcapsules together with one or more compounds or compound-coated microbeads. Advantageously each microcapsule contains only a single sort of compound, but many copies thereof. Advantageously each microbead is coated with only a single sort of compound, but many copies thereof. Advantageously the compounds are connected to the microbeads via a cleavable linker, allowing them to be released from the microbeads in the compartments. Advantageously, each microcapsule or microbead is optically tagged to allow identification of the compounds contained within the microcapsule of attached to the microbead.

(i) Screening for Binding

Compounds can be screened directly for binding to a target. In this embodiment, if the compound is attached to a microbead and has affinity for the target it will be bound by the target. At the end of the reaction, all of the microcapsules are combined, and all microbeads pooled together in one environment. Microbeads carrying compounds exhibiting the desired binding can be selected by affinity purification using a molecule that specifically binds to, or reacts specifically with, the target.

In an alternative embodiment, the target can be attached to microbeads by a variety of means familiar to those skilled in the art (see for example (Hermanson, 1996)). The compounds to be screened contain a common feature—a tag. The compounds are released from the microbeads and if the compound has affinity for the target, it will bind to it. At the end of the reaction, all of the microcapsules are combined, and all microbeads pooled together in one environment. Microbeads carrying compounds exhibiting the desired binding can be selected by affinity purification using a molecule that specifically binds to, or reacts specifically with, the "tag".

In an alternative embodiment, microbeads may be screened on the basis that the compound, which binds to the target, merely hides the ligand from, for example, further binding partners. In this eventuality, the microbead, rather than being retained during an affinity purification step, may be selectively eluted whilst other microbeads are bound.

Sorting by affinity is dependent on the presence of two members of a binding pair in such conditions that binding may occur. Any binding pair may be used for this purpose. As used herein, the term binding pair refers to any pair of molecules capable of binding to one another. Examples of binding pairs that may be used in the present invention include an antigen and an antibody or fragment thereof capable of binding the antigen, the biotin-avidin/streptavidin pair (Savage et al., 1994), a calcium-dependent binding polypeptide and ligand thereof (e.g. calmodulin and a calmodulin-binding peptide (Montigiani et al., 1996; Stofko et al., 1992), pairs of polypeptides which assemble to form a leucine zipper (Tripet et al., 1996), histidines (typically hexahistidine peptides) and chelated $Cu^{2+}$, $Zn^{2+}$ and $Ni^{2+}$, (e.g. Ni-NTA; (Hochuli et al., 1987)), RNA-binding and DNA-binding proteins (Klug, 1995) including those containing zinc-finger motifs (Klug and Schwabe, 1995) and DNA methyltransferases (Anderson, 1993), and their nucleic acid binding sites.

In an alternative embodiment, compounds can be screened for binding to a target using a change in the optical properties of the microcapsule or the microbead.

The change in optical properties of the microcapsule or the microbead after binding of the compound to the target may be induced in a variety of ways, including:
(1) the compound itself may have distinctive optical properties, for example, it is fluorescent
(2) the optical properties of the compound may be modified on binding to the target, for example, the fluorescence of the compound is quenched or enhanced on binding (Voss, 1993; Masui and Kuramitsu, 1998).
(3) the optical properties of the target may be modified on binding of the compound, for example, the fluorescence of the target is quenched or enhanced on binding (Guixe et al., 1998; Qi and Grabowski, 1998)
(4) the optical properties of both target and compound are modified on binding, for example, there can be a fluorescence resonance energy transfer (FRET) from target to compound (or vice versa) resulting in emission at the "acceptor" emission wavelength when excitation is at the "donor" absorption wavelength (Heim & Tsien, 1996; Mahajan et al., 1998; Miyawaki et al., 1997).

The invention provides a method wherein a compound with the desired activity induces a change in the optical properties of the microcapsule, which enables the microcapsule containing the compound and the microbeads contained therein to be identified, and optionally, sorted.

In an alternative embodiment, the invention provides a method wherein microbeads are analysed following pooling of the microcapsules into one or more common compartments. In this embodiment, a compound having the desired activity modifies the optical properties of the microbead which carried it (and which resides in the same microcapsule) to allow it to be identified, and optionally, sorted.

In this embodiment, it is not necessary for binding of the compound to the target to directly induce a change in optical properties.

In this embodiment, if the compound attached to the microbead has affinity for the target it will be bound by the target. At the end of the reaction, all of the microcapsules are combined, and all microbeads pooled together in one environment. Microbeads carrying compounds exhibiting the desired binding can be identified by adding reagents that specifically bind to, or react specifically with, the target and thereby induce a change in the optical properties of the microbeads allowing their identification. For example, a fluorescently-labelled anti-target antibody can be used, or an anti-target antibody followed by a second fluorescently labelled antibody which binds the first.

In an alternative embodiment, the target can be attached to the microbeads by a variety of means familiar to those skilled in the art (see for example (Hermanson, 1996)). The compounds to be screened contain a common feature—a tag. The compounds are released from the microbeads and if the compound has affinity for the target, it will bind to it. At the end of the reaction, all of the microcapsules are combined, and all microbeads pooled together in one environment. Microbeads carrying compounds exhibiting the desired binding can be identified by adding reagents that specifically bind to, or react specifically with, the "tag" and thereby induce a change in the optical properties of the microbeads allowing their identification. For example, a fluorescently-labelled anti-"tag" antibody can be used, or an anti-"tag" antibody followed by a second fluorescently labelled antibody which binds the first.

In an alternative embodiment, microbeads may be identified on the basis that the gene product, which binds to the ligand, merely hides the ligand from, for example, further binding partners which would otherwise modify the optical properties of the microbeads. In this case microbeads with unmodified optical properties would be selected.

Fluorescence may be enhanced by the use of Tyramide Signal Amplification (TSA™) amplification to make the microbeads fluorescent (Sepp et al., 2002). This involves peroxidase (linked to another compound) binding to the microbeads and catalysing the conversion of fluorescein-tyramine in to a free radical form which then reacts (locally) with the microbeads. Methods for performing TSA are known in the art, and kits are available commercially from NEN.

TSA may be configured such that it results in a direct increase in the fluorescence of the microbeads, or such that a ligand is attached to the microbeads which is bound by a second fluorescent molecule, or a sequence of molecules, one or more of which is fluorescent.

(ii) Screening for Regulation of Binding

In an alternative embodiment, the invention can be used to screen compounds which act to regulate a biochemical process. If the compound activates a binding activity of a target, a ligand for the target which is activated can be attached to microbeads by a variety of means familiar to those skilled in the art (see for example (Hermanson, 1996)). At the end of the reaction, all of the microcapsules are combined, and all microbeads pooled together in one environment. Microbeads carrying compounds exhibiting the desired binding can be selected by affinity purification using a molecule that specifically binds to, or reacts specifically with, the target.

In an alternative embodiment, microbeads may be screened on the basis that the compound inhibits the binding activity of a target. In this eventuality, the microbead, rather than being retained during an affinity purification step, may be selectively eluted whilst other microbeads are bound.

In an alternative embodiment, compounds can be screened for the ability to modulates a binding activity of a target using a change in the optical properties of the microcapsule or the microbead.

The change in optical properties of the microcapsule or the microbead after binding of the target to its ligand may be induced in a variety of ways, including:
(1) the ligand itself may have distinctive optical properties, for example, it is fluorescent
(2) the optical properties of the ligand may be modified on binding to the target, for example, the fluorescence of the ligand is quenched or enhanced on binding (Voss, 1993; Masui and Kuramitsu, 1998).
(3) the optical properties of the target may be modified on binding of the ligand, for example, the fluorescence of the target is quenched or enhanced on binding (Guixe et al., 1998; Qi and Grabowski, 1998)
(4) the optical properties of both target and ligand are modified on binding, for example, there can be a fluorescence resonance energy transfer (FRET) from target to ligand (or vice versa) resulting in emission at the "acceptor" emission wavelength when excitation is at the "donor" absorption wavelength (Heim & Tsien, 1996; Mahajan et al., 1998; Miyawaki et al., 1997).

The invention provides a method wherein a compound with the desired activity induces a change in the optical properties of the microcapsule, which enables the microcapsule containing the compound and the microbeads contained therein to be identified, and optionally, sorted.

In an alternative embodiment, the invention provides a method wherein microbeads are analysed following pooling of the microcapsules into one or more common compartments. In this embodiment, a compound having the desired activity modifies the optical properties of the microbead which carried it (and which resides in the same microcapsule) to allow it to be identified, and optionally, sorted.

In this embodiment, it is not necessary for binding of the target to the ligand to directly induce a change in optical properties.

In this embodiment, if a ligand attached to the microbead has affinity for the target it will be bound by the target. At the end of the reaction, all of the microcapsules are combined, and all microbeads pooled together in one environment. Microbeads carrying compounds which modulate the binding activity can be identified by adding reagents that specifically bind to, or react specifically with, the target and thereby induce a change in the optical properties of the microbeads allowing their identification. For example, a fluorescently-labelled anti-target antibody can be used, or an anti-target antibody followed by a second fluorescently labelled antibody which binds the first.

In an alternative embodiment, the target can be attached to the microbeads by a variety of means familiar to those skilled in the art (see for example (Hermanson, 1996)). The ligand to be screened contains a feature—a tag. At the end of the reaction, all of the microcapsules are combined, and all microbeads pooled together in one environment. Microbeads carrying compounds which modulate binding can be identified by adding reagents that specifically bind to, or react specifically with, the "tag" and thereby induce a change in the optical properties of the microbeads allowing their identification. For example, a fluorescently-labelled anti-"tag" antibody can be used, or an anti-"tag" antibody followed by a second fluorescently labelled antibody which binds the first.

Fluorescence may be enhanced by the use of Tyramide Signal Amplification (TSA™) amplification to make the microbeads fluorescent (Sepp et al., 2002), as above.

(iii) Screening for Regulation of Catalysis

In an alternative embodiment, the invention provides a method wherein a compound with the desired activity induces a change in the optical properties of the microcapsule, which enables the microcapsule containing the compound and, optionally, the microbeads contained therein to be identified, and optionally, sorted. The optical properties of microcapsules can be modified by either:
   (a) the substrate and product of the regulated reaction having different optical properties (many fluorogenic enzyme substrates are available commercially, see for example (Haugland, 1996) including substrates for glycosidases, phosphatases, peptidases and proteases, or
   (b) the presence of reagents which specifically bind to, or react with, the product (or substrate) of the regulated reaction in the microcapsule and which thereby induce a change in the optical properties of the microcapsules allowing their identification.

A wide range of assays for screening libraries of compounds for those which modulate the activity of a target are based on detecting changes in optical properties and can be used to screen compounds according to this invention. Such assays are well known to those skilled in the art (see for example Haugland, 1996).

Alternatively, selection may be performed indirectly by coupling a first reaction to subsequent reactions that takes place in the same microcapsule. There are two general ways in which this may be performed. First, the product of the first reaction could be reacted with, or bound by, a molecule which does not react with the substrate(s) of the first reaction. A second, coupled reaction will only proceed in the presence of the product of the first reaction. A regulatory compound can then be identified by the properties of the product or substrate of the second reaction.

Alternatively, the product of the reaction being selected may be the substrate or cofactor for a second enzyme-catalysed reaction. The enzyme to catalyse the second reaction can be incorporated in the reaction mixture prior to microencapsulation. Only when the first reaction proceeds will the coupled enzyme generate an identifiable product.

This concept of coupling can be elaborated to incorporate multiple enzymes, each using as a substrate the product of the previous reaction. This allows for selection of regulators of enzymes that will not react with an immobilised substrate. It can also be designed to give increased sensitivity by signal amplification if a product of one reaction is a catalyst or a cofactor for a second reaction or series of reactions leading to a selectable product (for example, see (Johannsson, 1991; Johannsson and Bates, 1988). Furthermore an enzyme cascade system can be based on the production of an activator for an enzyme or the destruction of an enzyme inhibitor (see (Mize et al., 1989)). Coupling also has the advantage that a common screening system can be used for a whole group of enzymes which generate the same product and allows for the selection of regulation of complicated multi-step chemical transformations and pathways.

In an alternative embodiment, if the target is itself an enzyme, or regulates a biochemical process which is enzymatic, the microbead in each microcapsule may be coated with the substrate for the enzymatic reaction. The regulatory compound will determine the extent to which the substrate is converted into the product. At the end of the reaction the microbead is physically linked to the product of the catalysed reaction. When the microcapsules are combined and the reactants pooled, microbeads which were coated with activator compounds can be identified by any property specific to the product. If an inhibitor is desired, selection can be for a chemical property specific to the substrate of the regulated reaction.

It may also be desirable, in some cases, for the substrate not to be attached to the microbead. In this case the substrate would contain an inactive "tag" that requires a further step to activate it such as photoactivation (e.g. of a "caged" biotin analogue, (Pirrung and Huang, 1996; Sundberg et al., 1995)). After convertion of the substrate to product the "tag" is activated and the "tagged" substrate and/or product bound by a tag-binding molecule (e.g. avidin or streptavidin) attached to the microbead. The ratio of substrate to product attached to the nucleic acid via the "tag" will therefore reflect the ratio of the substrate and product in solution. A substrate tagged with caged biotin has been used to select for genes encoding enzymes with phosphotriesterase activity using a procedure based on compartmentalisation in microcapsules (Griffiths and Tawfik, 2003). The phosphotriesterase substrate was hydrolysed in solution in microcapsules containing active enzyme molecules, and after the reaction was completed, the caging group was released by irradiation to allow the product to bind, via the biotin moiety, to microbeads to which the gene encoding the enzyme was attached.

After the microbeads and the contents of the microcapsules are combined, those microbeads coated with regulators can be selected by affinity purification using a molecule (e.g. an antibody) that binds specifically to the product or substrate as appropriate.

In an alternative embodiment, the invention provides a method wherein the microbeads are analysed following pooling of the microcapsules into one or more common compartments. Microbeads coated with regulator compounds can be identified using changes in optical properties of the microbeads. The optical properties of microbeads with product (or substrate) attached can be modified by either:
   (1) the product-microbead complex having characteristic optical properties not found in the substrate-microbead complex, due to, for example;
      (a) the substrate and product having different optical properties (many fluorogenic enzyme substrates are available commercially (see for example Haugland, 1996) including substrates for glycosidases, phosphatases, peptidases and proteases, or
      (b) the substrate and product having similar optical properties, but only the product, and not the substrate binds to, or reacts with, the microbead;
   (2) adding reagents which specifically bind to, or react with, the product (or substrate) and which thereby induce a change in the optical properties of the microbeads allowing their identification (these reagents can be added before or after breaking the microcapsules and pooling the microbeads). The reagents;
      (a) bind specifically to, or react specifically with, the product, and not the substrate, (or vice versa) if both substrate and product are attached to the microbeads, or
      (b) optionally bind both substrate and product if only the product, and not the substrate binds to, or reacts with, the microbeads (or vice versa).

In this scenario, the substrate (or one of the substrates) can be present in each microcapsule unlinked to the microbead, but has a molecular "tag" (for example biotin, DIG or DNP or a fluorescent group). When the regulated enzyme converts the substrate to product, the product retains the "tag" and is then captured in the microcapsule by the product-specific antibody. When all reactions are stopped and the microcapsules are combined, these microbeads will be "tagged" and may already have changed optical properties, for example, if the "tag" was a fluorescent group. Alternatively, a change in optical properties of "tagged" microbeads can be induced by adding a fluorescently labelled ligand which binds the "tag" (for example fluorescently-labelled avidin/streptavidin, an anti-"tag" antibody which is fluorescent, or a non-fluorescent anti-"tag" antibody which can be detected by a second fluorescently-labelled antibody).

(iv) Screening for Compound Specificity/Selectivity

Compounds with specificity or selectivity for certain targets and not others can be specifically identified by carrying out a positive screen for regulation of a reaction using one substrate and a negative screen for regulation of a reaction with another substrate. For example, two substrates, specific for two different target enzymes, are each labelled with different fluorogenic moieties. Each target enzymes catalyse the generation of a product with a different fluorescence spectrum resulting in different optical properties of the microcapsules depending on the specificity of the compound for two targets.

(v) Screening Using Cells

In the current drug discovery paradigm, validated recombinant targets form the basis of in vitro high-throughput screening (HTS) assays. Isolated proteins cannot, however, be regarded as representative of complex biological systems; hence, cell-based systems can provide greater confidence in compound activity in an intact biological system. A wide range of cell-based assays for drug leads are known to those skilled in the art. Cells can be compartmentalised in microcapsules, such as the aqueous microdroplets of a water-in-oil emulsion (Ghadessy, 2001). The effect of a compound(s) on a target can be determined by compartmentalising a cell (or cells) in a microcapsule together with a compound(s) and using an appropriate cell-based assay to identify those compartments containing compounds with the desired effect on the cell(s). The use of water-in-fluorocarbon emulsions may be particularly advantageous: the high gas dissolving capacity of fluorocarbons can support the exchange of respiratory gases and has been reported to be beneficial to cell culture systems (Lowe, 2002).

(vi) Flow Cytometry

In a preferred embodiment of the invention the microcapsules or microbeads will be analysed and, optionally, sorted by flow cytometry. Many formats of microcapsule can be analysed and, optionally, sorted directly using flow cytometry. Some formats of microcapsule may require that the microcapsules be further processed before analysis or sorting. For example, water-in-oil emulsions can be converted into water-in-oil-in-water double emulsions to facilitate analysis by flow cytometry (Bernath et al., 2004). Multiple emulsions are prepared by the re-emulsification of a simple primary water-in-oil (or oil-in-water) emulsion to provide water-in-oil-in-water (or oil-in-water-in-oil) emulsions (Davis and Walker, 1987).

Highly monodisperse microcapsules can be produced using microfluidic techniques. For example, water-in-oil emulsions with less than 3% polydispersity can be generated by droplet break off in a co-flowing steam of oil (Umbanhowar, 2000). Microfluidic systems can also be used for laminar-flow of aqueous microdroplets dispersed in a stream of oil in microfluidic channels (Thorsen, 2001). This allows the construction of microfluidic devices for flow analysis and, optionally, flow sorting of microdroplets (Fu, 2002).

A variety of optical properties can be used for analysis and to trigger sorting, including light scattering (Kerker, 1983) and fluorescence polarisation (Rolland et al., 1985). In a highly preferred embodiment the difference in optical properties of the microcapsules or microbeads will be a difference in fluorescence and, if required, the microcapsules or microbeads will be sorted using a fluorescence activated cell sorter (Norman, 1980; Mackenzie and Pinder, 1986), or similar device. Flow cytometry has a series of advantages:

(1) commercially available fluorescence activated cell sorting equipment from established manufacturers (e.g. Becton-Dickinson, Coulter, Cytomation) allows the analysis and sorting at up to 100,000 microcapsules or microbeads $s^{-1}$.

(2) the fluorescence signal from each microcapsule or microbead corresponds tightly to the number of fluorescent molecules present. As little as few hundred fluorescent molecules per microcapsules or microbeads can be quantitatively detected;

(3) the wide dynamic range of the fluorescence detectors (typically 4 log units) allows easy setting of the stringency of the sorting procedure, thus allowing the recovery of the optimal number microcapsules or microbeads from the starting pool (the gates can be set to separate microcapsules or microbeads with small differences in fluorescence or to only separate out microcapsules or microbeads with large differences in fluorescence, dependant on the selection being performed);

(4) commercially available fluorescence-activated cell sorting equipment can perform simultaneous excitation and detection at multiple wavelengths (Shapiro, 1995). allowing positive and negative selections to be performed simultaneously by monitoring the labelling of the microcapsules or microbeads with two to thirteen (or more) fluorescent markers, for example, if substrates for two alternative targets are labelled with different fluorescent tags the microcapsules or microbeads can labelled with different fluorophores dependent on the target regulated.

If, the microcapsules or microbeads are optically tagged, flow cytometry can also be used to identify the compound or compounds in the microcapsule or coated on the microbeads (see below). Optical tagging can also be used to identify the concentration of the compound in the microcapsule (if more than one concentration is used in a single experiment) or the number of compound molecules coated on a microbead (if more than one coating density is used in a single experiment). Furthermore, optical tagging can be used to identify the target in a microcapsule (if more than one target is used in a single experiment). This analysis can be performed simultaneously with measuring activity, after sorting of microcapsules containing microbeads, or after sorting of the microbeads.

(vii) Microcapsule Identification and Sorting

The invention provides for the identification and, optionally, the sorting of intact microcapsules where this is enabled by the sorting techniques being employed. Microcapsules may be identified and, optionally, sorted as such when the change induced by the desired compound either occurs or manifests itself at the surface of the microcapsule or is detectable from outside the microcapsule. The change may be caused by the direct action of the compound, or indirect, in which a series of reactions, one or more of which involve the compound having the desired activity leads to the change. For example, where the microcapsule is a membranous microcapsule, the microcapsule may be so configured that a component or components of the biochemical system comprising the target are displayed at its surface and thus accessible to reagents which can detect changes in the biochemical system regulated by the compound on the microbead within the microcapsule.

In a preferred aspect of the invention, however, microcapsule identification and, optionally, sorting relies on a change in the optical properties of the microcapsule, for example absorption or emission characteristics thereof, for example alteration in the optical properties of the microcapsule resulting from a reaction leading to changes in absorbance, luminescence, phosphorescence or fluorescence associated with the microcapsule. All such properties are included in the term "optical". In such a case, microcapsules can be identified and, optionally, sorted by luminescence, fluorescence or phosphorescence activated sorting. In a highly preferred embodiment, flow cytometry is employed to analyse and, optionally, sort microcapsules containing compounds having a desired activity which result in the production of a fluorescent molecule in the microcapsule.

In an alternative embodiment, a change in microcapsule fluorescence, when identified, is used to trigger the modification of the microbead within the compartment. In a preferred aspect of the invention, microcapsule identification relies on a change in the optical properties of the microcapsule resulting from a reaction leading to luminescence, phosphorescence or fluorescence within the microcapsule. Modification of the microbead within the microcapsules would be triggered by identification of luminescence, phosphorescence or fluorescence. For example, identification of luminescence, phosphorescence or fluorescence can trigger bombardment of the compartment with photons (or other particles or waves) which leads to modification of the microbead or molecules attached to it. A similar procedure has been described previously for the rapid sorting of cells (Keij et al., 1994). Modification of the microbead may result, for example, from coupling a molecular "tag", caged by a photolabile protecting group to the microbeads: bombardment with photons of an appropriate wavelength leads to the removal of the cage. Afterwards, all microcapsules are combined and the microbeads pooled together in one environment. Microbeads coated with compounds exhibiting the desired activity can be selected by affinity purification using a molecule that specifically binds to, or reacts specifically with, the "tag".

(C) Compound Libraries

Libraries of compounds can be obtained from a variety of commercial sources. The compounds in the library can be made by a variety of means well known to those skilled in the art. Optionally, compound libraries can be made by combinatorial synthesis using spatially resolved parallel synthesis or using split synthesis, optionally to generate one-bead-one-compound libraries. The compounds can, optionally, be synthesised on beads. These beads can be compartmentalised in microcapsules directly or the compounds released before compartmentalisation.

Advantageously, only a single type of compound, but multiple copies thereof is present in each microcapsule.

The compounds can, optionally, be connected to microbeads either covalently or non-covalently by a variety of means that will be familiar to those skilled in the art (see, for example, (Hermanson, 1996)).

Microbeads are available with a variety of surface chemistries from hydrophobic surfaces (e.g. plain polystyrene), to very hydrophilic surfaces imparted by a wide variety of functional surface groups: aldehyde, aliphatic amine, amide, aromatic amine, carboxylic acid, chloromethyl, epoxy, hydrazide, hydroxyl, sulfonate and tosyl. The functional groups permit a wide range of covalent coupling reactions, well known to those skilled in the art, for stable or reversible attachment of compounds to the microbead surface.

Advantageously, the compounds are attached to the microbeads via a cleavable linker. A variety of such linkers are familiar to those skilled in the art (see for example (Gordon and Balasubramanian, 1999)), including for example, linkers which can be cleaved photochemically and reversible covalent bonds which can be controlled by changing the pH (e.g. imines and acylhydrazones), by adjusting the oxido-reductive properties (e.g. disulphides), or using an external catalyst (e.g. cross-metathesis and transamidation).

Advantageously, only a single type of compound, but multiple copies thereof is attached to each bead.

(D) Identification of Compounds

The compounds in microcapsules or on microbeads can be identified in a variety of ways. If the identified microcapsules are sorted (e.g. by using a fluorescence activated cell sorter—FACS) the compounds can be identified by direct analysis, for example by mass-spectroscopy. If the compounds remain attached to beads isolated as a result of selection (for example by affinity purification) or sorting (for example using a FACS) they can also be identified by direct analysis, for example by mass-spectroscopy. The microcapsules or beads can also be tagged by a variety of means well known to those skilled in the art and the tag used to identify the compound attached to the beads (Czarnik, 1997). Chemical, spectrometric, electronic, and physical methods to encode the compounds may all be used. In a preferred embodiment microcapsules or beads have different optical properties and are thereby optically encoded. In a preferred embodiment encoding is based on microcapsules or beads having different fluorescence properties. In a highly preferred embodiment the microcapsules or beads are encoded using fluorescent quantum dots present at different concentrations in the microcapsule or bead (Han, 2001). Microcapsules flowing in an ordered sequence in a microfluidic channel can also be encoded (wholly or partially) by their sequence in the stream of microcapsules (positional encoding).

Advantageously, each compounds is present in different microcapsules at different concentrations (typically at concentrations varying from mM to nM) allowing the generation of a dose-response curve. This would, for example, allow the determination of the inhibition constant ($K_i$) of an inhibitory compound. The concentration of the compounds in the microcapsules can be determined by, for example, optical encoding or positional encoding of the microcapsules or microbeads as above.

(E) Identification of Targets

Advantageously, multiple different targets can be compartmentalised in microcapsules such that each microcapsule contains multiple copies of the same target. For example, multiple protein kinases, or multiple polymorphic variants of a single target, can be compartmentalised to allow the specificity of compounds to be determined. The identity of the target in a microcapsule can be determined by, for example, optical encoding or positional encoding of the microcapsules or microbeads as above.

EXAMPLES

Example 1

Screening for Inhibitors of the Enzyme Protein Tyrosine Phosphatase 1B (PTP1B)

PTP1B is a negative regulator of insulin and leptin signal transduction. Resistance to insulin and leptin are hallmarks of type 2 diabetes mellitus and obesity and hence PTP1B is an attractive drug target for diabetes and obesity therapy (Johnson et al., 2002). Two water-in-oil emulsions are made as follows.

A solution of 1% (w/v) Span 60 and 1% (w/v) cholesterol in decane (all from Sigma Aldrich) is prepared by dissolving 80 mg of Span 60 and 80 mg of cholesterol into 7.84 ml of decane. The decane is heated to 45° C. to allow complete solubilization of the surfactant and cholesterol. The surfactant/decane solution is divided over batches of 200 µl and placed in a block-heater at 37° C.

A hand-extruding device (Mini extruder, Avanti Polar Lipids Inc, Alabaster, Ala., USA) is assembled according to the manufacturer's instructions. For extrusion, a single 19 mm Track-Etch polycarbonate filter with average pore size of 14 µm (Whatman Nuclepore, Whatman, Maidstone, UK) is fitted inside the mini extruder. Two gas-tight 1 ml Hamilton syringes (Gastight #1001, Hamilton Co, Reno, Nev., USA) are used for extrusion. The extruder was pre-rinsed with 3×1 ml of decane by loading one of the Hamilton syringes with 1 ml of decane, placing the syringe at one and of the mini extruder and extruding it through the filters into the empty Hamilton syringe on the other side of the extruder.

The first emulsion is made by loading 50 µl of 100 µM compound 2 (FIG. 1), which has a bis-difluoromethylene phosphonate and is a known PTP1B inhibitor (Johnson et al., 2002), the target enzyme (human recombinant PTP1B, residues 1-322; Biomol Research Laboratories, Inc.) at 5 mU/ml, the fluorogenic PTP1B substrate 6,8-difluoro-4-methylumbelliferyl phosphate (DiFMUP) (Molecular Probes), and 100 µM Texas Red (Sigma; excitation/emmission maxima 595/615 nm; red fluorescence) in a buffer compatible with PTP1B activity (25 mM HEPES, pH 7.4, 125 mM NaCl, 10% glycerol, 1 mM EDTA) (Doman et al., 2002) into one of the Hamilton syringes, and 200 µl of the pre-heated decane/surfactant mix into the other Hamilton syringe. The syringes are fitted into the openings on both sides of the filter holder of the extruder. The compound mix is forced through the filter holder into the alternate syringe containing the decane/surfactant mix and directly forced back into the original syringe to complete one round of extrusion. In total, 7.5 rounds of extrusion are completed. The filled syringe is removed from the extruder and emptied into a 1.7 ml Axygen tube (# MCT-175-C, Axygen Scientific, Inc., Union City, Calif., USA).

A second water-in-oil emulsion is made identical to the emulsion above but containing 100 µM hydrocinnamic acid (Aldrich), a compound that is not a PTP1B inhibitor, in place of compound 2, and 100 µM calcein (Sigma; excitation/emmission maxima 470/509 nm; green fluorescence) in place of Texas Red.

The two emulsions are mixed by vortexing in ratios varying from 1:1000 to 1:1 (compound 2 emulsion: hydrocinnamic acid emulsion) and incubated at 37° C. for 30 min Inhibitors reduce the amount of non-fluorescent substrate (DiFMUP) converted to the dephosphorylated product (DiFMU; excitation/emmission maxima 358/452 nm; blue fluorescence).

The water-in-oil emulsions are then converted into water-in-oil-in water double emulsions as follows. The extruder (see above) is disassembled, cleaned extensively with soap and reversed-osmosis water, and re-assembled. A single 19 mm Track-Etch polycarbonate filter with an average pore size of 8 µm is fitted. The extruder is pre-rinsed with 3×1 ml phosphate-buffered saline solution (PBS). 750 µl of PBS containing 0.5% (w/v) Tween 80 (Sigma Aldrich) is loaded into a 1 ml gas-tight Hamilton syringe and fitted into the extruder. 250 µl of the water-in-oil emulsion is loaded into the alternate 1 ml Hamilton syringe and fitted into the extruder. The emulsion is forced through the filter into the alternate syringe containing the PBS/0.5% Tween 80 and immediately forced back into the original syringe to complete one cycle of extrusion. In total, 4.5 cycles of extrusion are performed. The filled syringe is removed from the extruder and emptied into a 1.7 ml Axygen tube. The water-in-oil-in-water double emulsions formed are placed on ice.

The double emulsions are then analysed by multi-colour flow cytometery using a MoFlo (Cytomation) flow cytometer. Predominantly, microcapsules exhibiting green fluorescence (and containing hydrocinnamic acid) also show blue fluorescence due to dephosphorylation of DiFMUP by PTP1B. Predominantly, microcapsules exhibiting red fluorescence (and containing compound 2) also show little or no blue fluorescence due to inhibition of PTP1B.

Example 2

Two aqueous mixtures are made on ice (to prevent reaction). The first mixture contains 100 µM compound 2 (FIG. 1), which has a bis-difluoromethylene phosphonate and is a known PTP1B inhibitor (Johnson et al., 2002), the target enzyme (human recombinant PTP1B, residues 1-322; Biomol Research Laboratories, Inc.) at 5 mU/ml, the fluorogenic PTP1B substrate 6,8-difluoro-4-methylumbelliferyl phosphate (DiFMUP) (Molecular Probes), and 100 µM Texas Red (Sigma; excitation/emmission maxima 595/615 nm; red fluorescence) in a buffer compatible with PTP1B activity (25 mM HEPES, pH 7.4, 125 mM NaCl, 10% glycerol, 1 mM EDTA) (Doman et al., 2002). A second mixture is created identical to the above but containing 100 µM hydrocinnamic acid (Aldrich), a compound that is not a PTP1B inhibitor, in place of compound 2, and 100 µM calcein (Sigma; excitation/emmission maxima 470/509 nm; green fluorescence) in place of Texas Red.

50 µl of each of the compound mixtures is added sequentially to a solution of 1% (w/v) Span 60 and 1% (w/v) cholesterol in decane, made and held at 37° C. as example 1, whilst homogenising at 25,000 r.p.m. using an Ultra-Turrax T8 Homogenizer (IKA) with a 5 mm dispersing tool. Homogenisation is continued for 3 minutes after the addition of the second aliquot. The coarse emulsion produced is then extruded as in example 1 to create a fine water-in-oil emulsion and incubated at 37° C. for 30 min. Inhibitors reduce the amount of non-fluorescent substrate (DiFMUP) converted to the dephosphorylated product (DiFMU; excitation/emmission maxima 358/452 nm; blue fluorescence). The water-in-oil emulsion is then converted into a water-in-oil-in water double emulsion and analysed by multi-colour flow cytometery as in example 1. Predominantly, microcapsules exhibiting green fluorescence (and containing hydrocinnamic acid) also show blue fluorescence due to dephosphorylation of DiFMUP by PTP1B. Predominantly, microcapsules exhibiting red fluorescence (and containing compound 2) also show little or no blue fluorescence due to inhibition of PTP1B.

Example 3

Screening of PTP1B Inhibitors from a Compound Library 100 water-in-oil emulsions are made on ice (to prevent reaction) as in example 1. The first emulsion is made by dispersing a mixture of 100 µM compound 2 (FIG. 1), which has a bis-difluoromethylene phosphonate and is a known PTP1B inhibitor (Johnson et al., 2002), the target enzyme (human recombinant PTP1B, residues 1-322; Biomol Research Laboratories, Inc.) at 5 mU/ml, the fluorogenic PTP1B substrate 6,8-difluoro-4-methylumbelliferyl phosphate (DiFMUP) (Molecular Probes), and a pre-defined ratio of Qdot™ Streptavidin Conjugates with emmission maxima at 585 nm, 655 nm and 705 nm (Quantum Dot Corporation, Hayward Calif.) in a buffer compatible with PTP1B activity (25 mM HEPES, pH 7.4, 125 mM NaCl, 10% glycerol, 1 mM EDTA) (Doman et al., 2002). The 99 other water-in-oil emulsions are identical to the above but each contain one of 99 carboxylic acids from the Carboxylic Acid Organic Building Block Library (Aldrich) in place of compound 2, and different ratios of Qdot™ Streptavidin Conjugates with emmission maxima at 585 nm, 655 nm and 705 nm. In all emulsions the concentration of the 705 nm Qdot™ Streptavidin Conjugates is 100 nM, and the concentrations of the 585 nm and 655 nm Qdot™ Streptavidin Conjugates is either 0, 11, 22, 33, 44, 55, 66, 77, 88 or 100 nM. Hence, there are 100 (10×10) permutations of Qdot™ Streptavidin Conjugate concentrations which allows the microcapsules containing each compound to have a unique fluorescence signature which is read by determining the fluorescence ratios of fluorescence at 705 nm, 585 nm and 655 nm.

The 100 emulsions are mixed in equal ratios by vortexing and the temperature raised to 25° C. for 30 min. Inhibitors reduce the amount of non-fluorescent substrate (DiFMUP) converted to the dephosphorylated product (DiFMU; excitation/emmission maxima 358/452 nm; blue fluorescence). The water-in-oil emulsion is then converted into a water-in-oil-in water double emulsion and analysed by multi-colour flow cytometry as in example 1n. Predominantly, all microcapsules exhibited blue fluorescence due to dephosphorylation of DiFMUP by PTP1B except those with the Qdot fluorescence signature of the microcapsules containing compound 2.

Example 4

Screening of PTP1B Inhibitors from a Compound Library 100 aqueous mixtures are made on ice (to prevent reaction). The first mixture contains 100 µM compound 2 (FIG. 1), which has a bis-difluoromethylene phosphonate and is a known PTP1B inhibitor (Johnson et al., 2002), the target enzyme (human recombinant PTP1B, residues 1-322; Biomol Research Laboratories, Inc.) at 5 mU/ml, the fluorogenic PTP1B substrate 6,8-difluoro-4-methylumbelliferyl phosphate (DiFMUP) (Molecular Probes), and a pre-defined ratio of Qdot™ Streptavidin Conjugates with emmission maxima at 585 nm, 655 nm and 705 nm (Quantum Dot Corporation, Hayward Calif.) in a buffer compatible with PTP1B activity (25 mM HEPES, pH 7.4, 125 mM NaCl, 10% glycerol, 1 mM EDTA) (Doman et al., 2002). The 99 other aqueous mixtures are identical to the above but each contain one of 99 carboxylic acids from the Carboxylic Acid Organic Building Block Library (Aldrich) in place of compound 2, and different ratios of Qdot™ Streptavidin Conjugates with emission maxima at 585 nm, 655 nm and 705 nm. In all mixtures the concentration of the 705 nm Qdot™ Streptavidin Conjugates is 100 nM, and the concentrations of the 585 nm and 655 nm Qdot™ Streptavidin Conjugates is either 0, 11, 22, 33, 44, 55, 66, 77, 88 or 100 nM. Hence, there are 100 (10×10) permutations of Qdot™ Streptavidin Conjugate concentrations which allows the microcapsules containing each compound to have a unique fluorescence signature which is read by determining the fluorescence ratio of fluorescence at 705 nm, 585 nm and 655 nm.

0.5 µl of each of the compound mixtures is added sequentially to a solution of 1% (w/v) Span 60 and 1% (w/v) cholesterol in decane, made and held at 37° C. as example 1, whilst homogenising at 25,000 r.p.m. using an Ultra-Turrax T8 Homogenizer (IKA) with a 5 mm dispersing tool. Homogenisation is continued for 3 minutes after the addition of the second aliquot. The coarse emulsion produced is then extruded as in example 1 to create a fine water-in-oil emulsion and incubated at 37° C. for 30 min. Inhibitors reduce the amount of non-fluorescent substrate (DiFMUP) converted to the dephosphorylated product (DiFMU; excitation/emmission maxima 358/452 nm; blue fluorescence). The water-in-oil emulsion is then converted into a water-in-oil-in water double emulsion and analysed by multi-colour flow cytometry as in example 1. Predominantly, all microcapsules exhibited blue fluorescence due to dephosphorylation of DiFMUP by PTP1B except those with the Qdot fluorescence signature of the microcapsules containing compound 2.

Example 5

Screening for PTP1B Inhibitors using Microcapsules in Microfluidic Systems

Microchannels are fabricated with rectangular cross-sections using rapid prototyping in poly(dimethylsiloxane) (PDMS) (McDonald and Whitesides, 2002) and rendered hydrophobic as (Song and Ismagilov, 2003). Syringe pumps were used to drive flows (Harvard Apparatus PHD 2000 Infusion pumps). For aqueous solutions, 50 µl Hamilton Gastight syringes (1700 series, TLL) with removeable needles of 27-gauge are used with 30-gauge Teflon tubing (Weico Wire and Cable). For the carrier fluid, 1 ml Hamilton Gastight syringes (1700 series, TLL) are used with 30-gauge Teflon needles with one hub from Hamilton (Song and Ismagilov, 2003). The carrier fluid is 9% (v/v) $C_6F_{11}C_2H_4OH$ in perfluorodecaline (PFD) (Song et al., 2003). All water-soluble reagents were dissolved in (25 mM HEPES, pH 7.4, 125 mM NaCl, 1 mM EDTA), a buffer compatible with PTP1B activity.

A solution of the target enzyme (human recombinant PTP1B, residues 1-322; Biomol Research Laboratories, Inc.) at 50 mU/ml and a solution of either a) 100 µM compound 2 (FIG. 1), which has a bis-difluoromethylene phosphonate and is a known PTP1B inhibitor (Johnson et al., 2002), or b) 100 µM hydrocinnamic acid (Aldrich), a compound that is not a PTP1B inhibitor are flowed in a microchannel as two laminar streams, with an inert centre stream (of 25 mM HEPES, pH 7.4, 125 mM NaCl, 1 mM EDTA) to separate them and prevent the enzyme and compound coming into contact prior to droplet microcapsule formation (Song et al., 2003). These three steams are continuously injected into a flow of water immiscible fluorocarbon carrier fluid (9% (v/v) $C_6F_{11}C_2H_4OH$ in PFD). Inlet channels for the aqueous solutions are 50 µm² wide and channel for PFD is 28 µm wide. A variety of PFD/water volumetric flow rates (in µl min$^{-1}$) can be used including 0.6:0.3, 1.0:0.6, 12.3:3.7, 10:6 and 20:6, resulting in flow rates of 10, 19, 190, 190 and 300 mm s$^{-1}$ respectively. Aqueous microcapsules which occupy the entire width of the channel are formed by drop-breakoff in the PFD stream (Song et al., 2003). Microcapsules containing either compound 2 or hydrocinnamic acid can be formed by switching between injection with syringes containing compound 2 and hydrocinnamic acid.

The channel immediately downstream of the point of droplet formation is winding with a peak to peak distance of 50 µm for a distance of 1 mm. This results in rapid mixing of the contents of the microcapsule by chaotic advection (Song et al., 2003). After this point the microcapsules are run for up to 1 min through a 60 cm long microchannel (to allow inhibitor binding). This microchannel is then merged with a 60×50 µm$^2$ microchannel containing aqueous microcapsules in (9% (v/v) $C_6F_{11}C_2H_4OH$ in PFD) formed as above. These larger microcapsules contain the fluorogenic PTP1B substrate 6,8-difluoro-4-methylumbelliferyl phosphate (DiFMUP) (Molecular Probes) in 25 mM HEPES, pH 7.4, 125 mM NaCl, 1 mM EDTA. After the junction between the microchannels the expanded main channel is 100×50 µm$^2$ and the microcapsules do not block the channel and can move at different speeds until a large microcapsule (containing DiFMUP) coalesces with a small microcapsule (containing PTP1B and the compound) (Song et al., 2003). The frequency of production of large and small microcapsules is equal such that each large microcapsule has a small microcapsule with which to fuse. The fused microcapsules are then run for up to 2 min through a 60 cm long microchannel. Fluorescence of the microcapsules due to production of DiFMU (excitation/emmission maxima 358/452 nm; blue fluorescence) is measured using an epifluorescence microscope. Predominantly, microcapsules exhibiting blue fluorescence are those containing hydrocinnamic acid whereas microcapsules containing compound 2 exhibit low fluorescence due to inhibition of PTP1B.

Example 6

Attachment of a Compound Library to Microbeads 5.5 µm diameter polystyrene microbeads that bear carboxylate functional groups on the surface are commercially available (Luminex Corporation) in an optically tagged form, as a result of incorporation of precise ratios of orange (585 nm), and red (>650 mm) fluorochromes (Fulton et al., 1997). A set of 100 such beads, each with a unique optical signature are modified with an excess of ethylenediamine and EDC (1-ethyl-3-(3-dimethylaminopropyl)carbodiimide hydrochloride (Pierce) as (Hermanson, 1996) to create primary amino groups on the surface. The photocleavable linker 4-(4-hydroxymethyl-2-methoxy-5-nitrophenoxy)butanoic acid (NovaBiochem) (Holmes and Jones, 1995) is then attached to the beads by forming an amide bond using EDC as above. 100 different carboxylic acids from the Carboxylic Acid Organic Building Block Library (Aldrich) are then coupled to the beads, by reacting with the linker alcohol to form a carboxylate ester, each of the 100 different optically tagged beads being coupled to a different carboxylic acid, and each bead being derivatised with ~10$^6$ molecules of carboxylic acid. Irradiation for 4 min on ice using a B100 AP 354 nm UV lamp (UVP) from a distance of ~5 cm results in release of the compounds from the beads as carboxylic acids.

Example 7

Screening for Inhibitors of the Enzyme Protein Tyrosine Phosphatase 1B (PTP1B) Using Compounds Attached to Microbeads PTP1B is a negative regulator of insulin and leptin signal transduction. Resistance to insulin and leptin are hallmarks of type 2 diabetes mellitus and obesity and hence PTP1B is an attractive drug target for diabetes and obesity therapy (Johnson et al., 2002). 5.5 µm diameter polystyrene microbeads that bear carboxylate functional groups on the surface are commercially available (Luminex Corporation) in an optically tagged form, as a result of incorporation of precise ratios of orange (585 nm), and red (>650 nm) fluorochromes (Fulton et al., 1997). First, the carboxylate functional groups on the microbeads are converted to primary amines using ethylenediamine and EDC as in example 6. A phosphopeptide substrate for PTP1B, the undecapeptide EGFR$_{988-998}$ (DADEpYLIPQQG; SEQ ID NO: 1) (Zhang et al., 1993), is then coupled to both sets of microbeads via the surface amino groups using EDC. This peptide is made by solid phase synthesis on Sieber Amide resin (9-Fmoc-amino-xanthen-3-yloxy-Merrifield resin) (Novabiochem) with orthogonal protection on the side chain carboxylate groups using carboxylate-O-allyl esters. A linker comprised of tetradecanedioic acid is coupled to the N-terminus and the peptide cleaved from the beads using 1% TFA to yield a peptide with a C-terminal amide The peptide is coupled to the beads (using EDC) via the linker to give ~10$^5$ peptides per bead. The remaining surface amino groups are then modified by attaching the photochemically cleavable linker 4-(4-hydroxymethyl-2-methoxy-5-nitrophenoxy)butanoic acid as in example 6. The protecting groups on the side chain carboxylates of the peptide are then removed using Pd(Ph$_3$)$_4$/CHCl$_3$/HOAc/N-methyl morpholine. A first set of microbeads is derivatised with 3-(4-difluorophosphonom-ethylphenyl)propanoic acid (compound 1, FIG. 1), a compound that is a known PTP1B inhibitor (Johnson et al., 2002). A second set of beads, with a distinct optical tag from the first set of beads, is derivatised with hydrocinnamic acid (Aldrich), a compound that is not a PTP1B inhibitor. In each case the compound is coupled by reacting with the linker alcohol to form a carboxylate ester as in example 6. Each microbead is derivatised with ~10$^6$ molecules (Fulton et al., 1997).

Figure 2:
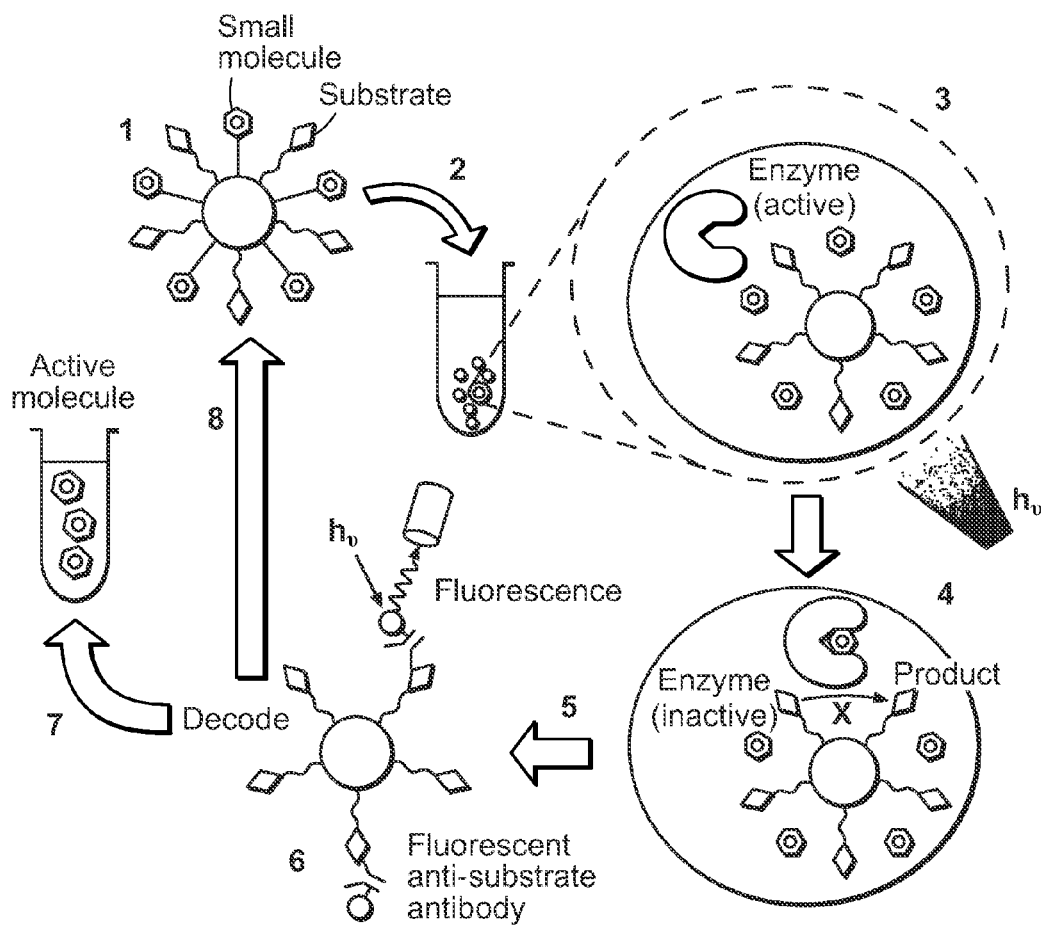
FIG. 2. Screening PTP1B inhibitors using microencapsulation. Polystyrene beads with surface carboxylate groups, died with orange or red fluorochromes (Fulton et al., 1997), are derivatised with a phosphopeptide PTP1B substrate, and either PTP1B inhibitors or non-inhibitory compounds attached via a cleavable linker (1). After mixing the beads, single beads and target enzyme (PTP1B) are colocalised in a microcompartment by forming a water-in-oil emulsion (2). The compound is released photochemically (3). Inhibitors reduce the amount of substrate converted to product (dephosphorylated peptide) (4). The enzyme reaction is stopped and the emulsion is broken (5). After labelling with green fluorescent anti-substrate antibodies, beads are analysed by 3-colour flow cytometry to simultaneously determine extent of inhibition and the compound on the beads (6). Ultimately, compound libraries will be coupled to optically tagged beads (see below) and rapidly decoded by flow cytometry (at up to 100,000 beads s-1). Hit compounds can be re-synthesised for further characterisation (7) or elaborated and rescreened in a process of synthetic evolution (8).

The microbeads are then screened using the method outlined in FIG. 2. The two sets of microbeads are mixed in ratios varying from 1:1000 to 1:1 (compound 1 beads: hydrocinnamic acid beads) and 10$^8$ total microbeads are mixed with the target enzyme (human recombinant PTP1B, residues 1-322; Biomol Research Laboratories, Inc.) at a concentration of 10 nM, on ice (to prevent reaction) in a buffer compatible with PTP1B activity (25 mM HEPES, pH 7.4, 125 mM NaCl, 10% glycerol, 1 mM EDTA) (Doman et al., 2002). Single beads and target enzyme (PTP1B) are then colocalised in microcapsules by forming a water-in-oil emulsion (also on ice). The concentration of beads is such that most microcapsules contain one or no beads. The compound is released photochemically (as in example 6) and the temperature raised to 25° C. Inhibitors reduce the amount of substrate converted to product (dephosphorylated peptide). The emulsion is cooled to 4° C. and broken as (Griffiths and Tawfik, 2003) into 100 µM vanadate to stop the reaction (Harder et al., 1994). After labelling with an anti-substrate (anti-phosphotyrosine) antibody labelled with the green (530 nm) fluorochrome fluorescein isothiocyanate (mouse monoclonal IgG$_{2b}$ PY20 (Santa Cruz) according to the manufacturer's instructions, beads are analysed by 3-colour flow cytometry using a FACScan (Becton-Dickinson), FACScalibur (Becton-Dickinson) or MoFlo (Cytomation) flow cytometers to simultaneously determine the extent of inhibition and the compound on the beads. Predominantly, dephosphorylation of the peptide is only observed on those microbeads which were coated with PTP1B inhibitors, and not on other microbeads.

Example 8

Screening of PTP1B Inhibitors from a Compound Library Attached to Microbeads

A set of 100 5.5 µm diameter polystyrene microbeads, bearing carboxylate functional groups on the surface and each with a unique optical signature (Luminex Corporation) as a result of incorporation of precise ratios of orange (585 nm), and red (>650 nm) fluorochromes (Fulton et al., 1997) are derivatised with a phosphopeptide substrate for PTP 1B, the undecapeptide EGFR$_{988-998}$ (DADEpYLIPQQG; SEQ ID NO: 1) (Zhang et al., 1993), and 100 different carboxylic acids, each attached via a photochemically cleavable linker, as in example 7. One of these carboxylic acids is 3-4-difluorophosphonomethylphenyl)propanoic acid (compound 1, FIG. 1), a compound that is a known PTP1B inhibitor (Johnson et al., 2002). The other 99 carboxylic acids are from the Carboxylic Acid Organic Building Block Library (Aldrich) as example 6. Equal numbers of each of the 100 bead sets are then mixed and screened as for example 7. Predominantly, dephosphorylation of the peptide is only observed on those microbeads which were coated with the PTP1B inhibitor 3-(4-difluorophosphonomethylphenyl)propanoic acid (compound 1, FIG. 1), and not on microbeads coated with other compounds.

Example 9

Compartmentalisation of Small Molecules in a Water-in-Fluorocarbon Emulsions

Figure 3:
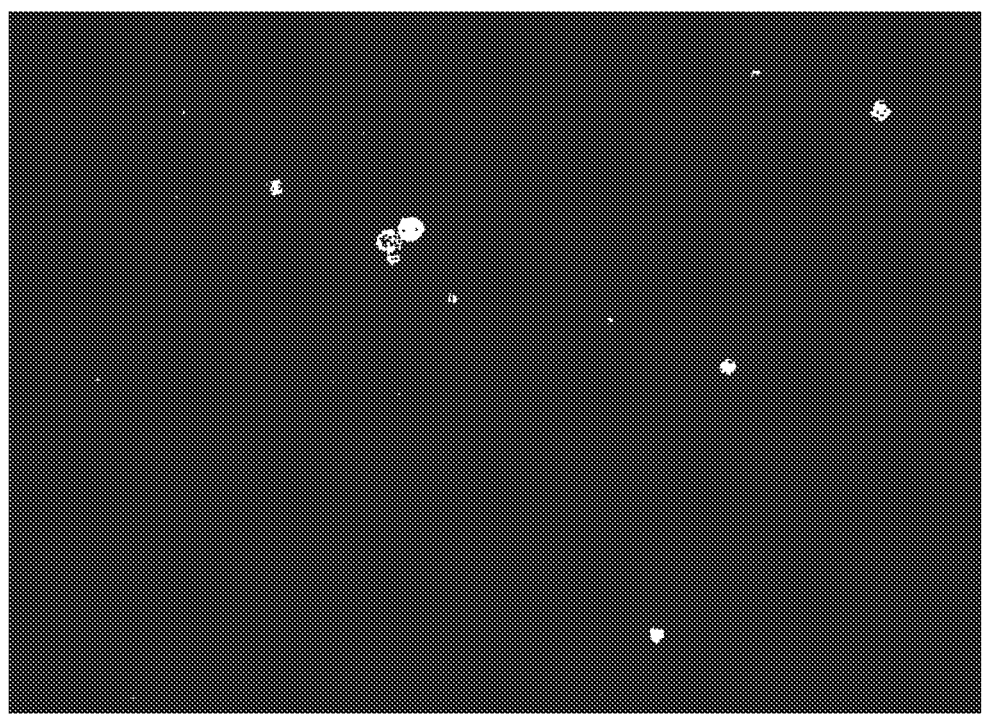
FIG. 3. Compartmentalisation of small molecules in water-in-fluorocarbon emulsions. Water-in-perfluorooctyl bromide emulsions were made containing texas red (1 mM) and calcein (1 mM) in the aqueous phase by homogenisation as described in example 9. The two emulsions were mixed by vortexing and imaged by epifluorescence microscopy after 24 hours. No exchange of texas-red (red fluorescence) and calcein (green fluorescence) between microdroplets could be observed.

Water-in-fluorocarbon emulsions containing 95% (v/v) perfluorooctyl bromide, 5% (v/v) phosphate buffered saline containing the molecule of interest in solution, and 2% (w/v) $C_8F_{17}C_{11}H_{22}OP(O)[N(CH_2CH_2)_2O]_2$ (F8H11DMP) as surfactant were formed essentially as (Sadder et al., 1996) by extrusion (15 times) through 14 µm filters (Osmonics) or by homogenising for 5 min at 25,000 r.p.m. using an Ultra-Turrax T8 Homogenizer (IKA) with a 5 mm dispersing tool. Emulsions were made containing a series of small fluorescent molecules dissolved in the aqueous phase at concentrations from 100 µm to 2 mM. These molecules, including calcein, texas red, fluorescein, coumarin 102, 7-hydroxy-coumarin-3-carboxylic acid and 7-diethylamino-4-methyl coumarin (coumarin 1), had molecular weights from 203 to 625 Da and Log P values—calculated using SRC's Log-Kow/KowWin Program (Meylan and Howard, 1995)—ranging from −0.49 to 4.09. Emulsions containing different coloured fluorochromes were mixed by vortexing. Compartmentalisation was observed by epifluorescence microscopy of the mixed emulsions. No exchange between compartments was observed 24 hours after mixing (see FIG. 3).

REFERENCES

Adang, A. E., and Hermkens, P. H. (2001). The contribution of combinatorial chemistry to lead generation: an interim analysis. Curr Med Chem 8, 985-998.
Anderson, J. E. (1993). Restriction endonucleases and modification methylases. Curr Op Struct Biol 3, 24-30.
Becher, P. (1957) *Emulsions: theory and practice*. Reinhold, New York.
Benita, S. (ed.). (1996) *Microencapsulation: methods and industrial applications*. Marcel Dekker, New York.
Bemath, K., Hai, M., Mastrobattista, E., Griffiths, A. D., Magdassi, S, and Tawfik, D. S. (2004) In vitro compartmentalization by double emulsions: sorting and gene enrichment by fluorescence activated cell sorting. Anal Biochem, 325, 151-157.
Bru, R. and Walde, P. (1991) Product inhibition of alpha-chymotrypsin in reverse micelles. Eur J Biochem, 199, 95-103.
Bru, R. and Walde, P. (1993) Catalytic activity of elastase in reverse micelles. Biochem Mol Biol Int, 31, 685-692.
Burbaum, J. (1998). Miniaturization technologies in HTS: how fast, how small, how soon? Drug Discov Today 3, 313-322.
Calvert, P. (2001) Inkjet printing for materials and devices. Chem. Mater., 13, 3299-3305.
Chakrabarti, A. C., Breaker, R. R., Joyce, G. F. and Deamer, D. W. (1994) Production of RNA by a polymerase protein encapsulated within phospholipid vesicles. J Mol Evol, 39, 555-559.
Chang, T. M. (1987) Recycling of NAD(P) by multienzyme systems immobilized by microencapsulation in artificial cells. Methods Enzymol, 136, 67-82.
Chang, T. M. S. (1992) Recent advances in artificial cells based on microencapsulation. In Donbrow, M. (ed.), *Microcapsules and nanoparticles in medicine and pharmacy*. CRC Press, Boca Raton, Fla., pp. 323-339.
Creagh, A. L., Prausnitz, J. M. and Blanch, H. W. (1993) Structural and catalytic properties of enzymes in reverse micelles. Enzyme Microb Technol, 15, 383-392.
Curran, D. P. (1998) Strategy-level separations in organic synthesis: from planning to practice. Angew Chem Int Ed, 37, 1174-1196.
Czarnik, A. W. (1997). Encoding methods for combinatorial chemistry. Curr Opin Chem Biol 1, 60-66.
Davis, S. S., and Walker, I. M. (1987). Multiple emulsions as targetable delivery systems. Methods in Enzymology 149, 51-64.
de Gans, B.-J., Duineveld, P. C. and Schubert, U. S. (2004) Inkjet printing of polymers: state of the art and future developments. Advanced materials, 16, 203-213.
Dickinson, E. (1994) Emulsions and droplet size control. In Wedlock, D. J. (ed.), *Controlled particle, droplet and bubble formation*. Butterworth-Heinemann, Oxford, pp. 191-257.
Doi, N., and Yanagawa, H. (1999). STABLE: protein-DNA fusion system for screening of combinatorial protein libraries in vitro. FEBS Lett 457, 227-230.
Doman, T. N., McGovern, S. L., Witherbee, B. J., Kasten, T. P., Kurumbail, R., Stallings, W. C., Connolly, D. T. and Shoichet, B. K. (2002) Molecular docking and high-throughput screening for novel inhibitors of protein tyrosine phosphatase-1B. J Med Chem, 45, 2213-2221.
Finch, C. A. (1993) Encapsulation and controlled release. Spec. Publ.—R. Soc. Chem., 138, 35.
Fomusek & Vetvicka, Crit. Rev Ther Drug Carrier Syst. 1986; 2(2):137-74
Fu, A. Y., Chou, H. P., Spence, C., Arnold, F. H. and Quake, S. R. (2002) An integrated microfabricated cell sorter. Anal Chem, 74, 2451-2457.
Fulton, R. J., McDade, R. L., Smith, P. L., Kienker, L. J. and Kettman, J. R., Jr. (1997) Advanced multiplexed analysis with the FlowMetrix system. Clin Chem, 43, 1749-1756.
Ghadessy, F. J., Ong, J. L. and Holliger, P. (2001) Directed evolution of polymerase function by compartmentalized self-replication. Proc Natl Acad Sci USA, 98, 4552-4557.

Gordon, K., and Balasubramanian, S. (1999). Solid phase chemistry—designer linkers for combinatorial chemistry. J Chem Technol Biotechnol 74, 835-851.

Griffiths, A. D., Williams, S. C., Hartley, O., Tomlinson, I. M., Waterhouse, P., Crosby, W. L., Kontermann, R. E., Jones, P. T., Low, N. M., Allison, T. J., and et al. (1994). Isolation of high affinity human antibodies directly from large synthetic repertoires. Embo J 13, 3245-3260.

Griffiths, A. D. and Tawfik, D. S. (2003) Directed evolution of an extremely fast phosphotriesterase by in vitro compartmentalization. Embo J, 22, 24-35.

Guixe et al., Ligand-induced conformational transitions in Escherichia coli phosphofructokinase 2: evidence for an allosteric site for MgATP2–. Biochemistry. 1998 Sep. 22; 37(38):13269-75.

Haber, J., Maslakiewicz, P., Rodakiewicz, N. J. and Walde, P. (1993) Activity and spectroscopic properties, of bovine liver catalase in sodium bis(2-ethylhexyl)sulfosuccinate/isooctane reverse micelles. Eur J Biochem, 217, 567-573.

Han, M., Gao, X., Su, J. Z., and Nie, S. (2001). Quantum-dot-tagged microbeads for multiplexed optical coding of biomolecules. Nat Biotechnol 19, 631-635.

Han, M., Gao, X., Su, J. Z. and Nie, S. (2001) Quantum-dot-tagged microbeads for multiplexed optical coding of biomolecules. Nat Biotechnol, 19, 631-635.

Handen, J. S. (Summer 2002). High-throughput screening—challenges for the future. Drug Discov World, 47-50.

Harder, K. W., Owen, P., Wong, L. K., Aebersold, R., Clark-Lewis, I., and Jirik, F. R. (1994). Characterization and kinetic analysis of the intracellular domain of human protein tyrosine phosphatase beta (HPTP beta) using synthetic phosphopeptides. Biochem J 298 (Pt 2), 395-401.

Haugland, R. P., (1996). Handbook of fluorescent probes and research chemicals. Spence, M. T. Z. Ed Heim R, Tsien R Y. Engineering green fluorescent protein for improved brightness, longer wavelengths and fluorescence resonance energy transfer. Curr Biol. 1996 Feb. 1; 6(2):178-82.

Hergenrother, P. J., Depew, K. P., and Schreiber, S. L. (2000). Small-molecule microarrays: covalent attachment and screening of alcohol-containing small molecules on glass slides. J Am Chem Soc 122, 7849-7850.

Hermanson, G. T. (1996) Bioconjugate techniques. Academic Press, San Diego.

Hildebrand, J. H. and Cochran, D. F. R. (1949) J. Am. Chem. Soc., 71, 22.

Hochuli, E., Dobeli, H., and Schacher, A. (1987). New metal chelate adsorbent selective for proteins and peptides containing neighbouring histidine residues. J Chromatogr 411, 177-184.

Holmes, C. P., and Jones, D. G. (1995). Reagents for combinatorial organic synthesis: development of a new o-nitrobenzyl photolabile linker for solid phase synthesis. J Org Chem 60, 2318-2319.

Hudlicky, M. (1992) Chemistry of Organic Fluorine Compounds. Ellis Horwood, New York.

Johansson, A. (1991). Heterogeneous enzyme immunoassays. In Principles and practice of immunoassays, C. P. Price, and D. J. Newman, eds. (New York, Stockton Press), pp. 295-325.

Johansson, A., and Bates, D. L. (1988). Amplification by second enzymes. In ELISA and other solid phase immunoassays, D. M. Kemeny, and S. J. Challacombe, eds. (Chichester, John Wiley), pp. 85-106.

Johnson, T. O., Ermolieff, J., and Jirousek, M. R. (2002). Protein tyrosine phosphatase 1B inhibitors for diabetes. Nature Reviews Drug Discovery 1, 696-709.

Keij et al., Cytometry. 1995 Mar. 1; 19(3):209-16

Kerker, Cytometry. 1983 July; 4(1):1-10

Klug, A. (1995). Gene regulatory proteins and their interaction with DNA. Ann NY Acad Sci 758, 143-160.

Klug, A., and Schwabe, J. W. (1995). Protein motifs 5. Zinc fingers. Faseb J 9, 597-604.

Krafft M. P., Chittofrati, A. and Riess, J. G. (2003) Emulsions and microemulsions with a fluorocarbon phase. Curr. Op. Colloid Interface Sci., 8, 251-258.

Kumar, A., Kumar, A. and Katiyar, S. S. (1989) Activity and kinetic characteristics of glutathione reductase in vitro in reverse micellar waterpool. Biochim Biophys Acta, 996, 1-6.

Lee, Y.-F., Tawfik, D. S., and Griffiths, A. D. (2002). Investigating the target recognition of DNA cytosine-5 methyltransferase HhaI by library selection using in vitro compartmentalisation (IVC). Nucleic Acids Res 30, 4937-4944.

Lim, F. (ed.). (1984) Biomedical applications of microencapsulation. CRC Press, Boca Raton, Fla.

Lim, F. and Sun, A. M. (1980), Microencapsulated islets as bioartificial endocrine pancreas. Science, 210, 908-910.

Link, D. R., Anna, S. L., Weitz, D. A. and Stone, H. A. (2004) Geometrically mediated breakup of drops in microfluidic devices. Phys. Rev. Letts., 92, 054503.

Lipinski, C. A., Lombardo, F., Dominy, B. W. and Feeney, P. J. (2001) Experimental and computational approaches to estimate solubility and permeability in drug discovery and development settings. Adv Drug Deilv Rev, 46, 3-26.

Lissant, K. J. (ed.). (1974) Emulsions and emulsion technology. Marcel Dekker, New York.

Lissant, K. J. (ed.). (1984) Emulsions and emulsion technology. Marcel Dekker, New York.

Lowe, K. C. (2002) Perfluorochemical respiratory gas carriers: benefits to cell culture systems. J. Fluorine Chem., 118, 19-26.

Luisi, P. L. and B., S.-H. (1987) Activity and conformation of enzymes in reverse micellar solutions. Methods Enzymol, 136, 188-216.

Lyne, P. D. (2002). Structure-based virtual screening: an overview. Drug Discov Today 7, 1047-1055.

Mackenzie and Pinder, Dev Biol Stand. 1986; 64:181-93.

Mahajan N P, Linder K, Berry G, Gordon G W, Heim R, Herman B. Bcl-2 and Bax interactions in mitochondria probed with green fluorescent protein and fluorescence resonance energy transfer. Nat. Biotechnol. 1998 June; 16(6):547-52.

Mao, Q. and Walde, P. (1991) Substrate effects on the enzymatic activity of alpha-chymotrypsin in reverse micelles. Biochem Biophys Res Commun, 178, 1105-1112.

Mao, Q., Walde, P. and Luisi, P. L. (1992) Kinetic behaviour of alpha-chymotrypsin in reverse micelles. A stopped-flow study. Eur J Biochem, 208, 165-170.

Masui and Kuramitsu, Probing of DNA-binding sites of Escherichia coli RecA protein utilizing 1-anilinonaphthalene-8-sulfonic acid. Biochemistry. 1998 Sep. 1; 37 (35): 12133-43

McDonald, J. C. and Whitesides, G. M. (2002) Poly(dimethylsiloxane) as a material for fabricating microfluidic devices. Acc Chem Res, 35, 491-499.

Menger, F. M. and Yamada, K. (1979) J. Am. Chem. Soc., 101, 6731-6734.

Meylan, W. M. and Howard, P. H. (1995) Atom/fragment contribution method for estimating octanol-water partition coefficients. J Pharm Sci, 84, 83-92.

Miyawaki A, Llopis J, Heim R, McCaffery J M, Adams J A, Ikura M, Tsien R Y. Fluorescent indicators for Ca2+ based on green fluorescent proteins and calmodulin. Nature. 1997 Aug. 28; 388(6645):882-7.

Mize, P. D., Hoke; R. A., Linn, C. P., Reardon, J. E., and Schulte, T. H. (1989). Dual-enzyme cascade—an amplified method for the detection of alkaline phosphatase. Anal Biochem 179, 229-235.

Montigiani, S., Neri, G., Neri, P., and Neri, D. (1996). Alanine substitutions in calmodulin-binding peptides result in unexpected affinity enhancement. J Mol Biol 258, 6-13.

New, R. R. C. (ed.). (1990) *Liposomes: a practical approach.* Oxford University Press, Oxford.

Norman, Med. Phys. 1980 November-December; 7(6):609-15.

Oberholzer, T., Albrizio, M. and Luisi, P. L. (1995) Polymerase chain reaction in liposomes. *Chem Biol,* 2, 677-682.

Oberholzer, T., Wick, R., Luisi, P. L. and Biebricher, C. K. (1995) Enzymatic RNA replication in self-reproducing vesicles: an approach to a minimal cell. *Biochem Biophys Res Commun,* 207, 250-257.

Obukowicz, M. G., Turner, M. A., Wong, E. Y. and Tacon, W. C. (1988) Secretion and export of IGF-1 in *Escherichia coli* strain JM101. *Mol Gen Genet,* 215, 19-25.

Perelson, A. S., and Oster, G. F. (1979). Theoretical studies of clonal selection: minimal antibody repertoire size and reliability of self-non-self discrimination. J Theor Biol 81, 645-670.

Perez, G. M., Sanchez, F. A. and Garcia, C. F. (1992) Application of active-phase plot to the kinetic analysis of lipoxygenase in reverse micelles. *Biochem J.*

Pirrung, M. C., and Huang, C. Y. (1996). A general method for the spatially defined immobilization of biomolecules on glass surfaces using "caged" biotin. Bioconjug Chem 7, 317-321.

Qi and Grabowski, Acid beta-glucosidase: intrinsic fluorescence and conformational changes induced by phospholipids and saposin C. Biochemistry. 1998 Aug. 18; 37(33): 11544-54

Ramstrom, O., and Lehn, J. M. (2002). Drug discovery by dynamic combinatorial libraries. Nat Rev Drug Discov 1, 26-36.

Riess, J. G. (2002) Fluorous micro- and nanophases with a biomedical perspective. *Tetrahedron,* 58, 4113-4131.

Rolland, I Immunol Methods. 1985 Jan. 21; 76(1):1-10

Sadder, V. M., Krafft, M. P. and Riess, J. G. (1996) Achieving stable, reverse water-in-fluorocarbon emulsions. *Angew. Chem. Int. Ed. Engl.,* 35, 1976-1978.

Sambrook, J., and Russell, D. W., eds. (2001). Molecular cloning: a laboratory manual (New York, Cold Spring Harbor Laboratory Press).

Savage, M. D., Mattson, G., Desai, S., Nielander, G. W., Morgensen, S., and Conklin, E. J. (1994). Avidin-biotin chemistry: a handbook, 2 edn (Rockford, Pierce Chemical Company).

Schick, M. J. (1966) *Nonionic surfactants.* Marcel Dekker, New York.

Scott, R. L. (1948) *J. Am. Chem. Soc.,* 70, 4090.

Sepp, A., Tawfik, D. S., and Griffiths, A: D. (2002). Microbead display by in vitro compartmentalisation: selection for binding using flow cytometry. FEBS Letters 532, 455-458.

Shapiro, H. M. (1995). Practical Flow Cytometry, 3 edn (New York, Wiley-Liss).

Sherman, P. (1968) *Emulsion science.* Academic Press, London.

Song, H. and Ismagilov, R. F. (2003) Millisecond kinetics on a microfluidic chip using nanoliters of reagents. *J. Am Chem Soc,* 125, 14613-14619.

Song, H., Tice, J. D. and Ismagilov, R. F. (2003) A microfluidic system for controlling reaction networks in time. *Angew. Chem. Int. Ed. Engl.,* 42, 767-772.

Stofko, H. R., Carr, D. W., and Scott, J. D. (1992). A single step purification for recombinant proteins. Characterization of a microtubule associated protein (MAP 2) fragment which associates with the type II cAMP-dependent protein kinase. Febs Lett 302, 274-278.

Studer, A., Hadida, S., Ferritto, R., Kim, S. Y., Jeger, P., Wipf, P. and Curran, D. P. (1997) Fluorous synthesis: a fluorous-phase strategy for improving separation efficiency in organic synthesis. *Science,* 275, 823-826.

Sun, A. M., Vasek, I. and Tai, I. (1992) Microencapsulation of living cells and tissues. In Donbrow, M. (ed.), *Microencapsulation and nanoparticles in medicine and pharmacy.* CRC Press, Boca Raton, Fla., pp. 315-322.

Sundberg, S. A., Barrett, R. W., Pirrung, M., Lu, A. L., Kiangsoontra, B., and Holmes, C. P. (1995). Spatially-addressable immobilisation of macromolecules on solid supports. J Am Chem Soc 117, 12050-12057.

Tawfik, D. S., and Griffiths, A. D. (1998). Man-made cell-like compartments for molecular evolution. Nat Biotechnol 16, 652-656.

Thorsen, T., R. W., R., Arnold, F. H. and Quake, S. R. (2001) Dynamic pattern formation in a vesicle-generating microfluidic device. *Phys. Rev. Letts.,* 86, 4163-4166.

Tripet, B., Yu, L., Bautista, D. L., Wong, W. Y., Irvin, R. T., and Hodges, R. S. (1996). Engineering a de novo-designed coiled-coil heterodimerization domain off the rapid detection, purification and characterization of recombinantly expressed peptides and proteins. Protein Eng 9, 1029-1042.

Umbanhowar, P. B., Prasad, V. and Weitz, D. A. (2000) Monodisperse emulsions generated via drop break off in a coflowing steam. *Langmuir,* 16, 347-351.

van Hal, D. A., Bouwstra, J. A. and Junginger, H. E. (1996) Nonionic surfactant vesicles containing estradiol for topical application. In Benita, S. (ed.), *Microencapsulation: methods and industrial applications.* Marcel Dekker, New York, pp. 329-341.

Voss E W Jr. Kinetic measurements of molecular interactions by spectrofluorometry. J Mol. Recognit. 1993 June; 6(2):51-8

Walde, P., Goto, A., Monnard, P.-A., Wessicken, M. and Luisi, P. L. (1994) Oparin's reactions revisited: enzymatic synthesis of poly(adenylic acid) in micelles and self-reproducing vesicles. *J. Am. Chem. Soc.,* 116, 7541-7547.

Walde, P., Han, D. and Luisi, P. L. (1993) Spectroscopic and kinetic studies of lipases solubilized in reverse micelles. *Biochemistry,* 32, 4029-4034.

Walde, P., Peng, Q., Fadnavis, N. W., Battistel, E. and Luisi, P. L. (1988) Structure and activity of trypsin in reverse micelles. *Eur J Biochem,* 173, 401-409.

Whateley, T. L. (1996) Microcapsules: preparation by interfacial polymerisation and interfacial complexation and their applications. In Benita, S. (ed.), *Microencapsulation: methods and industrial applications.* Marcel Dekker, New York, pp. 349-375.

Wick, R. and Luisi, P. L. (1996) Enzyme-containing liposomes can endogenously produce membrane-constituting lipids. *Chem Biol,* 3, 277-285.

Zhang, Z. Y., Thieme-Sefler, A. M., Maclean, D., McNamara, D. J., Dobrusin, E. M., Sawyer, T. K., and Dixon, J. E. (1993). Substrate specificity of the protein tyrosine phosphatases. Proc Natl Acad Sci USA 90, 4446-4450.

All publications mentioned in the above specification, and references cited in said publications, are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A water-in-perfluorocarbon oil emulsion library comprising:
 (a) a perfluorocarbon oil comprising a fluorinated surfactant; and (b) a plurality of individual aqueous microdroplets encapsulated by the perfluorocarbon oil, each aqueous microdroplet of the plurality of individual aqueous microdroplets comprising;
  (i) a subset of non-fluorinated nucleic acids, comprising one or more non-fluorinated nucleic acids from of a repertoire of non-fluorinated nucleic acids, wherein the repertoire of non-fluorinated nucleic acids in a plurality of individual aqueous microdroplets are structurally different;
  (ii) a biological target enzyme that is reactive with one or more of the nucleic acids from the repertoire of non-fluorinated nucleic acids; and
  (iii) a fluorogenic substrate of the biological target enzyme; wherein each non-fluorinated nucleic acids of the each subset of the repertoire of non-fluorinated nucleic acids is insoluble in the perfluorocarbon oil, and wherein the fluorogenic substrate of the biological target enzyme comprises an optical tag, wherein the optical tag produces a selectable change upon complexation of the fluorogenic substrate with the biological target enzyme.

2. The water-in-perfluorocarbon oil emulsion library according to claim 1, wherein the aqueous microdroplets further comprise microbeads.

3. The water-in-perfluorocarbon oil emulsion library according to claim 2, wherein the repertoire of non-fluorinated nucleic acids are releasably attached to the microbeads.

4. The water-in-perfluorocarbon emulsion library according to claim 1, wherein the biological target enzyme in each of the aqueous microdroplets is structurally different.

5. The water-in-perfluorocarbon oil emulsion library according to claim 1, wherein each aqueous microdroplet further comprises a member of a binding pair.

6. The water-in-perfluorocarbon oil emulsion library according to claim 5, wherein a member of a binding pair is an antibody.

7. A water-in-perfluorocarbon oil emulsion library comprising: a perfluorocarbon oil comprising: (a) a fluorosurfactant; and (b) a plurality of individual aqueous microdroplets, wherein each aqueous microdroplet of the plurality of individual aqueous microdroplets is individually encapsulated within the perfluorinated oil and comprises:
 (i) multiple copies of a single type of nucleic acid, wherein the single type of nucleic acid is insoluble in the perfluorocarbon oil; and
 (ii) a target cell, wherein the target cell comprises a biological target enzyme that is reactive with one or more of the multiple copies of the single type of nucleic acid; and a fluorogenic substrate of the biological target enzyme, wherein the fluorogenic substrate of the biological target enzyme comprises an optical tag, wherein the optical tag produces a selectable change upon complexation of the fluorogenic substrate with the biological target enzyme.

8. The water-in-perfluorocarbon oil emulsion library according to claim 7, wherein the single type of nucleic acid is attached to a microbead.

9. The water-in-perfluorocarbon oil emulsion library according to claim 8, wherein the single type of nucleic acid is releasably attached to a microbead.

* * * * *